(12) United States Patent
Lin et al.

(10) Patent No.: US 8,455,528 B2
(45) Date of Patent: Jun. 4, 2013

(54) IMIDAZOLE DERIVATIVES USEFUL AS INHIBITORS OF FAAH

(75) Inventors: Linus S. Lin, Westfield, NJ (US); Marc D. Chioda, Metuchen, NJ (US); Ping Liu, Westfield, NJ (US); Ravi P. Nargund, East Brunswick, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/996,429

(22) PCT Filed: Jun. 4, 2009

(86) PCT No.: PCT/US2009/046241
§ 371 (c)(1),
(2), (4) Date: Dec. 6, 2010

(87) PCT Pub. No.: WO2009/152025
PCT Pub. Date: Dec. 17, 2009

(65) Prior Publication Data
US 2011/0269769 A1   Nov. 3, 2011

Related U.S. Application Data

(60) Provisional application No. 61/131,669, filed on Jun. 11, 2008.

(51) Int. Cl.
*A61K 31/4174* (2006.01)
*A61K 31/4178* (2006.01)
*C07D 233/84* (2006.01)

(52) U.S. Cl.
CPC ......... *A61K 31/4174* (2013.01); *C07D 233/84* (2013.01); *A61K 31/4178* (2013.01)
USPC ...................................... 514/397; 548/311.1

(58) Field of Classification Search
USPC ....................................... 548/311.1; 514/397
See application file for complete search history.

(56) References Cited

U.S. PATENT DOCUMENTS 7,057,051 B2 *  6/2006  Finke et al. ................ 548/334.5
7,220,770 B2    5/2007  Khanna et al.

* cited by examiner

*Primary Examiner* — Kamal Saeed
*Assistant Examiner* — Janet L Coppins
(74) *Attorney, Agent, or Firm* — Maria V. Marucci

(57) ABSTRACT

The present invention is directed to certain imidazole derivatives which are useful as inhibitors of Fatty Acid Amide Hydrolase (FAAH). The invention is also concerned with pharmaceutical formulations comprising these compounds as active ingredients and the use of the compounds and their formulations in the treatment of certain disorders, including osteoarthritis, rheumatoid arthritis, diabetic neuropathy, postherpetic neuralgia, skeletomuscular pain, and fibromyalgia, as well as acute pain, migraine, sleep disorder, Alzeimer Disease, and Parkinson's Disease.

17 Claims, No Drawings

IMIDAZOLE DERIVATIVES USEFUL AS INHIBITORS OF FAAH

CROSS REFERENCE TO RELATED APPLICATIONS

This application is a U.S. National Phase application under 35 U.S.C. §371 of PCT Application No. PCT/US2009/046241, filed Jun. 4, 2009, which claims priority under 35 U.S.C. §119(e) from U.S. Provisional Application Ser. No. 61/131,669, filed Jun. 11, 2008.

REFERENCE TO A SEQUENCE LISTING SUBMITTED AS A TEXT FILE VIA EFS-WEB

The Sequence Listing is submitted as a text file via EFS-Web with a file name of MRL-BRE-22518-US-PCT.txt, a creation date of Mar. 2, 2011, and a size of 1 kilobyte. The Sequence Listing filed via EFS-Web is part of the specification and is hereby incorporated in its entirety by reference herein.

BACKGROUND OF THE INVENTION

Disclosed herein are compounds that inhibit the activity of fatty acid amide hydrolase (FAAH), compositions that include the compounds, and methods of their use. Compounds disclosed herein as inhibitors of fatty acid amide hydrolase (FAAH) are useful in the treatment of diseases, disorders, or conditions that would benefit from the inhibition of fatty acid amide hydrolase and increases in endogenous fatty acid amides.

Fatty acid amide hydrolase (FAAH) is an enzyme that is abundantly expressed throughout the CNS (Freund et al. Physiol. Rev. 2003; 83:1017-1066) as well as in peripheral tissues, such as, for example, in the pancreas, brain, kidney, skeletal muscle, placenta, and liver (Giang, D. K. et al., Proc. Natl. Acad. Sci. U.S.A. 1997, 94, 2238-2242; Cravatt et al. Proc. Natl. Acad. Sci. U.S.A. 2004, 101, 29, 10821-10826). FAAH hydrolyzes the fatty acid amide (FAA) family of endogenous signaling lipids. General classes of fatty acid amides include the N-acylethanolamides (NAEs) and fatty acid primary amides (FAPAs). Examples of NAEs include anandamide (AEA), palmitoylethanolamide (PEA) and oleoylethanolamide (OEA). An example of FAPAs includes 9-Z-octadecenamide or oleamide. (McKinney M K and Cravatt B F. 2005. Annu Rev Biochem 74:411-32). Another class of fatty acid amide family of endogenous signaling lipids is N-acyl taurines that have also been shown to be elevated upon FAAH deletion or inhibition and appear to act on transient receptor potential (TRP) family of calcium channels, although the functional consequences are not yet clear (Saghatelian A, et al. Biochemistry. 2004, 43:14332-9, Saghatelian A, et al. Biochemistry, 2006, 45:9007-9015). In addition to fatty acid amides, FAAH can also hydrolyze certain fatty acid esters, such as, for example, 2-arachidonylglycerol (2-AG) another endocannabinoid (Mechoulam et al. Biochem. Pharmacol. 1995; 50:83-90; Stella et al. Nature, 1997; 388:773-778; Suguria et al. Biochem. Biophys. Res. Commun. 1995; 215:89-97).

Inhibition of FAAH is expected to lead to an increase in the level of anandamide and other fatty acid amides. This increase in fatty acid amides leads to an increase in the noiceptive threshold. Thus, inhibitors of FAAH are useful in the treatment of pain (Cravatt, B F; Lichtman, A H Current Opinion in Chemical Biology 2003, 7, 469-475). Such inhibitors are useful in the treatment of other disorders that can be treated using fatty acid amides or modulators of cannabinoid receptors, such as, for example, anxiety, sleep disorder, Alzheimer disease, and Parkinson's disease, eating disorders, metabolic disorders, cardiovascular disorders, and inflammation (Simon et al Archives of Gen. Psychiatry, 2006, 63, 824-830. Kunos, G et al. *Pharmacol Rev* 2006, 58, 389-462). In some embodiments, FAAH inhibitor compounds may be peripherally restricted and may not substantially affect neural disorders, such as, for example, depression and anxiety. Finally, agonism of cannabinoid receptors has also been shown to reduce the progression of atherosclerosis in animal models (see Steffens et al. Nature, 2005, 434, 782-786; and Steffens et al., Curr Opin. Lipid., 2006, 17, 519-526). Thus, increasing the level of endogenous cannabinergic fatty acid amides (e.g., anandamide) is expected to effectively treat or reduce the risk of developing atherosclerosis.

Inhibition of FAAH also leads to elevation of pahnitoylethanolamide which is thought to work, in part, through activation of the peroxisome proliferator-activated receptor α (PPAR-α) to regulate multiple pathways including, for example, pain perception in neuropathic and inflammatory conditions such as convulsions, neurotoxicity, spacticity and to reduce inflammation, for example, in atopic eczema and arthritis (LoVenne J et al. The nuclear receptor peroxisome proliferator-activated receptor-alpha mediates the anti-inflammatory actions of palmitoylethanolamide. *Mol Pharmacol* 2005, 67, 15-19; LoVerme J et al The search for the palmitoylethanolamide receptor. *Life Sci* 2005, 77: 1685-1698. Lambert D M et al. The palmitoylethanolamide family: a new class of anti-inflammatory agents? *Curr Med Chem* 2002, 9: 663-674; Eberlein B, et al. Adjuvant treatment of atopic eczema: assessment of an emollient containing N-palmitoylethanolamine (ATOPA study). J Eur Acad Dermatol Venereol. 2008, 22:73-82. Re G, et al. Palmitoylethanolamide, endocannabinoids and related cannabimimetic compounds in protection against tissue inflammation and pain: potential use in companion animals. Vet J. 2007 173: 21-30.). Thus, inhibition of FAAH is useful for the treatment of various pain and inflammatory conditions, such as osteoarthritis, rheumatoid arthritis, diabetic neuropathy, postherpetic neuralgia, skeletomuscular pain, and fibromyalgia.

It is also thought that certain fatty acid amides, such as, for example, OEA, act through the peroxisome proliferator-activated receptor α (PPAR-α) to regulate diverse physiological processes, including, e.g., feeding and lipolysis. Consistent with this, human adipose tissue has been shown to bind and metabolize endocannabinoids such as anandamide and 2-arachidonylglyeerol (see Spoto et al., Biochimie 2006, 88, 1889-1897; and Matias et al., J. Clin. Endocrin. & Met., 2006, 91, 3171-3180). Thus, inhibiting FAAH activity in vivo leads to reduced body fat, body weight, caloric intake, and liver triglyceride levels. However, unlike other anti-lipidemic agents that act through PPAR-α, e.g., fibrates, FAAH inhibitors do not cause adverse side effects such as rash, fatigue, headache, erectile dysfunction, and, more rarely, anemia, leukopenia, angioedema, and hepatitis (see, e.g., Muscari et al. Cardiology, 2002, 97: 115-121).

Many fatty acid amides are produced on demand and rapidly degraded by FAAH. As a result, hydrolysis by FAAH is considered to be one of the essential steps in the regulation of fatty acid amide levels in the central nervous system as well as in peripheral tissues and fluids. The broad distribution of FAAH combined with the broad array of biological effects of fatty acid amides (both endocannabinoid and non-endocannabinoid mechanisms) suggests that inhibition of FAAH leads to altered levels of fatty acid amides in many tissues and fluids and may be useful to treat many different conditions.

FAAH inhibitors increase the levels of endogenous fatty acid amides. FAAH inhibitors block the degradation of endocannabinoids and increase the tissue levels of these endogenous substances. FAAH inhibitors can be used in this respect in the prevention and treatment of pathologies in which endogenous cannabinoids and or any other substrates metabolized by the FAAH enzyme are involved.

The various fatty acid ethanolarnides have important and diverse physiological functions. As a result, inhibitor molecules that selectively inhibit FAAH enzymatic activity would allow a corresponding selective modulation of the cellular and extra-cellular concentrations of a FAAH substrate. FAAH inhibitors that are biologically compatible could be effective pharmaceutical compounds when formulated as therapeutic agents for any clinical indication where FAAH enzymatic inhibition is desired. In some embodiments, FAAH activity in peripheral tissues can be preferentially inhibited. In some embodiments, FAAH inhibitors that do substantially cross the blood-brain-barrier can be used to preferentially inhibit FAAH activity in peripheral tissues. In some embodiments, FAAH inhibitors that preferentially inhibit FAAH activity in peripheral tissues can minimize the effects of FAAH inhibition in the central nervous system. In some embodiments, it is preferred to inhibit FAAH activity in peripheral tissues and minimize FAAH inhibition in the central nervous system.

SUMMARY OF THE INVENTION

The present invention is directed to certain imidazole derivatives which are useful as inhibitors of Fatty Acid Amide Hydrolase (FAAH). The invention is also concerned with pharmaceutical formulations comprising these compounds as active ingredients and the use of the compounds and their formulations in the treatment of certain disorders, including osteoarthritis, rheumatoid arthritis, diabetic neuropathy, postherpetic neuralgia, skeletomuscular pain, and fibromyalgia, as well as acute pain, migraine, sleep disorder, Alzheimer disease, and Parkinson's disease.

DETAILED DESCRIPTION OF THE INVENTION

In one aspect the invention is directed to compounds of formula I and II:

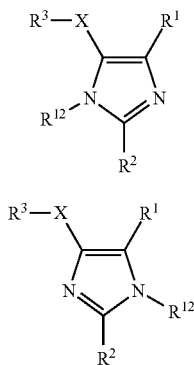

or a pharmaceutically acceptable salt thereof wherein:
X is S or SO;
$R^{12}$ is selected from the group consisting of
  (1) —$C_{1-4}$alkyl,
  (2) -halo$C_{1-4}$alkyl,
  (3) H;

n is 0, 1 or 2;
$R^1$ is selected from the group consisting of:
  (1) aryl, and
  (2) $HET^1$,
wherein choice (1) and (2), is optionally mono or di-substituted with substituents $R^4$ and $R^5$, which are independently selected from the group consisting of:
  (a) halo,
  (b) —CN,
  (c) mono, di or tri-halo $C_{1-4}$ alkyl,
  (d) —$OC_{1-4}$ alkyl, optionally substituted with hydroxy, halo or amino,
  (e) —$C_{1-4}$alkyl optionally substituted with one or two substituents selected from hydroxyl, CN, —$CHF_2$ and —$CF_3$,
  (f) —$C_{1-2}$alkyl-$C_{3-6}$cycloalkyl optionally substituted with hydroxy, halo or CN,
  (g) —$S(O)_nC_{1-4}$alkyl,
  (h) —$S(O)_nNR^6R^7$,
  (i) —$C(O)$—NH—$NR^8R^9$,
  (j) —C(O)—OH,
  (k) —$C(O)$—$OC_{1-4}$alkyl, optionally substituted with halo or hydroxy,
  (l) —$C(O)$—$NR^{10}R^{11}$,
  (m) —$C(O)$—$C_{1-4}$alkyl optionally mono, di or tri substituted with halo,
  (o) —$C(NR^{12})$—$NR^{13}R^{14}$,
  (p) $HET^4$,
  (q) aryl,
  (r) —C(O)—NH—NH—C(O)H,
  (s) —$CH_2$—C(O)—O—$C_{1-4}$alkyl, whereas the $CH_2$ may be optionally substituted with $C_{1-4}$ alkyl or OH
  (t) —$CH_2$—$C(O)NR_{15}R_{16}$, whereas the $CH_2$ may be optionally substituted with $C_{1-4}$ alkyl or OH, and
  (u) —$NR^{17}R^{18}$,
wherein choices (p) and (q) are each optionally mono or di-substituted with substituents selected from
  (1) halo,
  (2) —CN,
  (3) —OH,
  (4) —$C_{1-4}$alkyl optionally substituted with hydroxy, halo or cyano,
  (5) —$CF_3$,
  (6) —$OC_{1-4}$alkyl optionally substituted with hydroxyl or halo,
  (7) —C(O)OH, and
  (8) —C(O)O—$C_{1-3}$alkyl;
  (9) —$C(O)$—$NR^{19}R^{20}$,
  (10) —$NH_2$,
  (11) Oxo,
  (12) =S,
wherein $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$, are each independently selected from H and $C_{1-4}$alkyl,
or
$R^6$ and $R^7$ or $R^8$ and $R^9$ or $R^{10}$ and $R^{11}$ or $R^{13}$ and $R^{14}$ or $R^{15}$ and $R^{16}$ or $R^{17}$ and $R^{18}$ or $R^{19}$ and $R^{20}$ are joined together so that together with the atoms to which they are attached there is formed a 5-membered heterocyclic ring of 4 to 7 atoms, said ring containing 1, 2, 3 or 4 heteroatoms selected from N, O and S, said ring being optionally mono or di-substituted with substituents independently selected from halo, hydroxyl, oxo, $C_{1-4}$alkyl, hydroxy$C_{1-4}$alkyl, halo$C_{1-4}$alkyl, —$C(O)$—$C_{1-4}$alkyl and —$S(O)nC_{1-4}$alkyl;

$R^2$ is selected from the group consisting of:
- (1) aryl,
- (2) $HET^3$,
- (3) —$CH_2$-aryl,
- (4) —$CH_2$-$HET^3$,
- (5) —$C_{1-6}$alkyl, and
- (6) —$C_{3-6}$cycloalkyl, wherein choice (1), (2), (3), (4), (5) and (6) is optionally mono or di-substituted with substituents independently selected from the group consisting of:
- (a) halo,
- (b) —CN,
- (c) —OH,
- (d) —$C_{1-4}$alkyl optionally substituted with hydroxy, halo or cyano,
- (e) —$CF_3$,
- (f) —$OC_{1-4}$alkyl optionally substituted with hydroxyl or halo,
- (g) —C(O)O—$C_{1-3}$alkyl;

$R^3$ is selected from the group consisting of:
- (1) aryl,
- (2) $HET^5$, and
- (3) $C_{3-6}$cycloalkyl,
  wherein choice (1), (2) and (3) are each optionally mono or di-substituted with substituents independently selected from the group consisting of:
  - (a) hydroxy,
  - (b) halo,
  - (c) —$C_{3-6}$cycloalkyl,
  - (d) —$OC_{3-5}$cycloalkyl,
  - (e) —$C_{1-4}$ alkyl,
  - (f) —$OC_{1-4}$ alkyl,
  - (g) —C(O)$CH_3$
  - (h) mono, di or tri-halo $C_{1-4}$ alkyl,
  - (i) mono, di or tri-halo —$OC_{1-4}$ alkyl, and
  - (j) —S(O)$_n$—$C_{1-4}$ alkyl.

Within this aspect there is a genus wherein:
$R^1$ is selected from the group consisting of:
- (1) phenyl,
- (2) pyridinyl,
- (3) pyridazinyl,
- (4) pyrimidinyl,
- (5) pyrazinyl,
- (6) thiazolyl,
- (7) thienyl,
- (8) pyrrolyl,
- (9) oxazolyl, and
- (10) a bicyclic ring selected from the group consisting of:

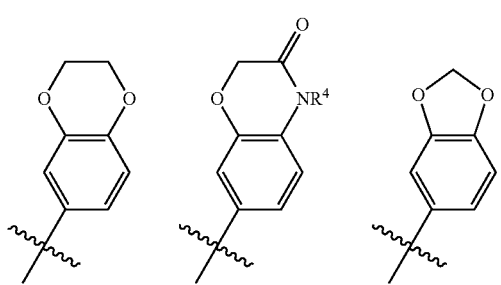

-continued

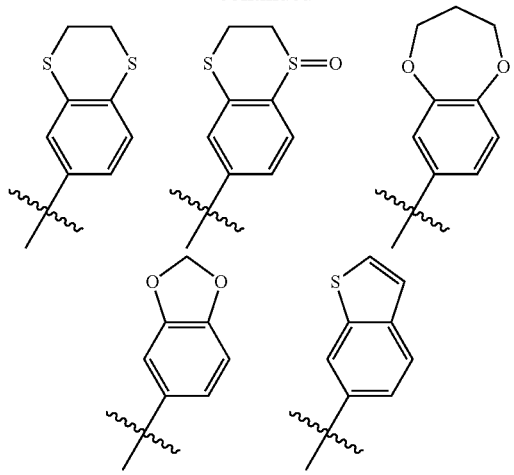

wherein choice of (1) to (9) are each optionally mono or di-substituted with substituents $R^4$ and $R^5$, which are independently selected from the group consisting of
- (a) halo,
- (b) —CN,
- (c) mono, di or tri-halo $C_{1-4}$ alkyl,
- (d) —O—$C_{1-4}$alkyl, optionally substituted with hydroxyl, halo or amino
- (e) —$C_{1-4}$alkyl optionally substituted with hydroxyl or CN,
- (f) —$C_{1-2}$alkyl-$C_{3-6}$cycloalkyl optionally substituted with hydroxy,
- (h) —S(O)$_n$$C_{1-4}$alkyl wherein n is 0, 1 or 2,
- (i) —S(O)$_n$$NR^6R^7$,
- (j) —C(O)—$NR^{10}R^{11}$,
- (k) $HET^4$,
- (l) aryl, and wherein choices (k) and (l) are each optionally mono or di-substituted with substituents selected from
- (1) halo,
- (2) —CN,
- (3) —OH,
- (4) —$C_{1-4}$alkyl optionally substituted with hydroxy, halo or cyano,
- (5) —$CF_3$,
- (6) —$OC_{1-4}$alkyl optionally substituted with hydroxyl or halo,
- (7) —C(O)OH,
- (8) —C(O)O—$C_{1-3}$alkyl, and
- (9) —C(O)—$NR^{19}R^{20}$, wherein $R^6$, $R^7$, $R^{10}$, $R^{11}$, $R^{19}$ and $R^{20}$, are each independently selected from H and $C_{1-4}$alkyl, or
$R^6$ and $R^7$ or $R^{10}$ and $R^{11}$ or $R^{19}$ and $R^{20}$ are joined together so that together with the atoms to which they are attached there is formed a 5 membered heterocyclic ring of 4 to 7 atoms, said ring containing 1, 2, 3 or 4 heteroatoms selected from N, O and S, said ring being optionally mono or di-substituted with substituents independently selected from halo, hydroxyl, $C_{1-4}$alkyl, —C(O)—$C_{1-4}$alkyl and —S(O)n$C_{1-4}$alkyl.

Within this genus there is a sub-genus wherein:
$R^1$ is selected from the group consisting of:
- (1) phenyl,
- (2) pyridinyl,
- (3) pyrimidinyl,
- (4) pyrazinyl, and
- (5) pyridazinyl, optionally mono or di-substituted with substituents $R^4$ and $R^5$, which are independently selected from the group consisting of
    (a) —$C_{1-4}$alkyl optionally substituted with hydroxy,
    (b) —$S(O)_nC_{1-4}$alkyl,
    (c) —$C(O)$—$NR^{10}R^{11}$,
    (d) $HET^4$, and
    (e) halo,
wherein choice (d) is optionally mono or di-substituted with substituents selected from:
    (1) halo,
    (2) —CN,
    (3) —OH,
    (4) —$C_{1-4}$alkyl optionally substituted with hydroxy, halo or cyano,
    (5) —$CF_3$,
    (6) —$OC_{1-4}$alkyl optionally substituted with hydroxyl or halo,
    (7) —C(O)OH, and
    (8) —C(O)O—$C_{1-3}$alkyl, and
    (9) —C(O)—$NR^{19}R^{20}$,
wherein $R^{10}$, $R^{11}$, $R^{19}$ and $R^{20}$ are each independently selected from H and $C_{1-4}$alkyl, or $R^{10}$ and $R^{11}$ or $R^{19}$ and $R^{20}$ are joined together so that together with the atoms to which they are attached there is formed a 5 membered heterocyclic ring of 4 to 7 atoms, said ring containing 1, 2, 3 or 4 heteroatoms selected from N, O and S, said ring being optionally mono or di-substituted with substituents independently selected from halo, hydroxyl, $C_{1-4}$alkyl, —C(O)—$C_{1-4}$ alkyl and —$S(O)nC_{1-4}$alkyl.

Within this aspect there is a genus wherein:
$R^2$ is selected from the group consisting of:
    (1) aryl,
    (2) $HET^3$,
    (3) —$C_{1-6}$alkyl, and
    (4) —$C_{3-6}$cycloalkyl,
wherein choice (1), (2), (3), and (4) is optionally mono or di-substituted with substituents independently selected from the group consisting of
    (a) halo,
    (b) —CN,
    (c) —OH,
    (d) -Hydroxy $C_{1-4}$alkyl,
    (e) —$C_{1-4}$alkyl,
    (f) —$C_{1-4}$haloalkyl, and
    (g) —$OC_{1-4}$alkyl, optionally substituted with halo or hydroxyl.

Within this genus there is a sub-genus wherein:
$R^2$ is selected from the group consisting of:
    (1) aryl, and
    (2) $HET^3$,
wherein choice (1) and (2) are each optionally mono or di-substituted with substituents independently selected from the group consisting of
    (a) halo,
    (b) —CN,
    (c) —OH,
    (d) -hydroxy $C_{1-4}$alkyl,
    (e) —$CH_3$,
    (f) —$CF_3$, and
    (g) —$OCH_3$.

Within this genus there is a sub-genus wherein:
$R^2$ is selected from the group consisting of:
    (1) phenyl,
    (2) pyridinyl,
    (3) pyridazinyl,
    (4) pyrimidinyl,
    (5) pyrazinyl,
    (5) thiazolyl,
    (6) oxazolyl, and
    (7) pyrazolyl,
wherein choice (1), (2), (3), (4), (5), (6) and (7) are each optionally mono or di-substituted with halo, $OC_{1-4}$alkyl optionally substituted with halogen, —$C_{1-4}$haloalkyl, hydroxyl and CN.

Within this aspect there is a genus wherein
$R^3$ is selected from the group consisting of:
    (1) aryl, and
    (2) $HET^5$,
    wherein choice (1) and (2) are each optionally mono or di-substituted with substituents independently selected from the group consisting of:
        (a) halo,
        (b) —$C_{3-6}$cycloalkyl,
        (c) —$C_{1-4}$ alkyl,
        (d) —$OC_{1-4}$ alkyl,
        (e) mono, di or tri-halo $C_{1-4}$ alkyl, and
        (f) mono, di or tri-halo —$OC_{1-4}$ alkyl.

Within this genus there is a sub-genus wherein
$R^3$ is selected from the group consisting of:
    (1) phenyl,
    (2) pyrimidinyl, and
    (3) pyridinyl,
        wherein choices (1), (2) and (3) are each optionally mono or di-substituted with halo, halo$C_{1-4}$alkyl, or —$OC_{1-4}$alkyl optionally substituted with halo.

Within this aspect there is a genus wherein X is S and $R^{12}$ is methyl.

Within this aspect there is a genus of the Formulae

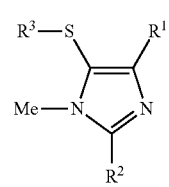

Ia $R^1$ is selected from the group consisting of:
    (1) phenyl,
    (2) pyridinyl,
    (3) pyridazinyl,
    (4) pyrimidinyl,
    (5) pyrazinyl,
    (6) thiazolyl,
    (7) thienyl,
    (8) pyrrolyl,
    (9) oxazolyl, and
    (10) a bicyclic ring selected from the group consisting of:

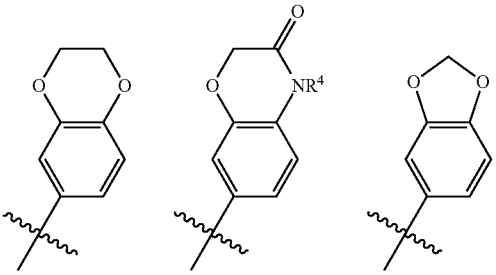

-continued

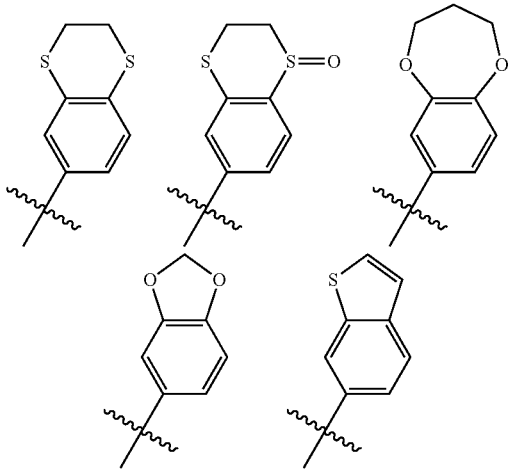

wherein choice of (1) to (9) are each optionally mono or di-substituted with substituents $R^4$ and $R^5$, which are independently selected from the group consisting of
(a) halo,
(b) —CN,
(c) mono, di or tri-halo $C_{1-4}$ alkyl,
(d) —O—$C_{1-4}$alkyl, optionally substituted with hydroxyl, halo or amino
(e) —$C_{1-4}$alkyl optionally substituted with hydroxyl or CN,
(f) —$C_{1-2}$alkyl-$C_{3-6}$cycloalkyl optionally substituted with hydroxy,
(h) —S(O)$_n$$C_{1-4}$alkyl wherein n is 0, 1 or 2,
(i) —S(O)$_n$NR$^6$R$^7$,
(j) —C(O)—NR$^{10}$R$^{11}$,
(k) HET$^4$,
(l) aryl, and
wherein choices (k) and (l) are each optionally mono or di-substituted with substituents selected from
(1) halo,
(2) —CN,
(3) —OH,
(4) —$C_{1-4}$alkyl optionally substituted with hydroxy, halo or cyano,
(5) —CF$_3$,
(6) —OC$_{1-4}$alkyl optionally substituted with hydroxyl or halo,
(7) —C(O)OH,
(8) —C(O)O—$C_{1-3}$alkyl, and
(9) —C(O)—NR$_{19}$R$_{20}$,
wherein R$^6$, R$^7$, R$^{10}$, R$^{11}$, R$^{19}$ and R$^{20}$, are each independently selected from H and $C_{1-4}$alkyl, or
R$^6$ and R$^7$ or R$^{10}$ and R$^{11}$ or R$^{19}$ and R$^{20}$ are joined together so that together with the atoms to which they are attached there is formed a 5 membered heterocyclic ring of 4 to 7 atoms, said ring containing 1, 2, 3 or 4 heteroatoms selected from N, O and S, said ring being optionally mono or di-substituted with substituents independently selected from halo, hydroxyl, $C_{1-4}$alkyl, —C(O)—$C_{1-4}$alkyl and —S(O)n$C_{1-4}$alkyl;
R$^2$ is selected from the group consisting of:
(1) aryl,
(2) HET$^3$,
(3) —$C_{1-6}$alkyl, and
(4) —$C^{3-6}$ cycloalkyl
wherein choice (1), (2), (3), and (4) is optionally mono or di-substituted with substituents independently selected from the group consisting of (a) halo,
(b) —CN,
(c) —OH,
(d) -hydroxy $C_{1-4}$alkyl,
(e) $C_{1-4}$alkyl,
(f) —$C_{1-4}$haloalkyl, and
(g) —OC$_{1-4}$alkyl, optionally substituted with halo or hydroxyl; and
R$^3$ is selected from the group consisting of:
(1) aryl, and
(2) HET$^5$,
wherein choice (1) and (2) are each optionally mono or di-substituted with substituents independently selected from the group consisting of
(a) halo,
(b) —$C_{3-6}$cycloalkyl,
(c) —$C_{1-4}$ alkyl,
(d) —OC$_{1-4}$ alkyl,
(e) mono, di or tri-halo $C_{1-4}$ alkyl, and
(f) mono, di or tri-halo —OC$_{1-4}$ alkyl.
Within this genus there is a sub-genus wherein
R$^1$ is selected from the group consisting of:
(1) phenyl,
(2) pyridinyl,
(3) pyrimidinyl,
(4) pyrazinyl, and
(5) pyridazinyl,
optionally mono or di-substituted with substituents R$^4$ and R$^5$, which are independently selected from the group consisting of
(a) —$C_{1-4}$alkyl optionally substituted with hydroxy,
(b) —S(O)$_n$$C_{1-4}$alkyl,
(c) —C(O)—NR$^{10}$R$^{11}$,
(d) HET$^4$, and
(e) halo,
wherein choice (d) is optionally mono or di-substituted with substituents selected from:
(1) halo,
(2) —CN,
(3) —OH,
(4) —$C_{1-4}$alkyl optionally substituted with hydroxy, halo or cyano,
(5) —CF$_3$,
(6) —OC$_{1-4}$alkyl optionally substituted with hydroxyl or halo,
(7) —C(O)OH,
(8) —C(O)O—$C_{1-3}$alkyl, and
(9) —C(O)—NR$^{19}$R$^{20}$,
wherein R$^{10}$, R$^{11}$, R$^{19}$ and R$^{20}$ are each independently selected from H and $C_{1-4}$alkyl, or R$^{10}$ and R$^{11}$ or R$^{19}$ and R$^{20}$ are joined together so that together with the atoms to which they are attached there is formed a 5 membered heterocyclic ring of 4 to 7 atoms, said ring containing 1, 2, 3 or 4 heteroatoms selected from N, O and S, said ring being optionally mono or di-substituted with substituents independently selected from halo, hydroxyl, $C_{1-4}$alkyl, —C(O)—$C_{1-4}$ alkyl and —S(O)n$C_{1-4}$alkyl;
R$^2$ is selected from the group consisting of:
(1) phenyl,
(2) pyridinyl,
(3) pyridazinyl,
(4) pyrimidinyl,
(5) pyrizinyl,
(5) thiazolyl,
(6) oxazolyl, and
(7) pyrazolyl, wherein choice (1), (2), (3), (4), (5), (6) and (7) are each optionally mono or di-substituted with halo, $OC_{1-4}$alkyl optionally substituted with halogen, —$C_{1-4}$haloalkyl, hydroxyl and CN; and $R^3$ is selected from the group consisting of:
(1) phenyl,
(2) pyrimidinyl,
(3) pyridinyl,
wherein choices (1), (2) and (3) are each optionally mono or di-substituted with halo, halo$C_{1-4}$alkyl, or —$OC_{1-4}$alkyl optionally substituted with halo.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

The invention is described using the following definitions unless otherwise indicated.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "alkylthio" means alkylthio groups having the indicated number of carbon atoms of a straight, branched or cyclic configuration. $C_{1-6}$alkylthio, for example, includes methylthio, propylthio, isopropylthio, and the like.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes propynyl, 1-methylethynyl, butyryl and the like.

The term "cycloalkyl" means mono-, bi- or tri-cyclic structures, optionally combined with linear or branched structures, the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

The term "aryl" is defined as a mono- or bi-cyclic aromatic ring system and includes, for example, phenyl, naphthyl, and the like.

The term "aralkyl" means an alkyl group as defined above of 1 to 6 carbon atoms with an aryl group as defined above substituted for one of the alkyl hydrogen atoms, for example, benzyl and the like.

The term "aryloxy" means an aryl group as defined above attached to a molecule by an oxygen atom (aryl-O) and includes, for example, phenoxy, naphthoxy and the like.

The term "aralkoxy" means an aralkyl group as defined above attached to a molecule by an oxygen atom (aralkyl-O) and includes, for example, benzyloxy, and the like.

The term "arylthio" is defined as an aryl group as defined above attached to a molecule by a sulfur atom (aryl-S) and includes, for example, thiophenyoxy, thionaphthoxy and the like.

The term "aroyl" means an aryl group as defined above attached to a molecule by an carbonyl group (aryl-C(O)—) and includes, for example, benzoyl, naphthoyl and the like.

The term "aroyloxy" means an aroyl group as defined above attached to a molecule by an oxygen atom (aroyl-O) and includes, for example, benzoyloxy or benzoxy, naphthoyloxy and the like.

The term "HET", such as in "$HET^1$", "$HET^2$", "$HET^3$", "$HET^4$", and "$HET^5$" is defined as a 5- to 10-membered aromatic, partially aromatic or non-aromatic mono- or bicyclic ring, containing 1-4 heteroatoms selected from O, S and N, and optionally substituted with 1-2 oxo groups. Where applicable, the Het group shall be defined to include the N-oxide. Preferably, "HET" is a 5- or 6-membered aromatic or non-aromatic monocyelic ring containing 1-3 heteroatoms selected from O, S and N, for example, pyridine, pyrimidine, pyridazine, furan, thiophene, thiazole, oxazole, isooxazole and the like, or HET is a 9- or 10-membered aromatic or partially aromatic bicyclic ring containing 1-3 heteroatoms selected from O, S, and N, for example, benzofuran, benzothiophene, indole, pyranopyrrole, benzopyran, quionoline, benzocyclohexyl, naphtyridine and the like. "HET" also includes the following: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

For all of the above definitions, each reference to a group is independent of all other references to the same group when referred to in the Specification. For example, if both $R^1$ and $R^2$ are HET, the definitions of HET are independent of each other and $R^1$ and $R^2$ may be different HET groups, for example furan and thiophene.

The ability of the compounds of Formula I to selectively inhibit FAAH makes them useful for treating, preventing or reversing the progression of a variety of inflammatory and non-inflammatory diseases and conditions.

Diseases, disorders, syndromes and/or conditions, that would benefit from inhibition of FAAH enzymatic activity include, for example, Alzheimer's Disease, schizophrenia, depression, alcoholism, addiction, suicide, Parkinson's disease, Huntington's disease, stroke, emesis, miscarriage, embryo implantation, endotoxic shock, liver cirrhosis, atherosclerosis, cancer, traumatic head injury, glaucoma, and bone cement implantation syndrome.

Other diseases, disorders, syndromes and/or conditions that would benefit from inhibition of FAAH activity, include, for example, multiple sclerosis, retinitis, amyotrophic lateral sclerosis, immunodeficiency virus-induced encephalitis, attention-deficit hyperactivity disorder, pain, nociceptive pain, neuropathic pain, inflammatory pain, noninflammatory pain, painful hemorrhagic cystitis, obesity, hyperlipidemia, metabolic disorders, feeding and fasting, alteration of appetite, stress, memory, aging, hypertension, septic shock, cardiogenic shock, intestinal inflammation and motility, irritable bowel syndrome, colitis, diarrhea, ileitis, ischemia, cerebral ischemia, hepatic ischemia, myocardial infarction, cerebral excitotoxicity, seizures, febrile seizures, neurotoxicity, neuropathies, sleep, induction of sleep, prolongation of sleep, insomnia, and inflammatory diseases. Neurological and psychological disorders that would benefit from inhibition of FAAH activity include, for example, pain, depression, anxiety, generalized anxiety disorder (GAD), obsessive compulsive disorders, stress, stress urinary incontinence, attention deficit hyperactivity disorders, schizophrenia, psychosis, Parkinson's disease, muscle spasticity, epilepsy, diskenesia, seizure disorders, jet lag, and insomnia.

FAAH inhibitors can also be used in the treatment of a variety of metabolic syndromes, diseases, disorders and/or conditions, including but not limited to, insulin resistance syndrome, diabetes, hyperlipidemia, fatty liver disease, obesity, atherosclerosis and arteriosclerosis. FAAH inhibitors are useful in the treatment of a variety of painful syndromes, diseases, disorders and/or conditions, including but not limited to those characterized by non-inflammatory pain, inflammatory pain, peripheral neuropathic pain, central pain, deafferentiation pain, chronic nociceptive pain, stimulus of nociceptive receptors, phantom and transient acute pain.

Inhibition of FAAH activity can also be used in the treatment of a variety of conditions involving inflammation. These conditions include, but are not limited to arthritis (such as rheumatoid arthritis, shoulder tendonitis or bursitis, gouty arthritis, and aolymyalgia rheumatica), organ-specific inflammatory diseases (such as thyroiditis, hepatitis, inflammatory bowel diseases), asthma, other autoimmune diseases (such as multiple sclerosis), chronic obstructive pulmonary disease (COPD), allergic rhinitis, and cardiovascular diseases.

In some cases, FAAH inhibitors are useful in preventing neurodegeneration or for neuroprotection.

In addition, it has been shown that when FAAH activity is reduced or absent, one of its substrates, anandamide, acts as a substrate for COX-2, which converts anandamide to prostamides (Weber et al J Lipid. Res. 2004; 45:757). Concentrations of certain prostamides may be elevated in the presence of a FAAH inhibitor. Certain prostamides are associated with reduced intraocular pressure and ocular hypotensivity. Thus, in one embodiment, FAAH inhibitors may be useful for treating glaucoma.

In some embodiments, FAAH inhibitors can be used to treat or reduce the risk of EMDs, which include, but are not limited to, obesity, appetite disorders, overweight, cellulite, Type I and Type II diabetes, hyperglycemia, dyslipidemia, steatohepatitis, liver steatosis, non-alcoholic steatohepatitis, Syndrome X, insulin resistance, diabetic dyslipidemia, anorexia, bulimia, anorexia nervosa, hyperlipidemia, hypertriglyceridemia, atherosclerosis, arteriosclerosis, inflammatory disorders or conditions, Alzheimer's disease, Crohn's disease, vascular inflammation, inflammatory bowel disorders, rheumatoid arthritis, asthma, thrombosis, or cachexia.

In other embodiments, FAAH inhibitors can be used to treat or reduce the risk of insulin resistance syndrome and diabetes, i.e., both primary essential diabetes such as Type I Diabetes or Type II Diabetes and secondary nonessential diabetes. Administering a composition containing a therapeutically effective amount of an in vivo FAAH inhibitor reduces the severity of a symptom of diabetes or the risk of developing a symptom of diabetes, such as atherosclerosis, hypertension, hyperlipidemia, liver steatosis, nephropathy, neuropathy, retinopathy, foot ulceration, or cataracts.

In another embodiment, FAAH inhibitors can be used to treat food abuse behaviors, especially those liable to cause excess weight, e.g., bulimia, appetite for sugars or fats, and non-insulin-dependent diabetes.

In some embodiments, FAAH inhibitors can be used to treat a subject suffering from an EMD and also suffers from a depressive disorder or from an anxiety disorder. Preferably, the subject is diagnosed as suffering from the depressive or psychiatric disorder prior to administration of the FAAH inhibitor composition. Thus, a dose of a FAAH inhibitor that is therapeutically effective for both the EMD and the depressive or anxiety disorder is administered to the subject.

Preferably, the subject to be treated is human. However, the methods can also be used to treat non-human mammals. Animal models of EMDs such as those described in, e.g., U.S. Pat. No. 6,946,491 are particularly useful.

FAAH inhibitor compositions can also be used to decrease body-weight in individuals wishing to decrease their body weight for cosmetic, but not necessarily medical considerations.

A FAAH inhibitor composition can be administered in combination with a drug for lowering circulating cholesterol levels (e.g., statins, niacin, fibric acid derivatives, or bile acid binding resins). FAAH inhibitor compositions can also be used in combination with a weight loss drug, e.g., orlistat or an appetite suppressant such as diethylpropion, mazindole, orlistat, phendimetrazine, phentermine, or sibutramine.

The term "treating" encompasses not only treating a patient to relieve the patient of the signs and symptoms of the disease or condition but also prophylactically treating an asymptomatic patient to prevent the onset of the disease or condition or preventing, slowing or reversing the progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The term "treating" encompasses not only treating a patient to relieve the patient of the signs and symptoms of the disease or condition but also prophylactically treating an asymptomatic patient to prevent the onset of the disease or condition or preventing, slowing or reversing the progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The following abbreviations have the indicated meanings:
AIBN=2,2'-azobisisobutyronitrile
B.P.=benzoyl peroxide
Bn=benzyl
$CCl_4$=carbon tetrachloride
D=—$O(CH_2)_3O$—
DAST=diethylamine sulfur trifluoride
DCC=dicyclohexyl carbodiimide
DCI=1-(3-dimethylaminopropyl)-3-ethyl carbodiimide
DEAD=diethyl azodicarboxylate
DIBAL=diisobutyl aluminum hydride
DME=ethylene glycol dimethylether
DMAP=4-(dimethylamino)pyridine
DMF=N,N-dimethylformamide
DMSO=dimethyl sulfoxide
$Et_3N$=triethylamine
LDA=lithium diisopropylamide
m-CPBA=metachloroperbenzoic acid
NBS=N-bromosuccinimide
NSAID=non-steroidal anti-inflammatory drug
PCC=pyridinium chlorochromate
PDC=pyridinium dichromate
Ph=phenyl
1,2-Ph=1,2-benzenediyl
Pyr=pyridinediyl
Qn=7-chloroquinolin-2-yl
$R^s$=—$CH_2SCH_2CH_2Ph$
r.t.=room temperature
rac.=racemic
THF=tetrahydrofuran
THP=tetrahydropyran-2-yl
Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glutamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

The magnitude of prophylactic or therapeutic dose of a compound of Formula I will, of course, vary with the nature and the severity of the condition to be treated and with the particular compound of Formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for oral administration to humans may contain from about 0.5 mg to about 5 g of active agent compounded with an appropriate and convenient amount of carrier material which may vary from about 5 to about 95 percent of the total composition. Dosage unit forms will generally contain from about 1 mg to about 2 g of an active ingredient, typically 25 mg, 50 mg, 100 mg, 200 mg, 300 mg, 400 mg, 500 mg, 600 mg, 800 mg, or 1000 mg.

For the treatment of FAAH mediated diseases the compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous, intravenous, intramuscular, intrastemal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, solutions, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing a compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Assays

The following assays illustrate the utility of the invention:

The compounds of the invention underwent pharmacological evaluations to determine their inhibitory effect on the enzyme FAAH (Fatty Acid Amide Hydrolase).

To assist in assay development stable cell lines for human, murine and rat full length FAAH were developed. Human FAAH cDNA (Accession No: NM_001441.1) was purchased from Origene (Rockville, Md.). The full length FAAH was subcloned into the mammalian expression vector, pcDEF.neo, using XbaI and EcoRI restriction sites and used for stable cell line generation.

| Construct | Primer | Sequence |
|---|---|---|
| Full length rodent FAAH | 1 | CAAGGTACCGCCACCATGGTGCTGAGCGA AGTGTGG (SEQ ID NO: 1) |
| Full length murine FAAH | 2 | CCGGAATTCTCAAGATGGCCGCTTTTCAGG (SEQ ID NO: 2) |
| Full length rat FAAH | 3 | CCGGAATTCTCACGATGGCTGCTTTTGAGG (SEQ ID NO: 3) |

Murine (accession number NM_010173) and Rat FAAH (accession number NM_024132) was amplified by reverse transcriptase polymerase chain reaction (RT-PCR) from brain cDNA (BD Biosciences, San Jose, Calif.) using primers 1 and 2 or primers 1 and 3 respectively (see Table). The resulting PCR product was ligated into pCR4 TOPO and DNA sequence confirmed. The full length murine FAAH was subcloned into the mammalian expression vector, pcDEFneo using either EcoRI (murine) or KpnI and EcoRI (rat) restriction sites. Chinese hamster ovary cells (CHO) were transfected following manufacturers protocol (AMAXA). Forty eight hours post transfection, cells were trypsinized and transferred to 96 well plates in Iscove's DMEM media supplemented with 2 mM Glutamine, 10% fetal calf serum, 1 mg/ml geneticin and HT Supplement (0.1 mM sodium hypoxanthine, 0.016 mM thymidine) in order to isolate single clones. Following selection in geneticin, individual clones were selected and FAAH activity was assessed using a whole cell fluorescent anandamide assay, modified from Ramarao et al (2005). Following removal of tissue culture media cells were dislodged following addition of Cellstripper (Mediatech, Inc. Manassas, Va.) and transferred to 96 well black clear bottom assay plate, centrifuged at 1,000 rpm for 3 mins and media removed and replaced with assay buffer (50 mM Tris pH8.0, 1 mM EDTA, 0.1% fatty acid free BSA). The reaction was initiated by addition of fluorescent substrate, AMC Arachidonoyl Amide (Cayman Chemical, Ann Arbor, Mich.) to 1 μM and reaction allowed to proceed for 2 hours at room temperature. Release of fluorescence was monitored in a CytoFluor Multiplate Reader. Cells expressing the highest amount of FAAH activity were selected for study with FAAH inhibitors.

Preparation of Lysate and Microsomes

CHO cells expressing FAAH were used to prepare either crude cell lysate or microsome fractions. To harvest cells, tissue culture media was decanted, the monolayer washed three times with $Ca^{++}Mg^{++}$ free PBS and cells recovered after 15 min in enzyme free dissociation media (Millipore Corp, Billerica, Mass.). Cells were collected by centrifuging at 2000 rpm for 15 min. and the cell pellet re-suspended with 50 mM HEPES (pH 7.4) containing 1 mM EDTA and the protease inhibitors aprotinin (1 mg/ml) and leupeptin (100 μM). The suspension was sonicated at 4° C. and the cell lysate recovered after centrifuging at 12,000×g (14,600 rpm, SS34 rotor) for 20 min at 4° C. to form a crude pellet of cell debris, nuclei, peroxisomes, lysosomes, and mitochondria; the supernatant or cell lysate was used for FAAH enzyme assay. In some cases, microsomes fractions enriched in FAAH were prepared by centrifuging the cell lysate further at 27,000 rpm (100,000×g) in SW28 rotor for 50 minutes at 4° C. The pellet containing FAAH-enriched microsomes was re-suspend in 50 mM HEPES, (pH 7,4) 1 mM EDTA, and any remaining DNA sheared by passage of material through a 23 gauge needle and aliquots of enzyme were store at −80° C. prior to use.

FAAH Assays

Several assays have been used to demonstrate the inhibitory activity. Enzyme activity was demonstrated in a radioenzymatic test based on measuring the product of hydrolysis (ethanolamine [$^3$H]) of anandamide [ethanolamine 1-.sup.3H] (American Radiolabeled Chemicals; 1 mCi/ml) with FAAH (Life Sciences (1995), 56, 1999-2005 and Journal of Pharmacology and Experimented Therapeutics (1997), 283, 729-734), Analytical. Biochemistry (2003), 318, 270-5. In addition, routine assays were performed monitoring hydrolysis of arachidonyl-7-amino-4-methylcoumarin amide (AAMCA) by following increase in fluorescence upon release of 7-amino 4-methyl coumarin ($\lambda_{EX}$=355 nm, $\lambda_{EM}$=460 nm). Analytical. Biochemistry (2005). 343, 143-51

Assays are performed on either cell lysate or microsome fractions prepared as described or in whole cell format employing either the fluorescent substrate AAMCA (Cayman chemical, Ann Arbor, Mich.) or $^3$H-anandmaide ([ETHANOLAMINE-1-3H] American Radiolabeled Chemicals; 1 mCi/ml). The cell lysate or microsome assay is performed in Costar black wall, clear bottom plates by adding FAAH-_CHO (whole cell, cell lysate or microsome) in assay buffer (50 mM Phosphate, pH 8.0, 1 mM EDTA, 200 mM KCl, 0.2% glycerol, 0.1% fatty acid free BSA) to each well, followed by either DMSO or compound and allowed to incubate at 22-25° C. for fifteen minutes. AAMCA substrate was used to achieve a final concentration of 1 μM and reaction allowed to proceed at room temperature for 1-3 hours. Fluorescent release as a measure of FAAH activity was monitored by reading the plate in a CytoFluor Multiplate Reader (Ex: 360/40 nM; Em: 460/40 nM). Whole cell assay is conducted with cells harvested after rinsing tissue culture flasks three times with $Ca^{++}Mg^{++}$ free PBS, incubating for 10 min in Enzyme free dissociation media and centrifuging for 5 minutes at 1,000 rpm in table top centrifuge. Cells are resuspended in assay buffer at desired cell number in ($4 \times 10^4$ cells/assay in 96-well format; $1 \times 10^4$ cells/assay in 384-well format) and assayed as described.

Alternatively, assays are performed using anandamide [ethanolamine 1-.sup.3H] (specific activity of 10 Ci/mmol) diluted with cold anandamide to achieve a final assay concentration of 1 μM anandamide (~50,000 cpm). Enzyme (CHO cell lysate, brain or liver homogenate) is incubated in assay buffer (50 mM Phosphate, pH 8.0, 1 mM EDTA, 200 mM KCl, 0.2% glycerol, 0.1% fatty acid free BSA) with inhibitor at 25° C. for 30 minutes. The reaction was terminated by addition of 2 volumes of chloroform:methanol (1:1) and mixed by vortexing. Following a centrifugation step, 2000 rpm for 10 min. at room temperature, the aqueous phase containing the released ³H-ethanolamide was recovered and quantitated by liquid scintillation as a reflection of FAAH enzyme activity.

Ramarao M. K., et al. A fluorescence-based assay for fatty acid amide hydrolase compatible with high-throughput screening. Anal. Biochem. 343:143-51 (2005)

Wilson S. J., et l. A high-throughput-compatible assay for determining the activity of fatty acid amide hydrolase. Anal Biochem. 318:270-5 (2003).

| Examples | MOLSTRUCTURE | Human Lysate | Human whole cell | Rat Whole cell |
|---|---|---|---|---|
| Ex 13 | | 945.7 | 3000 | 701.7 |
| Ex 14 | | 26.5 | 106.7 | 145.9 |
| Ex 2 | | 21.16 | 84.83 | 30.07 |
| Ex 29 | | 74.39 | 480.4 | 104.8 |

-continued

| Examples | MOLSTRUCTURE | Human Lysate | Human whole cell | Rat Whole cell |
|---|---|---|---|---|
| Ex 3 | (4-chlorophenylthio / 1-methyl-2-phenyl-1H-imidazole-4-yl benzonitrile, trifluoroacetate salt) | 370.4 | | |
| Ex 33 | (4-chlorophenylthio / 1-methyl-1H-imidazole-4-yl benzonitrile) | 363.2 | 2980 | 1208 |
| Ex 36 | (5-chloropyridin-2-ylthio / 1-methyl-2-(pyridin-2-yl)-1H-imidazole-4-yl phenyl-1,3,4-oxadiazole) | 26.94 | 48.6 | 63.4 |
| Ex 57 | (4-chlorophenylthio / 1-methyl-2-(pyridin-2-yl)-1H-imidazole-4-yl phenyl-2,2-difluoro-1-hydroxyethyl) | 21.39 | 67.77 | 59.63 |

| Examples | MOLSTRUCTURE | Human Lysate | Human whole cell | Rat Whole cell |
|---|---|---|---|---|
| Ex 66 | | 16.58 | 52.16 | 31.91 |
| Ex 98 | | 33.74 | 1000 | 870.5 |

Preparation of the Compounds of the Invention

The compounds of the present invention can be prepared according to the procedures denoted in the following reaction Schemes and Examples or modifications thereof using readily available starting materials, reagents, and conventional procedures thereof well-known to a practitioner of ordinary skill in the art of synthetic organic chemistry. Specific definitions of variables in the Schemes are given for illustrative purposes only and are not intended to limit the procedures described.

Intermediate 1

5-Chloropyridine-2-thiol

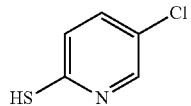

2,5-Dichloropyridine (5.0 g) and thiourea (2.57 g) were suspended in 50 mL of EtOH and the mixture was heated at 95° C. for 22 h. The reaction mixture was cooled, and was slowly added a solution of 2.8 g of KOH in 5.0 mL of water. The solution was heated at 95° C. for 2 h, cooled, poured into 100 mL of 0.5 N NaOH, made acidic with acetic acid. The product was extracted with dichloromethane, washed with water, dried over $MgSO_4$, and filtered. The organic layer was concentrated to give 2.3 g of the title compound. 1H NMR (500 MHz, ($CD_3OD$): 7.78 (s, 1H), 7.44 (d, 1H), 7.39 (d, 1H), 4.39 (s, 1H). LCMS: m/z 146.0 (M+H)+.

Intermediate 2

4-(Bromoacetyl)-2-fluorobenzonitrile

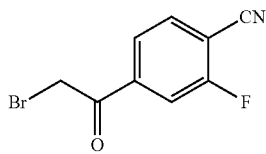 [SMILES: N#Cc1ccc(C(=O)CBr)cc1F]

Step 1. A mixture of (1-ethoxyvinyl)tributyltin (27.1 g), 4-bromo-2-fluorobenzonitrile (15 g), and $PdCl_2(PPh_3)_2$ (1 g) in 50 mL of toluene under nitrogen was heated at 100° C. overnight. The reaction mixture was diluted with EtOAc, washed with $H_2O$, brine, dried over $MgSO_4$, filtered. To the organic solution was added KF/Celite (50% wt from Aldrich) and stirred for 1.5 h. Upon filtration and concentration, the residue was taken up in 75 mL of EtOH and 42 mL of 2 N HCl, stirred at rt for 1 h to hydrolyze the vinyl ethyl ether to the desired methyl ketone. The filtrate was concentrated, and the residue was taken up in EtOAc, washed with $H_2O$, aq $NaHCO_3$, brine, dried $MgSO_4$, and filtered. The filtrate was concentrated to give 11.0 g of crude product that was used as is in next step without further purification.

Step 2. The crude product of Step 1 was dissolved in 50 mL of chloroform and cooled to 0° C., to which was added catalytic amount of $AlCl_3$ and 2.7 mL of bromine in 25 mL of chloroform. The addition of bromine lasted 1 h to keep the reaction solution at 0° C. After stirring at 0° C. overnight, chloroform was removed under reduced pressure and the residue was loaded onto a silica column. Eluting with 5-10% EtOAc in hexanes provided the title compound. LCMS: m/z 242 (M+H)+.

Intermediate 3

4-(Bromoacetyl)-2-chlorobenzonitrile

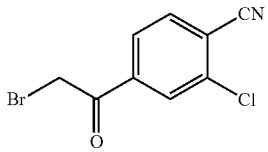 [SMILES: N#Cc1ccc(C(=O)CBr)cc1Cl]

The title compound was prepared starting with 4-bromo-2-chlorobenzonitrile and following the same procedure as described for intermediate 2. LCMS: m/z 258 (M+H)+.

Intermediate 4

2-Bromo-1-(6-bromopyridin-3-yl)ethanone

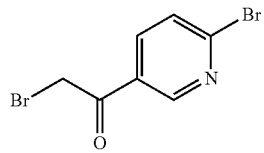

The title compound was prepared starting with 1-(6-bromopyridin-3-yl)ethanone and following the same procedure as described in the step 2 for intermediate 2. LCMS: m/z 277.9 (M+H)+.

Intermediate 5

2-Bromo-1-(5-cyanopyridin-2-yl)ethanone

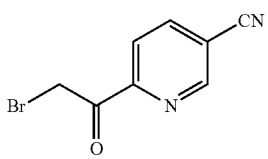 [SMILES: N#Cc1ccc(C(=O)CBr)nc1]

The title compound was prepared starting with 1-(5-cyanopyridin-2-yl)ethanone and following the same procedure as described in the step 2 for intermediate 2. LCMS: m/z 225 (M+H)+.

Intermediate 6

Methyl 4-(bromoacetyl)benzoate

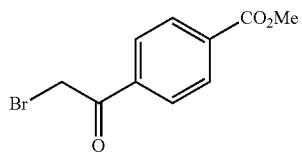 [SMILES: COC(=O)c1ccc(C(=O)CBr)cc1]

4-(Bromoacetyl)benzoic acid (10 g, 41.3 mmol) was dissolved in 75 mL of MeOH and 75 mL of methylene chloride. Trimethylsilyl diazomethane (2.0 M in ether) was slowly added at 0° C. until a yellow color persisted. The volatiles were evaporated to give the title compound. 1H NMR (500 MHz, (CD$_3$OD): 8.18 (d, 2H), 8.16 (d, 2H), 4.68 (s, 2H), 3.96 (s, 3H). LCMS: m/z 258 (M+H)+.

Intermediate 7

2-{5-Iodo-1-methyl-4-[4-(1,3,4-oxadiazol-2-yl)phenyl]-1H-imidazol-2-yl}pyridine

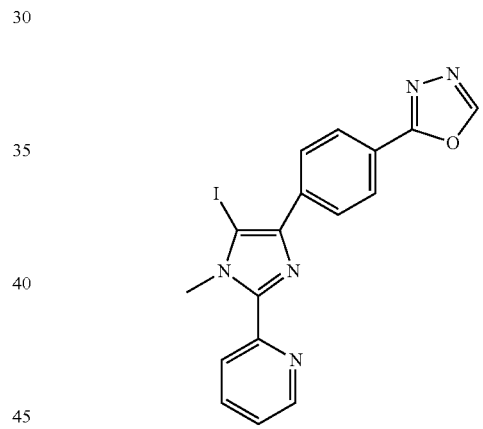

Step 1. 2-Pyridinecarboximidamide HCl salt (11.7 g, 74.3 mmol) and sodium bicarbonate (13.7 g, 163 mmol) were suspended in 100 mL of THF and 30 mL of water. The suspension was heated to reflux, to which was slowly added methyl 4-(bromoacetyl)benzoate (Intermediate 6, 21 g, 82 mmol) in 70 mL of THF over 4 h. The reflux was continued overnight. The reaction mixture was cooled to rt, partially concentrated, and cooled with an ice-water bath. The precipitate was collected by filtration, rinsed with two 50-mL portions of water, and air-dried to provide the desired product. LCMS: 280 [M+1].

Step 2. Methyl 4-(2-pyridin-2-yl-1H-imidazol-4-yl)benzoate (from Step 1, 19.55 g, 70 mmol) was dissolve in THF (160 mL), to which was added Cs$_2$CO$_3$ (29.6 g, 91 mmol) at 0° C. After stirring for 5 min, MeI (11 mL, 175 mmol) was added. After stirring overnight at rt, the reaction was quenched with aq NH$_4$Cl. The product was extracted with EtOAc and the organic layer was washed with water, brine, dried over MgSO$_4$, filtered, and concentrated. The residue was subject to silica column chromatography (0-20% EtOAc in hexanes) to give 12.5 g of methyl 4-(1-methyl-2-pyridin-2-yl-1H-imidazol-4-yl)benzoate. LCMS: m/z 294 (M+H)+.

Step 3. Methyl 4-(1-methyl-2-pyridin-2-yl-1H-imidazol-4-yl)benzoate (12.5 g, 42.6 mmol) was dissolved in methylene chloride (120 mL), to which was added NIS (10.6 g, 47 mmol) and 0.5 mL of TFA. After stirring for 5 min, the reaction was diluted with 120 mL of methylene chloride and quenched with aq NaHCO$_3$. The organic layer was separated, washed with aq Na$_2$S$_2$O$_3$, water, brine, dried over MgSO$_4$, filtered, and concentrated to give 16.3 g of methyl 4-(5-iodo-1-methyl-2-pyridin-2-yl-1H-imidazol-4-yl)benzoate. 1H NMR (500 MHz, (CDCl$_3$): 8.63 (m, 1H), 8.24 (d, 1H), 8.18 (s, 4H), 7.83 (m, 1H), 7.31 (m, 1H), 4.22 (s, 3H), 3.96 (s, 3H). LCMS: [M+1]=420.

Step 4. Methyl 4-(5-iodo-1-methyl-2-pyridin-2-yl-1H-imidazol-4-yl)benzoate (Step 3, 2 g, 1.9 mmol) was suspended in 10 mL of EtOH and 3 mL of anhydrous hydrazine, and heated at reflux for 2 h. After the reaction was cooled to rt, the solid product was filtered, washed with hexanes, and air-dried to give 750 mg of 4-(5-iodo-1-methyl-2-pyridin-2-yl-1H-imidazol-4-yl)benzohydrazide. LCMS: [M+1]=420.

Step 5. 4-(5-Iodo-1-methyl-2-pyridin-2-yl-1H-imidazol-4-yl)benzohydrazide (4.9 g, 12 mmol) was suspended in 60 mL of triethyl orthoformate, to which was added 1 mL of TFA. The suspension was heated at 130° C. The reaction was cooled to rt, and the precipitate was collected, washed with hexanes and dried to give 4.8 g of the title compound. 1H NMR (500 MHz, (CDCl$_3$): 8.62 (m, 1H), 8.57 (s, 1H), 8.11 (m, 1H), 8.09 (s, 4H), 7.82 (m, 1H), 7.32 (m, 1H), 4.13 (s, 3H). LCMS: [M+1]=430.

Example 1

4-{5-[(4-Chlorophenyl)thio]-2-phenyl-1H-imidazol-4-yl}benzonitrile

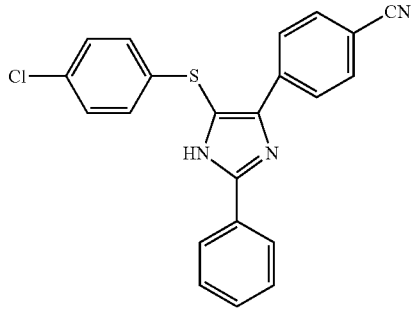 [SMILES: N#Cc1ccc(-c2nc(-c3ccccc3)[nH]c2Sc2ccc(Cl)cc2)cc1]

Step 1. Benzenecarboximidamide (2.9 g, 24 mmol), 4-bromoacetylbenzonitrile (5 g, 22 mmol), and sodium bicarbonate (1.8 g, 22 mmol) were suspended in 70 mL of THF and 10 mL of water and heated at reflux overnight. The reaction mixture was cooled rt, and partially concentrated. An additional 10 mL of water was added, and the resulting suspension was stirred at 50-60° C. for 30 min. The mixture was cooled with an ice-water bath and the precipitate was collected by filtration, rinsed with two 10-mL portions of water, and air-dried. The solid material was stirred with 15 mL of EtOAc and 15 mL of hexanes, and was again collected by filtration, and dried to give 4-(2-phenyl-1H-imidazol-4-yl)benzonitrile. LCMS: min [M+1]=246.

Step 2. The product of Step 1 (700 mg, 2.85 mmol) was dissolved in 10 mL of MeCN, to which was added NIS (770 mg, 3.42 mmol) and catalytic amount of TPA. After stirring at rt overnight, the reaction was diluted with EtOAc, washed with aq NaHCO$_3$, aq Na$_2$S$_2$O$_3$, water, and brine. The organic layer was dried over MgSO$_4$, filtered, and concentrated to give 770 mg of 4-(5-iodo-2-phenyl-1H-imidazol-4-yl)benzonitrile. LCMS: [M+1]=372.

Step 3. CuI (20 mg, 0.104 mmol), K$_2$CO$_3$ (573 mg, 4.15 mmol), the product of Step 2 (770 mg, 2.0 mmol), and 4-chlorobenzenethiol (330 mg, 2.2 mmol) were added to a flask, which was flushed with N$_2$. 2-Propanol (8 mL) and ethylene glycol (0.23 mL, 4.15 mmol) were added. The reaction mixture was heated at 80° C. for 24 h. Then the reaction was diluted with EtOAc, filtered, concentrated, and the residue was subject to silica column chromatography (5-25% EtOAc in hexanes) to give the title compound. 1H NMR (500 MHz, (CD$_3$OD): 8.08 (m, 1H), 8.01 (d, 2H), 7.78 (d, 2H), 7.47 (m, 4H), 7.24 (d, 2H), 7.17 (d, 2H). LCMS: m/z 388.0 (M+H)+.

Example 2

4-{5-[(4-Chlorophenyl)thio]-1-methyl-2-phenyl-1H-imidazol-4-yl}benzonitrile

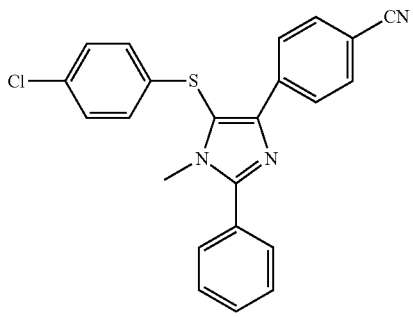 [SMILES: Cn1c(-c2ccccc2)nc(-c2ccc(C#N)cc2)c1Sc1ccc(Cl)cc1]

4-{5-[(4-Chlorophenyl)thio]-2-phenyl-1H-imidazol-4-yl}benzonitrile (Example 1, 222 mg, 0.57 mmol) was dissolve in THF (6 mL), to which was added NaH (60% wt, 27.5 mg, 0.687 mmol) at 0° C. After stirring for 5 min, MeI (0.05 mL, 0.86 mmol) was added. The reaction was stirred at 0° C. for 2 h, and then quenched with aq NH$_4$Cl to adjust the pH to 6-8. The product was extracted with EtOAc and the organic layer was washed with water, brine, dried over MgSO$_4$, filtered, and concentrated. The residue was subject to silica column chromatography (0-20% EtOAc in hexanes) to give the title compound as the major region isomer. 1H NMR (500 MHz, (CD$_3$OD): 8.18 (d, 2H), 7.77 (m, 2H), 7.76 (d, 2H), 7.68 (m, 3H), 7.34 (d, 2H), 7.09 (d, 2H), 3.70 (s, 3H). LCMS: m/z 402 (M+H)+. The minor region isomer was the title compound of Example 3.

Example 3

4-{4-[(4-chlorophenyl)thio]-1-methyl-2-phenyl-1H-imidazol-5-yl}benzonitrile

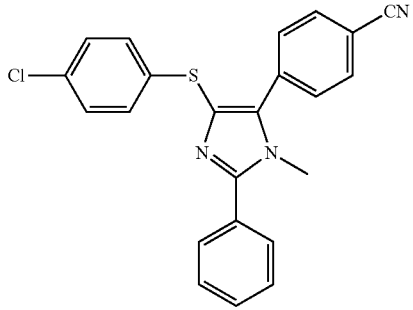 [SMILES: Cn1c(-c2ccccc2)nc(Sc2ccc(Cl)cc2)c1-c1ccc(C#N)cc1]

The title compound was prepared as the minor product in the reaction described in Example 2. 1H NMR (500 MHz, (CD₃OD): 7.97 (d, 2H), 7.80 (m, 2H), 7.68 (d, 2H), 7.63 (m, 3H), 7.33 (d, 2H), 7.22 (d, 2H), 3.73 (s, 3H). LCMS: m/z 402 (M+H)+.

The examples in Table 1 were prepared with the procedures described in Example 2, 3 using appropriate starting materials (amidine and α-bromoketone) shown in the table.

TABLE 1

| Example | Starting materials | Compound structure | LCMS Rt (min) | [M + 1] |
|---|---|---|---|---|
| 4 | | 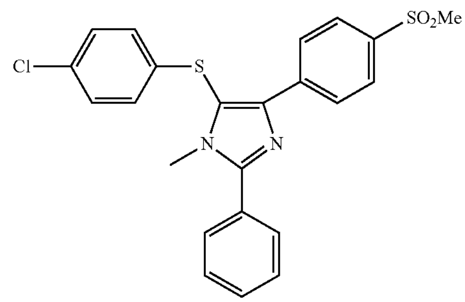 | 1.17 | 455 |
| 5 | | 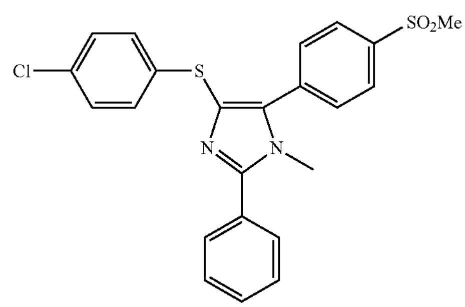 [SMILES: Cn1c(-c2ccccc2)nc(Sc2ccc(Cl)cc2)c1-c1ccc(S(C)(=O)=O)cc1] | 1.10 | 455 |
| 6 | | 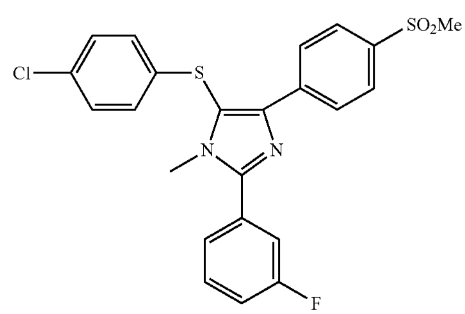 [SMILES: Cn1c(-c2cccc(F)c2)nc(-c2ccc(S(C)(=O)=O)cc2)c1Sc1ccc(Cl)cc1] | 1.22 | 473 |
| 7 | | 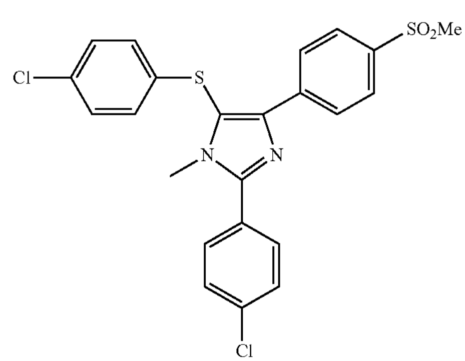 [SMILES: Cn1c(-c2ccc(Cl)cc2)nc(-c2ccc(S(C)(=O)=O)cc2)c1Sc1ccc(Cl)cc1] | 1.24 | 489 |

TABLE 1-continued
| Example | Starting materials | Compound structure | LCMS Rt (min) | [M + 1] |
|---|---|---|---|---|
| 8 | 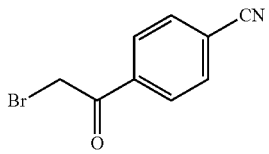 | 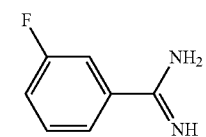 | 1.23 | 420 |
| 9 | 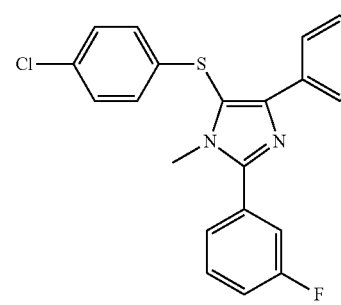 | 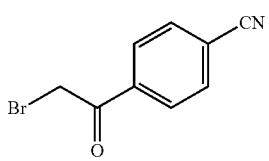 | 1.23 | 420 |
| 10 | 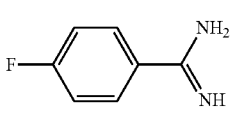 | 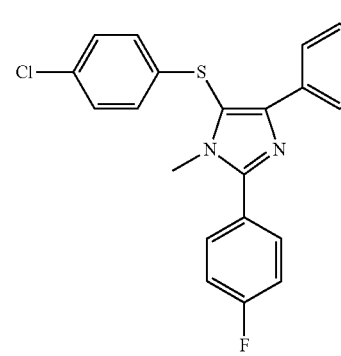 | 1.23 | 409 |
| 11 | 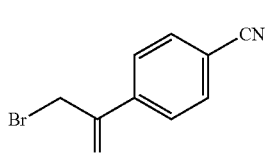 | 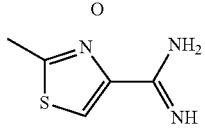 | 1.28 | 423 |
| 12 | Intermediate 3 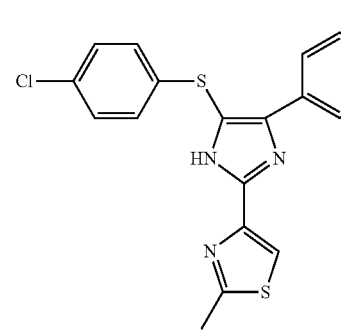 | 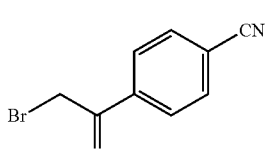 | 1.23 | 400 |

TABLE 1-continued
| Example | Starting materials | Compound structure | LCMS Rt (min) | [M + 1] |
|---|---|---|---|---|
| 13 | 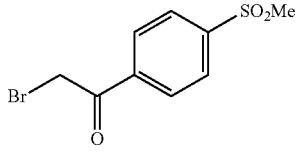 | 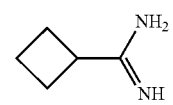 | 1.09 | 419 |
| 14 | 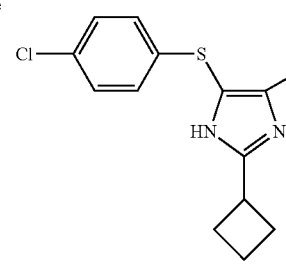 | 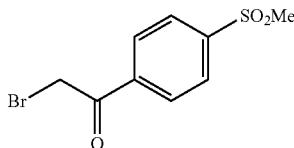 | 1.13 | 433 |
| 15 | 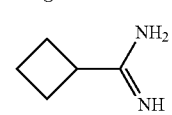 | 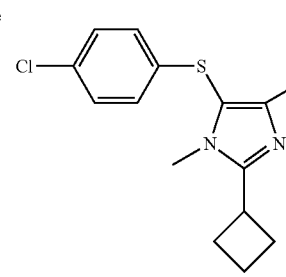 | 1.33 | 456 |
| 16 | 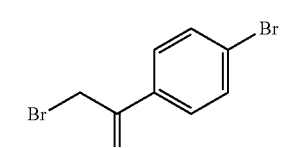 | 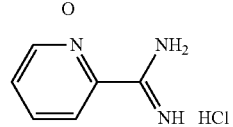 | 1.41 | 412 |
| 17 | 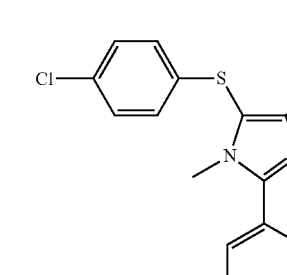 | 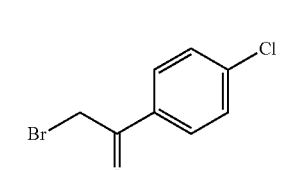 | 1.35 | 378 |

TABLE 1-continued

| Example | Starting materials | Compound structure | LCMS Rt (min) | [M + 1] |
|---------|-------------------|--------------------|--------------:|--------:|
| 18 | Intermediate 6; pyridine-2-carboxamidine · HCl | 4-[5-(4-chlorophenylthio)-1-methyl-2-(pyridin-2-yl)-1H-imidazol-4-yl]benzoic acid methyl ester | 1.25 | 436 |
| 19 | 2-bromo-1-(4-cyanophenyl)ethanone; pyrazine-2-carboxamidine | 4-[5-(4-chlorophenylthio)-1-methyl-2-(pyrazin-2-yl)-1H-imidazol-4-yl]benzonitrile | 1.31 | 404 |
| 20 | 2-bromo-1-(4-methylsulfonylphenyl)ethanone; pyrazine-2-carboxamidine | 5-(4-chlorophenylthio)-1-methyl-4-(4-methylsulfonylphenyl)-2-(pyrazin-2-yl)-1H-imidazole | 1.33 | 457 |
| 21 | 2-bromo-1-(4-methylsulfonylphenyl)ethanone; pyridine-3-carboxamidine | 5-(4-chlorophenylthio)-1-methyl-4-(4-methylsulfonylphenyl)-2-(pyridin-3-yl)-1H-imidazole | 1.20 | 456 |
| 22 | Intermediate 3; pyridine-2-carboxamidine · HCl | 4-[5-(4-chlorophenylthio)-1-methyl-2-(pyridin-2-yl)-1H-imidazol-4-yl]-2-chlorobenzonitrile | 1.47 | 437 |

TABLE 1-continued

| Example | Starting materials | Compound structure | LCMS Rt (min) | [M + 1] |
|---|---|---|---|---|
| 23 | | 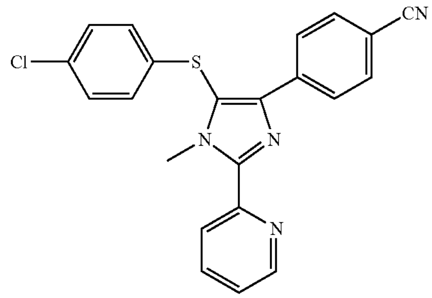 [SMILES: Cn1c(-c2ccccn2)nc(-c2ccc(C#N)cc2)c1Sc1ccc(Cl)cc1] | 1.26 | 403 |
| 24 | | 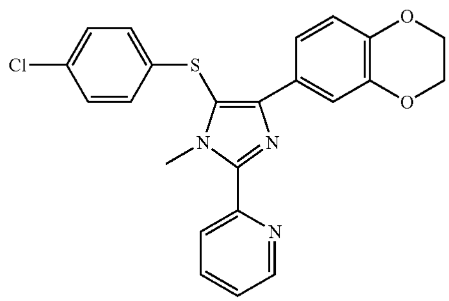 [SMILES: Cn1c(-c2ccccn2)nc(-c2ccc3c(c2)OCCO3)c1Sc1ccc(Cl)cc1] | 1.24 | 436 |
| 25 | | 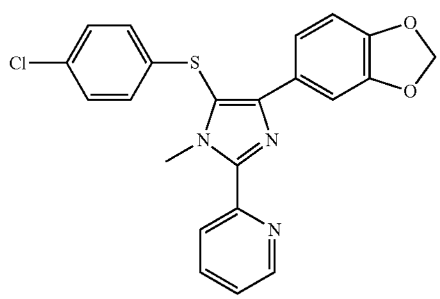 [SMILES: Cn1c(-c2ccccn2)nc(-c2ccc3c(c2)OCO3)c1Sc1ccc(Cl)cc1] | 1.19 | 422 |
| 26 | | 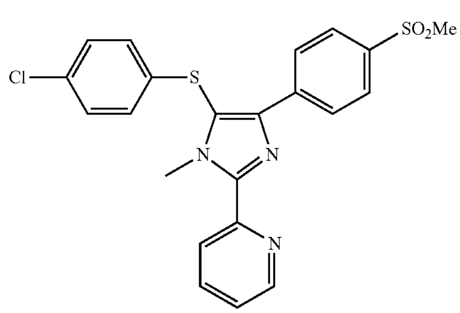 | 1.28 | 456 |

Example 27

5-[(4-Chlorophenyl)thio]-1,2-dimethyl-4-[4-(methylsulfonyl)phenyl]-1H-imidazole

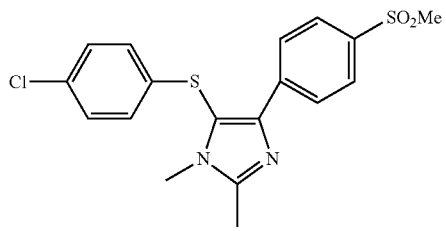 [SMILES: Cc1nc(-c2ccc(S(C)(=O)=O)cc2)c(Sc2ccc(Cl)cc2)n1C]

Step 1. 2-Bromo-1-[4-(methylsulfonyl)phenyl]ethanone (2.4 g, 8.7 mmol) was added over a period of 30 min to the suspension of sodium acetate (0.7 g, 8.7 mmol) in DMF (25 mL) at RT. The mixture was stirred at 25° C. for 16 h, and was partitioned between H₂O (100 mL) and EtOAc/hexane (20/100 mL). The organic layer was separated and washed with water (3×100 mL), dried with anhydrous Na₂SO₄, and concentrated to give 2-[4-(methylsulfonyl)phenyl]-2-oxoethyl acetate. LCMS: m/e=256 [M+1]⁺.

Step 2. The product of Step 1 (2.2 g, 8.7 mmol), NH₄OAc (13.5 g, 170 mmol), and xylene (20 mL) was kept under reflux for 15 h. The reaction mixture was partitioned between H₂O (500 mL)/saturated aq K₂CO (50 mL) and EtOAc/hexane (400/100 mL). The organic layer was separated and washed with water (3×200 mL), dried with anhydrous Na₂SO₄, and concentrated, and the residue was purified by crystallization from Et₂O/hexane to give 2-methyl-5-[4-(methylsulfonyl)phenyl]-1H-imidazole. LCMS: [M+1]⁺=237.1.

Step 3. To the product of Step 2 (750 mg, 3.2 mmol) in 10 mL of CFI₃CN was added N-iodosuccinimide (710 mg, 3.2 mmol). The mixture was stirred at 25° C. for 1 h, cooled to −20° C. The precipitate was collected by filtration, washed with cold Et₂O and dried to give 4-iodo-2-methyl-5-[4-(methylsulfonyl)phenyl]-1H-imidazole. LCMS: [M+1]⁺=362.9.

Step 4. To NaH (60% in mineral oil, 0.12 g, 3.0 mmol) in NMP (10 mL) was added 4-chlorobenzenethiol (0.44 g, 3.0 mmol). After stirring for 15 min, the reaction mixture was added to the product of Step 3 (1.09 g, 3.0 mmol) and CuBr (0.65 g, 4.5 mmol) in NMP (10 mL) under argon. The resulting mixture was kept at 140° C. for 4 h. After cooling, the reaction mixture was partitioned between H₂O and EtOAc. The organic layer was separated, filtered through a thin pad of silica gel, and the filtrate was dried over anhydrous Na₂SO₄, and concentrated. The residue was purified by chromatography on silica gel (DCM to EtOAc) to give 4-[(4-chlorophenyl)thio]-2-methyl-5-[4-(methylsulfonyl)phenyl]-1H-imidazole. LCMS: [M+1]⁺=379.0

Step 5. To the product of Step 4 (0.38 g, 0.96 mmol) and iodomethane (1.0 mL, 1M solution in THF, 1.0 mmol) in THF (5 mL) at 5° C. under argon was added NaH (60% in mineral oil, 0.040 g, 1.0 mmol). After stirring at RT for 16 h, the reaction was partitioned between CH₂Cl₂ (10 mL) and H₂O (20 mL). The organic layer was separated, washed with H₂O, brine, dried with anhydrous Na₂SO₄ and concentrated. The residue was purified by crystallization from EtOAc/hexane to give the title compound. ¹H NMR (400 MHz, CDCl₃): 2.52 (3H, s), 3.03 (3H, s), 3.51 (3H, s), 6.91-6.99 (2H, m), 7.21-7.29 (2H, m), 7.88-7.94 (2H, m), 8.21-8.27 (2H, m). LC-MS: m/z 393.0 [M+H]⁺

Example 28

5-[(4-Chlorophenyl)thio]-2-ethyl-1-methyl-4-[4-(methylsulfonyl)phenyl]-1H-imidazole

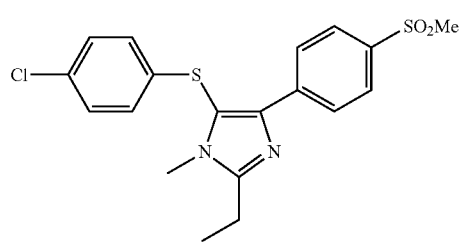 [SMILES: CCc1nc(-c2ccc(S(C)(=O)=O)cc2)c(Sc2ccc(Cl)cc2)n1C]

Step 1. Propionic acid (1.5 mL, 20 mmol) was added over a period of 30 min to a stirred suspension of Cs₂CO₃ (3.30 g, 10 mmol) in MeOH (20 mL). The reaction mixture was concentrated and the residue was suspended in DMF (25 mL), to which was added 2-bromo-1-[4-(methylsulfonyl)phenyl] ethanone (5.00 g, 18 mmol). The mixture was stirred at 25° C. for 16 h, and then partitioned between H₂O (100 mL) and EtOAc/hexane (20/100 mL). The organic layer was separated, washed with water (3×200 mL), dried over anhydrous Na₂SO₄, filtered and concentrated to give 2-[4-(methylsulfonyl)phenyl]-2-oxoethyl propionate. LCMS: [M+1]⁺=271.

Step 2. The product of Step 1 (4.03 g, 15 mmol), NH₄OAc (23.12 g, 300 mmol), and xylene (20 mL) were kept at reflux for 15 h. After cooling, the reaction mixture was partitioned between dilute K₂CO₃, and EtOAc/hexane. The organic layer was separated, washed with H₂O, dried over anhydrous Na₂SO₄, filtered and concentrated. The residue was purified by crystallization from CCl₄/DCM to give 2-ethyl-4-[4-(methylsulfonyl)phenyl]-1H-imidazole. LCMS: [M+1]⁺=251.

Step 3. The product of Step 2 was converted to the title compound following the procedure described for Step 3, 4, 5 of Example 27. ¹H NMR (400 MHz, DMSO-d₆): 1.31 (3H, t), 2.80 (2H, q), 3.19 (3H, s), 3.52 (3H, s), 7.06 (2H, d, J=8.6 Hz), 7.38 (2H, d, J=8.6), 7.91 (2H, d, J=8.6), 8.21 (2H, d, J=8.6 Hz). LC-MS: m/z 407.1 [M+H]⁺.

Example 29

5-[(4-Chlorophenyl)thio]-2-isopropyl-1-methyl-4-[4-(methylsulfonyl)phenyl]-1H-imidazole

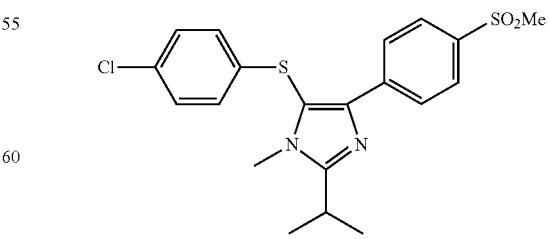

The title compound was prepared from 2-methylpropanoic acid following the procedure described for Example 28. ¹H NMR (400 MHz, DMSO-d₆): 1.31 (6H, d, J=6.9 Hz), 3.18

(3H, s), 3.20-3.25 (1H, m), 3.55 (3H, s), 7.04 (2H, d, J=8.6 Hz), 7.38 (2H, d, J=8.6), 7.91 (2H, d, J=8.6), 8.21 (2H, d, J=8.6 Hz) LC-MS APCI: m/z 421.1 [M+H]+.

Example 30

5-[(4-Chlorophenyl)thio]-2-cyclopentyl-1-methyl-4-[4-(methylsulfonyl)phenyl]-1H-imidazole

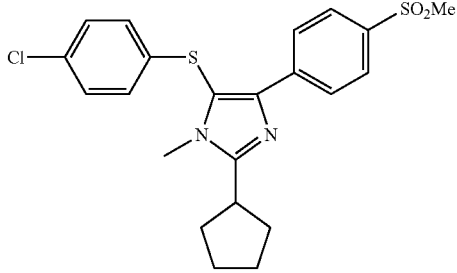 [SMILES: Cn1c(C2CCCC2)nc(-c2ccc(S(C)(=O)=O)cc2)c1Sc1ccc(Cl)cc1]

The title compound was prepared from cyclopentanecarboxylic acid following the procedure described for Example 28. ¹H NMR (400 MHz, DMSO-d₆): 1.59-1.73 (2H, m), 1.74-1.85 (2H, m), 1.86-1.96 (2H, m), 2.00-2.11 (2H, m), 3.18 (3H, s), 3.29-3.37 (1H, m), 3.58 (3H, s), 7.03 (2H, d, J=8.6 Hz), 7.38 (2H, d, J=8.6), 7.91 (2H, d, J-8.6), 8.21 (2H, d, J=8.6 Hz). LC-MS [M+1]+=447

Example 31

5-[(4-Chlorophenyl)thio]-2-cyclohexyl-1-methyl-4-[4-(methylsulfonyl)phenyl]-1H-imidazole

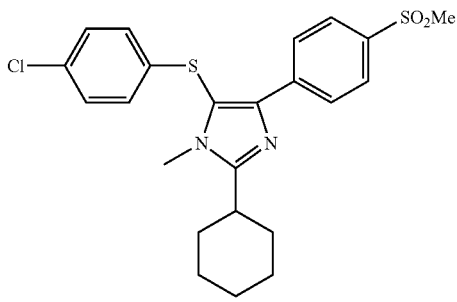 [SMILES: Cn1c(C2CCCCC2)nc(-c2ccc(S(C)(=O)=O)cc2)c1Sc1ccc(Cl)cc1]

The title compound was prepared from cyclohexanecarboxylic acid following the procedure described for Example 28. ¹H NMR (400 MHz, DMSO-d₆): 1.21-1.47 (3H, m), 1.54-1.76 (3H, m), 1.77-1.87 (2H, m), 1.88-1.98 (2H, m), 2.94-2.82 (1H, m), 3.18 (3H, s), 3.55 (3H, s), 7.03 (2H, d, J=8.6 Hz), 7.38 (2H, d, J=8.6), 7.91 (2H, d, J=8.3), 8.21 (2H, d, J=8.3 Hz). LC-MS APCI: m/z 461.1 [M+H]+.

Example 32

5-[(4-chlorophenyl)thio]-1-methyl-4-[4-(methylsulfonyl)phenyl]-2-(tetrahydro-2H-pyran-4-yl)-1H-imidazole

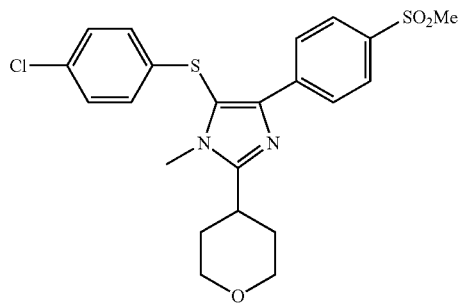 [SMILES: Cn1c(C2CCOCC2)nc(-c2ccc(S(C)(=O)=O)cc2)c1Sc1ccc(Cl)cc1]

The title compound was prepared from tetrahydro-2H-pyran-4-carboxylic acid following the procedure described for Example 28. ¹H NMR (400 MHz, DMSO-d₆): 1.77-1.93 (4H, m), 3.12-3.24 (3H, s, 1H, m), 3.42-3.54 (2H, m), 3.58 (3H, s), 3.91-4.03 (2H, m), 7.03 (2H, d, J=8.6 Hz), 7.38 (2H, d, J=8.6), 7.91 (2H, d, J=8.6), 8.21 (2H, d, J=8.6 Hz). LC-MS: m/z 463.1 [M+H]+.

Example 33

4-{5-[(4-chlorophenyl)thio]-1-methyl-1H-imidazol-4-yl}benzonitrile

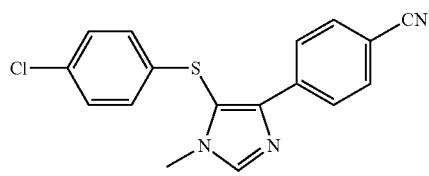 [SMILES: Cn1cnc(-c2ccc(C#N)cc2)c1Sc1ccc(Cl)cc1]

Step 1. Methylamine (100 mL of 2M solution in THF) was charged into a 500 mL flask, to which was added 150 mL of Et₂O. At −78° C., 15 g of 4-bromoacetyl benzonitrile was added, and the reaction was allowed to warm to rt. After stirring for 5 h, the reaction mixture was poured into a separatory funnel and shaken with 15% aq NaOH (20 mL). The precipitate was collected by filtration, and air-dried to give 4-(N-methylglycyl)benzonitrile.

Step 2. 4-(N-Methylglycyl)benzonitrile (2.6 g) and 20 ml of formamide were heated in a microwave tube at 210° C. for 20 min. The reaction was diluted with EtOAc, made basic with 15% aq NaOH, washed with water (3×100 mL) and brine, dried over MgSO₄, filtered, and concentrated. The residue was subject to silica column chromatography (70% EtOAc in hexanes to 100% EtOAc) to give 1.05 g of 4-(1-methyl-1H-imidazol-4-yl)benzonitrile. LCMS: M+1=184.

Step 3. To 4-(1-methyl-1H-imidazol-4-yl)benzonitrile (Step 2, 1.05 g, 5.73 mmol) in methylene chloride (15 mL) was added NCS (765 mg, 5.73 mmol) and 3 drops of TFA. After stirring at 50° C. for 3 hrs, the reaction was diluted with 20 mL of methylene chloride and quenched with aq NaHCO$_3$. The organic layer was washed with water, brine, dried over MgSO$_4$, filtered, and concentrated to give 4-(5-chloro-1-methyl-1H-imidazol-4-yl)benzonitrile. LCMS: [M+1]=218.

Step 4. 4-(5-Chloro-1-methyl-1H-imidazol-4-yl)benzonitrile (1 g), 4-chlorobenzenethiol (797 mg), and 1.3 ml of triethylamine in 20 mL of DMF were heated in a microwave tube at 180° C. for 90 min. The reaction mixture was purified by reverse phase HPLC with MS detector to afford the title compound. 1H NMR (500 MHz, (CDCl$_3$): 8.21 (d, 2H), 7.83 (s, 1H), 7.66 (d, 2H), 7.45 (d, 2H), 6.98 (d, 2H), 3.63 (s, 3H). LCMS: [M+1]=326.

Example 34

4-{5-[(4-Chlorophenyl)thio]-2-iodo-1-methyl-1H-imidazol-4-yl}benzonitrile

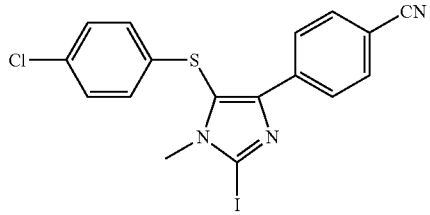 [SMILES: Cn1c(I)nc(-c2ccc(C#N)cc2)c1Sc1ccc(Cl)cc1]

To 4-{5-[(4-chlorophenyl)thio]-1-methyl-1H-imidazol-4-yl}benzonitrile (Example 31, 50 mg, 0.153 mmol) in THF (0.75 mL) was added freshly made LDA (0.2 mL, 0.2 mmol) at −78° C. After stirring at −78° C. for 1 h, I$_2$ (55 mg, 0.215 mmol) was added and the reaction was warmed up to rt and stirred overnight. The reaction was quenched with aq NH$_4$Cl, and the product was extracted with EtOAc. The combined extracts were washed with aq Na$_2$S$_2$O$_3$, water, and brine, dried over MgSO$_4$, filtered, and concentrated. The residue was purified by silica column chromatography (5-20% EtOAc in hexanes) to give the title compound. 1H NMR (500 MHz, (CDCl$_3$): 8.20 (d, 2H), 7.65 (d, 2H), 7.28 (d, 2H), 6.99 (d, 2H), 3.62 (s, 3H). LCMS: [M+1]=451.9.

Example 35

4-{5-[(4-Chlorophenyl)thio]-1-ethyl-2-phenyl-1H-imidazol-4-yl}benzonitrile

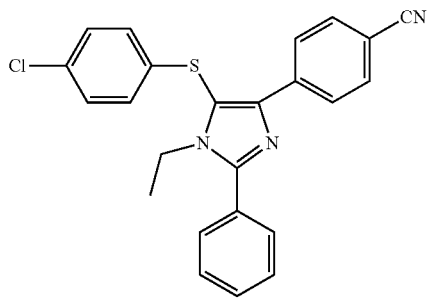 [SMILES: CCn1c(-c2ccccc2)nc(-c2ccc(C#N)cc2)c1Sc1ccc(Cl)cc1]

To 4-{5-[(4-chlorophenyl)thio]-2-phenyl-1H-imidazol-4-yl}benzonitrile (Example 2, 10 mg) in THF (1 mL) was added NaH (60% wt, 15 mg) at 0° C. After stirring for 5 min, EtI (0.05 mL) was added. The reaction was stirred at 50° C. overnight, then quenched with aq NH$_4$Cl to adjust the pH to 6-8. The product was extracted with EtOAc and the combined extracts were washed with water, brine, dried over MgSO$_4$, filtered, and concentrated. The residue was subject to silica column chromatography (0-15% EtOAc in hexanes) to give the title compound. LCMS: m/z 416 (M+H)+.

Example 36

5-Chloro-2-({1-methyl-4-[4-(1,3,4-oxadiazol-2-yl)phenyl]-2-pyridin-2-yl-1H-imidazol-5-yl}thio)pyridine

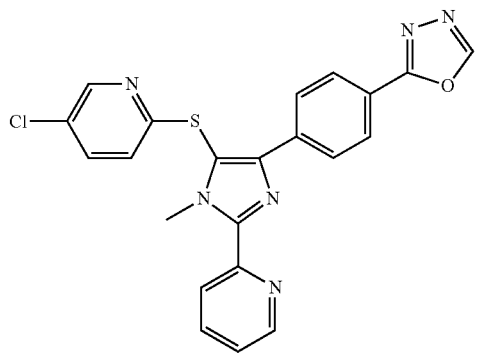 [SMILES: Cn1c(-c2ccccn2)nc(-c2ccc(-c3nnco3)cc2)c1Sc1ccc(Cl)cn1]

CuI (136 mg), K$_2$CO$_3$ (2 g), Intermediate 7 (3.07 g, dried by azeotroping with PhMe), and Intermediate 1 (2.5 g) were added to a flask, which was flushed with N$_2$. 2-Propanol (25 mL) and ethylene glycol (0.8 mL) were added, and the reaction was heated at 80° C. for 24 hrs. After cooling to rt, the reaction mixture was concentrated to dryness. The residue was purified by silica gel column chromatography eluting with hexanes/CH$_2$Cl$_2$/EtOAc (v/v/v 25:25:50) to afford 2.3 g of pure product. 1H NMR (500 MHz, (CD$_3$OD): 9.01 (s, 1H), 8.93 (d, 1H), 8.42 (s, 1H), 8.23 (d, 1H), 8.19 (d, 2H), 8.09 (d, 2H), 8.01 (m, 1H), 7.77 (d, 1H), 7.49 (m, 1H), 7.18 (d, 1H), 4.06 (s, 3H). LCMS: m/z 447 (M+H)+.

The examples in Table 2 were prepared following the procedures described in Example 36 using the appropriate thiol and Intermediate 7 as the starting materials.

TABLE 2

| Example | Compound structure | LCMS rt (min) | M + 1 |
|---|---|---|---|
| 37 | 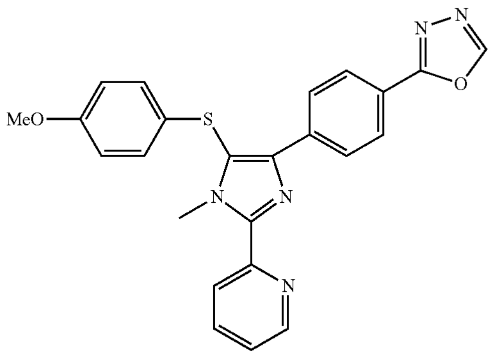 [SMILES: COc1ccc(Sc2c(-c3ccc(-c4nnco4)cc3)nc(-c3ccccn3)n2C)cc1] | 1.18 | 442 |
| 38 | 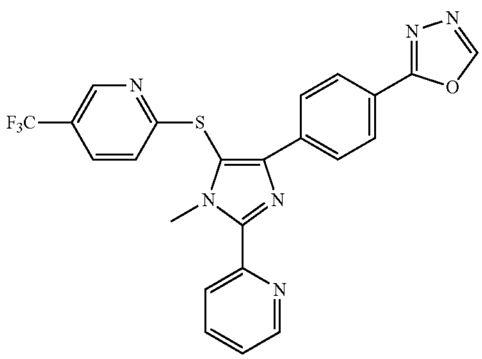 [SMILES: Cn1c(-c2ccccn2)nc(-c2ccc(-c3nnco3)cc2)c1Sc1ccc(C(F)(F)F)cn1] | 1.19 | 481 |
| 39 | 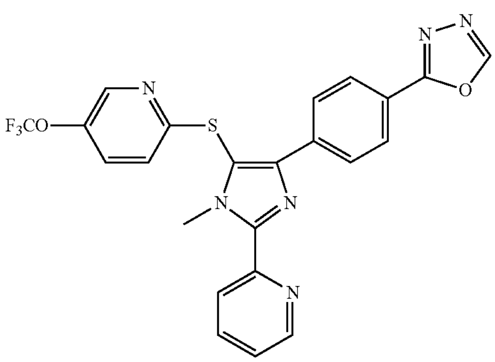 [SMILES: Cn1c(-c2ccccn2)nc(-c2ccc(-c3nnco3)cc2)c1Sc1ccc(OC(F)(F)F)cn1] | 1.26 | 496 |
| 40 | 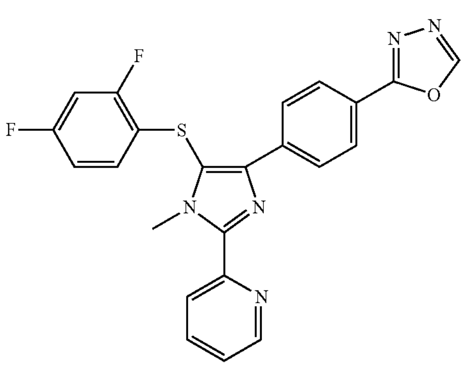 [SMILES: Cn1c(-c2ccccn2)nc(-c2ccc(-c3nnco3)cc2)c1Sc1ccc(F)cc1F] | 1.21 | 448 |

TABLE 2-continued

| Example | Compound structure | LCMS rt (min) | M + 1 |
|---|---|---|---|
| 41 | 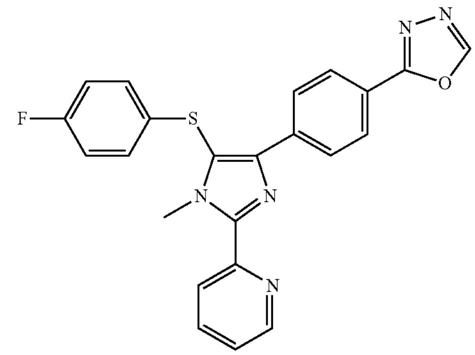 [SMILES: Cn1c(-c2ccccn2)nc(-c2ccc(-c3nnco3)cc2)c1Sc1ccc(F)cc1] | 1.20 | 430 |
| 42 | 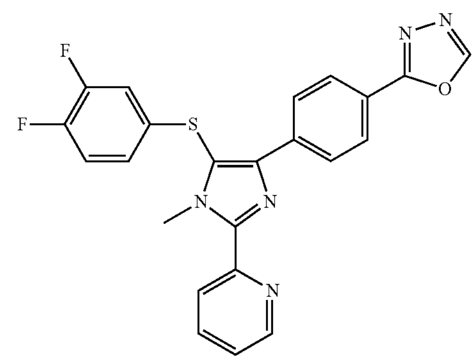 [SMILES: Cn1c(-c2ccccn2)nc(-c2ccc(-c3nnco3)cc2)c1Sc1ccc(F)c(F)c1] | 1.21 | 448 |
| 43 | 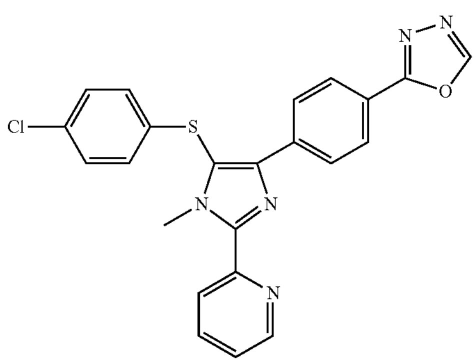 | 1.22 | 446 |
| 44 | 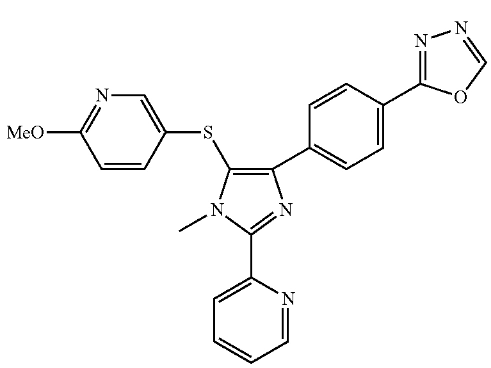 [SMILES: COc1ccc(Sc2c(-c3ccc(-c4nnco4)cc3)nc(-c3ccccn3)n2C)cn1] | 443 | 1.12 |

TABLE 2-continued

| Example | Compound structure | LCMS rt (min) | M + 1 |
|---|---|---|---|
| 45 | 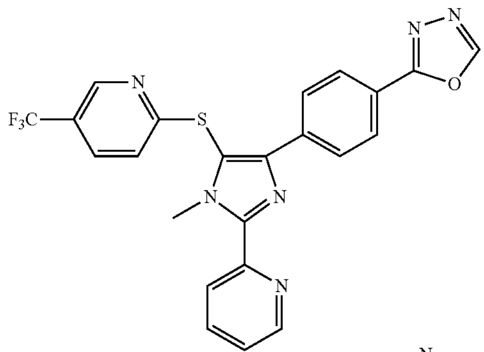 [SMILES: Cn1c(-c2ccccn2)nc(-c2ccc(-c3nnco3)cc2)c1Sc1ccc(C(F)(F)F)cn1] | 437 | 1.22 |
| 46 | 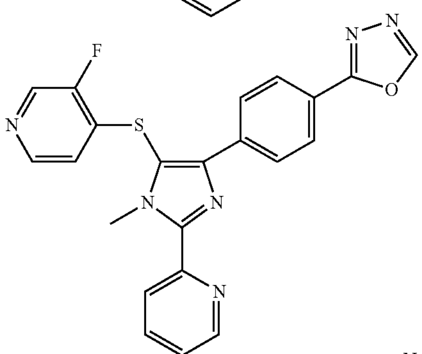 | 431 | 1.11 |
| 47 | 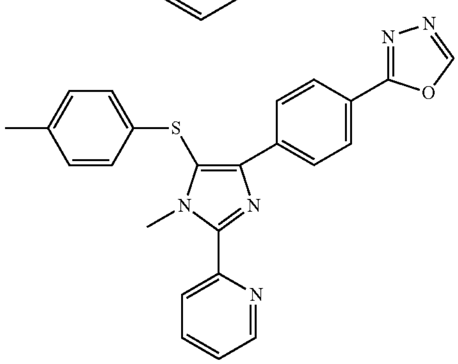 | 426 | 1.18 |

Example 48

2-{5-[(4-Chlorophenyl)thio]-1-methyl-4-[4-(5-methyl-1,3,4-oxadizol-2-yl)phenyl]-1H-imidazol-2-yl}pyridine

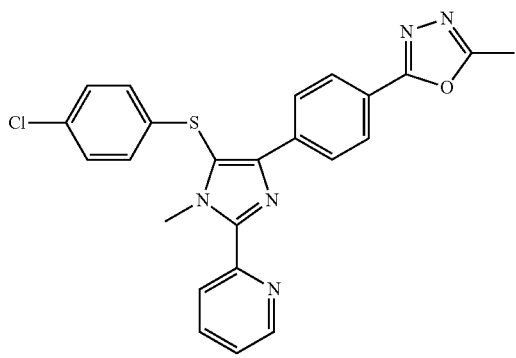 [SMILES: Cc1nnc(-c2ccc(-c3nc(-c4ccccn4)n(C)c3Sc3ccc(Cl)cc3)cc2)o1]

Step 1. Starting with compound of Example 18 and following the procedure described in Step 4 for Intermediate 7, 4-{5-[(4-chlorophenyl)thio]-1-methyl-2-pyridin-2-yl-1H-imidazol-4-yl}benzohydrazide was prepared. LCMS: m/z 436, (M+H)+.

Step 2. Starting with 4-{5-[(4-chlorophenyl)thio]-1-methyl-2-pyridin-2-yl-1H-imidazol-4-yl}benzohydrazide (Step 1) and trimethyl orthoacetate, the title compound was prepared following the procedure described in Step 5 of Intermediate 7. 1H NMR (500 MHz, (D$_6$-acetone): 8.73 (d, 1H), 8.41 (d, 1H), 8.40 (d, 2H), 8.07 (d, 2H), 8.01 (t, 1H), 7.47 (m, 1H), 7.38 (d, 1H), 7.22 (d, 2H), 4.18 (s, 3H), 2.68 (s, 3H). LCMS: m/z 460 (M+H)+.

Example 49

4-{5-[(4-Chlorophenyl)thio]-1-methyl-2-pyridin-2-yl-1H-imidazol-4-yl}-N'-formylbenzohydrazide

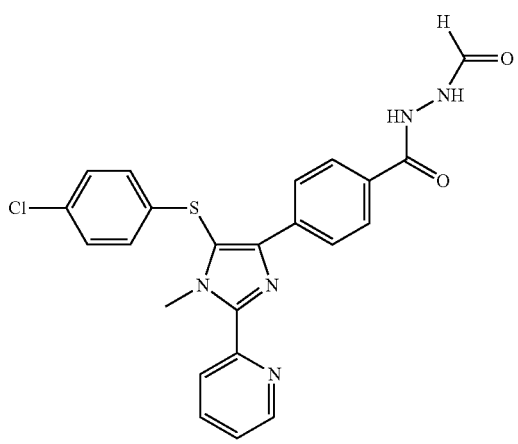 [SMILES: Cn1c(-c2ccccn2)nc(-c2ccc(C(=O)NNC=O)cc2)c1Sc1ccc(Cl)cc1]

4-{5-[(4-Chlorophenyl)thio]-1-methyl-2-pyridin-2-yl-1H-imidazol-4-yl}benzohydrazide (Step 1 of Example 48, 400 mg) was dissolved in 3 mL of formic acid. After stirring overnight, the volatiles were removed under reduced pressure to afford the title compound. 1H NMR (500 MHz, (CDCl$_3$): 8.84 (broad d, 1H), 8.41 (d, 1H), 8.19 (d, 2H), 7.85 (t, 1H), 7.48 (broad d, 2H), 7.38 (t, 1H), 7.23 (d, 2H), 7.04 (d, 2H), 4.14 (s, 3H). LCMS: m/z 464, (M+H)+.

Example 50

2-{5-[(4-Chlorophenyl)thio]-1-methyl-4-[4-(1,3,4-thiadiazol-2-yl)phenyl]-1H-imidazol-2-yl}pyridine

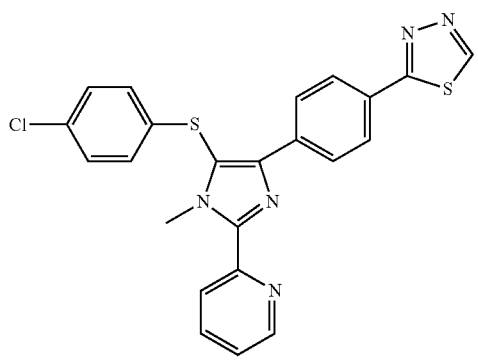 [SMILES: Cn1c(-c2ccccn2)nc(-c2ccc(-c3nncs3)cc2)c1Sc1ccc(Cl)cc1]

4-{5-[(4-Chlorophenyl)thio]-1-methyl-2-pyridin-2-yl-1H-imidazol-4-yl}-N'-formylbenzohydrazide (Example 49, 450 mg, 0.98 mmol) was treated with P$_2$S$_5$ (218 mg, 0.98 mmol) in 12 mL of dioxane. After the reaction mixture was heated at 55° C. overnight, the volatiles were removed in vacuo. The residue was diluted with EtOAc, washed with 1N NaOH, water, and brine. The organic layer was dried over MgSO$_4$, filtered, and concentrated. The residue was subjected to silica gel column chromatography eluting with 30-85% EtOAc in hexanes to afford the title compound. 1H NMR (500 MHz, (CDCl$_3$): 9.13 (s, 1H), 8.67 (d, 1H), 8.43 (broad d, 1H), 8.38 (d, 2H), 8.06 (d, 2H), 7.89 (t, 1H), 7.39 (t, 1H), 7.25 (d, 2H), 7.04 (d, 2H), 4.16 (s, 3H). LCMS: m/z 462 (M+H)+.

Example 51

5-(4-{5-[4-Chlorophenyl)thio]-1-methyl-2-pyridin-2-yl-1H-imidazol-4-yl}phenyl)-1,3,4-oxadiazol-2-amine

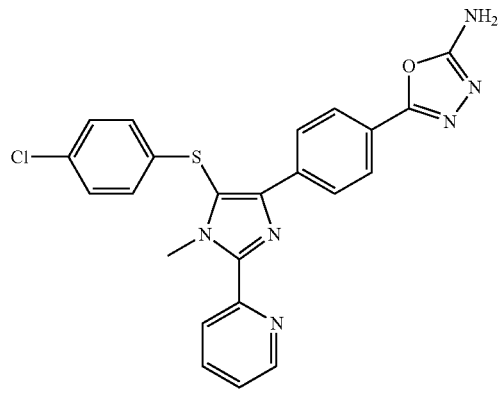 [SMILES: Cn1c(-c2ccccn2)nc(-c2ccc(-c3nnc(N)o3)cc2)c1Sc1ccc(Cl)cc1]

A solution of NaHCO$_3$ (20 mg, 0.238 mmol) in water (0.5 mL) was added dropwise to a stirred solution of 4-{5-[(4-chlorophenyl)thio]-1-methyl-2-pyridin-2-yl-1H-imidazol-4-yl}benzohydrazide (Step 1 of Example 48, 100 mg, 0.229 mmol) in 2 mL of dioxane at rt. A suspension of cyanogen bromide (29 mg, 0.275 mmol) in dioxane (0.25 mL) was added in 4-equal portions at 1 min intervals. After 45 min, the reaction mixture was poured into aq NaHCO$_3$ and the product was extracted 3 times with EtOAc. The organic extracts were concentrated, and the residue was subjected to reverse phase HPLC. The fractions containing the product were collected and concentrated. The residue was diluted with EtOAc, washed with aq NaHCO$_3$, water, and brine. The organic layer was dried over MgSO$_4$, filtered, and concentrated to afford the title compound. 1H NMR (500 MHz, (CDCl$_3$): 8.71 (d, 1H), 8.58 (broad d, 1H), 8.35 (d, 2H), 7.97 (d, 2H), 7.88 (m, 1H), 7.41 (m, 1H), 7.25 (d, 2H), 7.04 (d, 2H), 4.14 (s, 3H). LCMS: m/z 461 (M+H)+.

Example 52

5-(4-{5-[(4-Chlorophenyl)thio]-1-methyl-2-pyridin-2-yl-1H-imidazol-4-yl}phenyl)-1,3,4-oxadiazol-2 (3H)-one

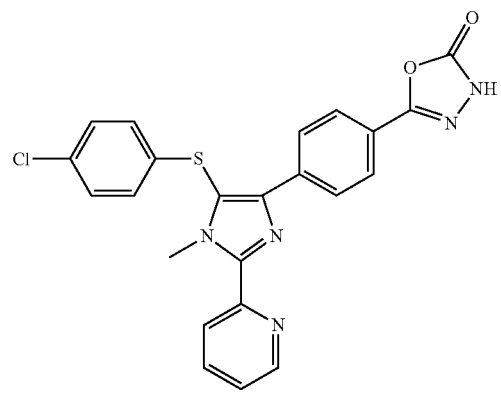 [SMILES: Cn1c(-c2ccccn2)nc(-c2ccc(-c3n[nH]c(=O)o3)cc2)c1Sc1ccc(Cl)cc1]

To 4-{5-[(4-chlorophenyl)thio]-1-methyl-2-pyridin-2-yl-1H-imidazol-4-yl}benzohydrazide (Step 1 of Example 48, 120 mg, 0.27 mmol) in THF (1 mL) was added phosgene (PhMe solution, 0.55 mmol) at −78° C. After stirring at −78° C. for 60 min, the reaction was quenched with aq NaHCO₃ and the product was extracted with EtOAc. The combined extracts were washed with water, brine, dried over MgSO₄, filtered, and concentrated. The residue was re-crystallized in MeCN/MeOH to afford the title compound. 1H NMR (500 MHz, (CDCl₃): 8.68 (d, 1H), 8.42 (broad d, 1H), 8.28 (d, 2H), 7.91 (d, 2H), 7.89 (m, 1H), 7.37 (m, 1H), 7.27 (d, 2H), 7.06 (d, 2H), 4.17 (s, 3H). LCMS: m/z 462 (M+H)+.

Example 53

5-(4-{5-[(4-Chlorophenyl)thio]-1-methyl-2-pyridin-2-yl-1H-imidazol-4-yl}phenyl)-1,3,4-oxadiazol-2 (3H)-thione

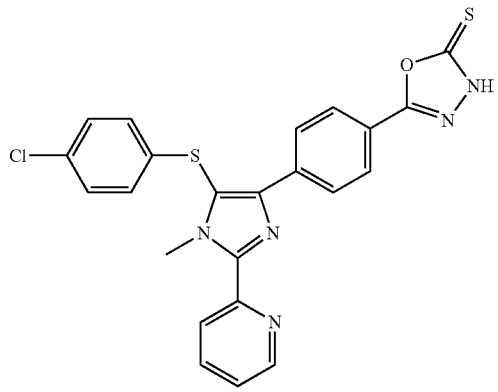 [SMILES: Cn1c(-c2ccccn2)nc(-c2ccc(-c3n[nH]c(=S)o3)cc2)c1Sc1ccc(Cl)cc1]

To 4-{5-[(4-chlorophenyl)thio]-1-methyl-2-pyridin-2-yl-1H-imidazol-4-yl}benzohydrazide (Step 1 of Example 48, 50 mg, 0.115 mmol) and 1,1'-carbonothioylbis(1H-imidazole) (41 mg, 0.23 mmol) in dichloromethane (1 mL) was added triethylamine (46 mg, 0.46 mmol) at rt. After 1 h, the reaction was quenched with aq NaHCO₃ and the product was extracted 3 times with EtOAc. The combined extracts were concentrated, and the residue was subjected to reverse phase HPLC. The fractions containing the product were collected and concentrated. The residue was diluted with EtOAc, washed with aq NaHCO₃, water, and brine. The organic layer was dried over MgSO₄, filtered, and concentrated to afford the title compound. 1H NMR (500 MHz, (CDCl₃): 8.65 (d, 1H), 8.38 (broad d, 1H), 8.36 (d, 2H), 8.19 (s, 1H), 8.03 (d, 2H), 7.84 (m, 1H), 7.38 (m, 1H), 7.27 (d, 2H), 7.07 (d, 2H), 4.16 (s, 3H). LCMS: m/z 478 (M+H)+.

Example 54

1-(4-{5-[(4-Chlorophenyl)thio]-1-methyl-2-pyridin-2-yl-1H-imidazol-4-yl}phenyl)ethanone

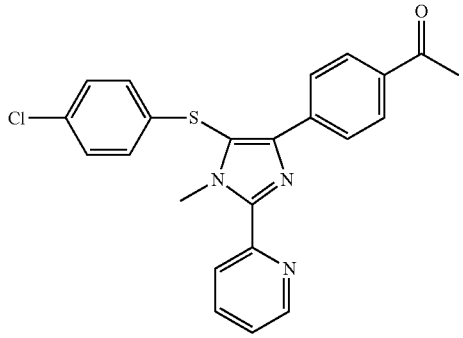 [SMILES: CC(=O)c1ccc(-c2nc(-c3ccccn3)n(C)c2Sc2ccc(Cl)cc2)cc1]

A mixture of 2-{4-(4-bromophenyl)-5-[(4-chlorophenyl)thio]-1-methyl-1H-imidazol-2-yl}pyridine (Example 15, 2 g, 4.38 mmol), (1-ethoxyvinyul)tributyltin (1.7 g, 4.82 mmol), PdCl₂(PPh₃)₂ (67 mg, 0.2 mmol), and 15 mL of toluene under nitrogen was heated at 100° C. overnight. The reaction mixture was diluted with EtOAc, washed with H₂O, brine, dried over MgSO₄, filtered. To the filtrate was added KF/Celite (50% wt from Aldrich) which was stirred for 1.5 h. Upon filtration and concentration, the residue was taken up in 20 mL of EtOH and 10 mL of 2 N HCl, stirred at rt for 1 h. The precipitate was collected by filtration, washed with water and a small amount of EtOAc. The solid was further purified by silica gel column chromatography (10-50% EtOAc in hexanes) to give the title compound. 1H NMR (500 MHz, (CDCl₃): 8.62 (d, 1H), 8.38 (d, 1H), 8.26 (d, 2H), 8.19 (d, 2H), 7.83 (t, 1H), 7.31 (t, 1H), 7.23 (d, 2H), 7.04 (d, 2H), 4.13 (s, 3H), 2.61 (s, 3H). LCMS: m/z 420 (M+H)+.

Example 55

1-(4-{5-[(4-Chlorophenyl)thio]-1-methyl-2-pyridin-2-yl-1H-imidazol-4-yl}phenyl)ethanol

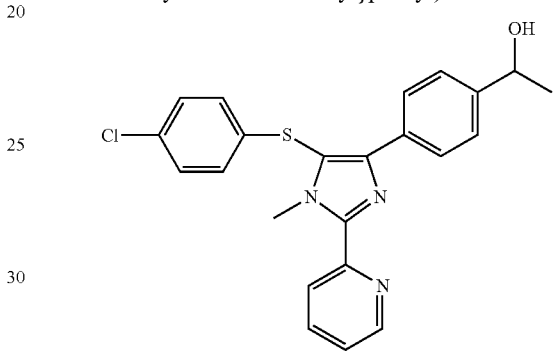

To 1-(4-{5-[(4-chlorophenyl)thio]-1-methyl-2-yl-1H-imidazol-4-yl}phenyl)ethanol (Example 54, 428 mg, 1.0 mmol) in 5 mL of MeOH was added NaBH₄ (77 mg, 2.0 mmol) at 0° C. After 5 min, the reaction was quenched with aqueous NH₄Cl and the product was extracted with EtOAc. The combined extracts were washed with water and brine, dried over MgSO₄, filtered, and concentrated to give the title compound. 1H NMR (500 MHz, (CDCl₃): 8.67 (d, 1H), 8.41 (m, 1H), 8.21 (d, 2H), 7.85 (t, 1H), 7.42 (d, 2H), 7.37 (m, 1H), 7.25 (d, 2H), 7.07 (d, 2H), 4.96 (m, 1H), 4.11 (s, 3H), 1.56 (d, 3H). LCMS: m/z 422 (M+H)+. The racemic alcohol was resolved on a Chiral OJ column (25% EtOH/75% hexanes, flow rate 1 mL/min) to give two enantiomers: faster enantiomer's retention time=19.3 min; slower enantiomer's retention time=22.1 min.

Example 56

1-(4-{5-[4-Chlorophenyl)thio]-1-methyl-2-pyridin-2-yl-1H-imidazol-4-yl}phenyl)-2,2-difluoroethanone

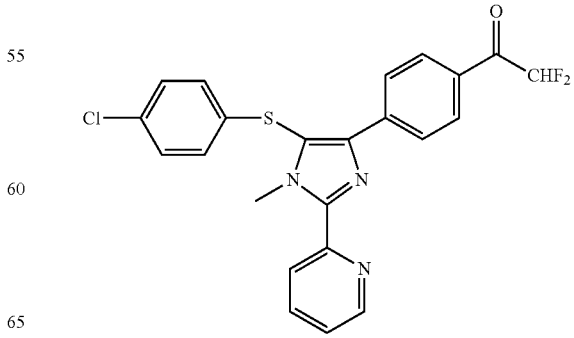

To 2-{4-(4-bromophenyl)-5-[(4-chlorophenyl)thio]-1-methyl-1H-imidazol-2-yl}pyridine (Example 15, 150 mg, 0.33 mmol) in 1 mL of THF was added BuLi (2.5 mL in hexanes, 0.16 mL, 0.39 mmol) at −78° C. After stirring at −78° C. for 10 min, ethyl difluoroacetate (61 mg, 0.493 mmol) was added and the reaction was allowed to warm up slowly to rt. Then the reaction was quenched with aqueous NH₄Cl and the product was extracted with EtOAc. The combined extracts were washed with water and brine, dried over MgSO₄, filtered, and concentrated. The residue was purified by reverse phase HPLC to afford the title compound. 1H NMR (500 MHz, (CDCl₃): 8.64 (d, 1H), 8.38 (d, 1H), 8.36 (d, 2H), 8.16 (d, 2H), 7.88 (t, 1H), 7.37 (t, 1H), 7.28 (d, 2H), 7.03 (d, 2H), 6.38 (t, 1H), 4.17 (s, 3H). LCMS: m/z 456 (M+H)+.

Example 57

1-(4-{5-[(4-Chlorophenyl)thio]-1-methyl-2-pyridin-2-yl-1H-imidazol-4-yl}phenyl)-2,2-difluoroethanol

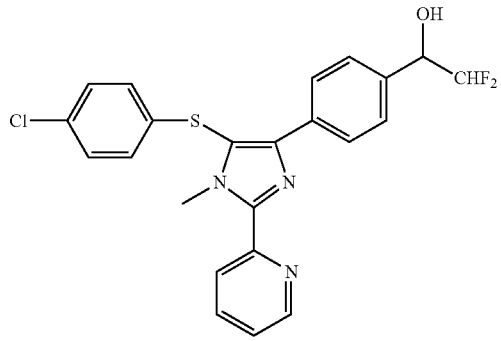 [SMILES: Cn1c(-c2ccccn2)nc(-c2ccc(C(O)C(F)F)cc2)c1Sc1ccc(Cl)cc1]

The title compound was prepared from 1-(4-{5-[(4-chlorophenyl)thio]-1-methyl-2-pyridin-2-yl-1H-imidazol-4-yl}phenyl)-2,2-difluoroethanone (Example 56) following the procedure described for Example 55. 1H NMR (500 MHz, (CDCl₃): 8.65 (d, 1H), 8.38 (d, 1H), 8.04 (d, 2H), 7.84 (t, 1H), 7.39 (d, 2H), 7.36 (t, 1H), 7.26 (d, 2H), 7.03 (d, 2H), 5.74 (dt, 1H), 4.58 (m, 1H), 4.12 (s, 3H). LCMS: m/z 458 (M+H)+. The racemic alcohol was resolved on a Chiral AD-H column (20% EtOH/80% hexanes, flow rate 1 mL/min) to give two enantiomers: faster enantiomer's retention time=17.8 min; slower enantiomer's retention time=20.4 min.

Example 58

1-(4-{5-[(4-Chlorophenyl)thio]-1-methyl-2-pyridin-2-yl-1H-imidazol-4-yl}phenyl)-2,2,2-trifluoroethanone

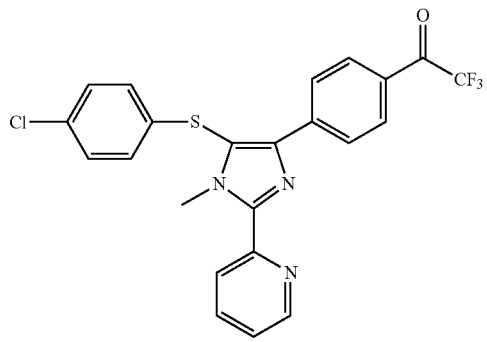 [SMILES: Cn1c(-c2ccccn2)nc(-c2ccc(C(=O)C(F)(F)F)cc2)c1Sc1ccc(Cl)cc1]

The title compound was prepared following the procedure described for Example 56, using ethyl trifluoroacetate instead of ethyl difluoroacetate. 1H NMR (500 MHz, (CDCl₃): 8.64 (broad s, 1H), 8.39 (d, 1H), 8.38 (d, 1H), 8.12 (d, 2H), 7.88 (t, 1H), 7.38 (m, 1H), 7.23 (d, 2H), 7.05 4.17 (s, 3H). LCMS: m/z 474 (M+H)+.

Example 59

1-(4-{5-[(4-Chlorophenyl)thio]-1-methyl-2-pyridin-2-yl-1H-imidazol-4-yl}phenyl)-2,2,2-trifluoroethanol

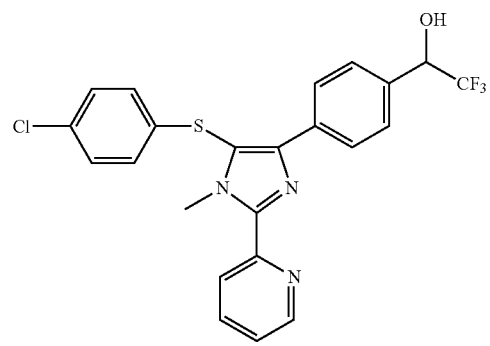 [SMILES: Cn1c(-c2ccccn2)nc(-c2ccc(C(O)C(F)(F)F)cc2)c1Sc1ccc(Cl)cc1]

The title compound was prepared from 1-(4-{5-[(4-chlorophenyl)thio]-1-methyl-2-pyridin-2-yl-1H-imidazol-4-yl}phenyl)-2,2,2-trifluoroethanone (Example 58) following the procedure described for Example 55. 1H NMR (500 MHz, (CDCl₃): 8.64 (broad s, 1H), 8.39 (broad d, 1H), 7.84 (t, 1H), 7.36 (t, 1H), 7.25 (d, 2H), 7.23 (d, 2H), 7.06 (d, 2H), 7.03 (d, 2H), 4.59 (m, 1H), 4.15 (s, 3H). LCMS: m/z 476 (M+H)+.)+. The racemic alcohol was resolved on a Chiral OJ column (20% EtOH/80% hexanes, flow rate 1 mL/min) to give two enantiomers: faster enantiomer's retention time=15.8 min; slower enantiomer's retention time=18.9 min.

Example 60

Methyl 2-(4-{5-[(4-chlorophenyl)thio]-1-methyl-2-pyridin-2-yl-1H-imidazol-4-yl}phenyl)-2-methylpropanoate

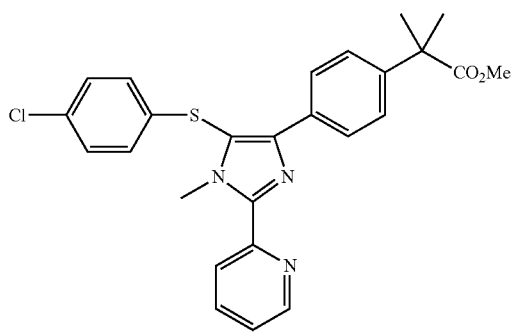 [SMILES: COC(=O)C(C)(C)c1ccc(-c2nc(-c3ccccn3)n(C)c2Sc2ccc(Cl)cc2)cc1]

LiHMDS (1.4 mL of 1 M solution in PhMe) was added to methyl isobutyrate(134 mg, 1.3 mmol) at 0° C. The solution was stirred for 10-15 min at it before it was transferred to a flask containing 2-{4-[(4-bromophenyl)-5-[(4-chlorophenyl)

thio]-1-methyl-1H-imidazol-2-yl}pyridine (Example 15, 200 mg, 0.44 mmol), Pd(dba)$_2$ (25 mg, 0.044 mmol), and tri-t-butylphosphonium tetrafluoroborate (13 mg, 0.044 mmol) in 1 mL of PhMe. After stirring at rt overnight, it was quenched with aqueous NH$_4$Cl and the product was extracted with EtOAc. The combined extracts were washed with water and brine, dried over MgSO$_4$, filtered, and concentrated. The residue was purified on silica gel column chromatography (5-15% EtOAc in hexanes) to give the title compound. 1H NMR (500 MHz, (CDCl$_3$): 8.67 (d, 1H), 8.38 (d, 1H), 8.06 (d, 2H), 7.84 (t, 1H), 7.39 (d, 2H), 7.32 (t, 1H), 7.24 (d, 2H), 7.05 (d, 2H), 4.13 (s, 3H), 3.65 (s, 3H), 1.61 (s, 6H). LCMS: m/z 478 (M+H)+.

Example 61

2-[5-[(4-Chlorophenyl)thio]-4-(4-iodophenyl)-1-methyl-1H-imidazol-2-yl]pyridine

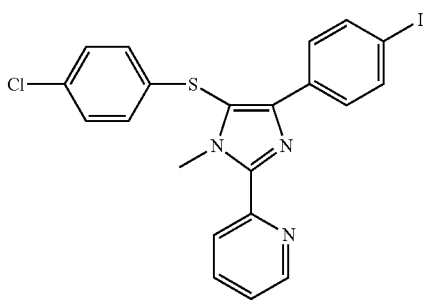 [SMILES: Cn1c(-c2ccccn2)nc(-c2ccc(I)cc2)c1Sc1ccc(Cl)cc1]

To 2-{4-(4-bromophenyl)-5-[(4-chlorophenyl)thio]-1-methyl-1H-imidazol-2-yl}pyridine (Example 15, 150 mg, 0.33 mmol) in THF (1 mL) was added BuLi (2.5 M in hexanes, 0.17 mL, 0.427 mmol) at −78° C. After stirring at −78° C. for 0.5 h, I$_2$ (167 mg, 0.657 mmol) was added and the reaction was allowed to warm up to rt overnight. The reaction was quenched with aq NH$_4$Cl, extracted with EtOAc. The combined extracts were washed with aq Na$_2$S$_2$O$_3$, water, and brine, dried over MgSO$_4$, filtered, and concentrated. The residue was purified by silica gel column chromatography (1-20% EtOAc in hexanes) to give the title compound. 1H NMR (500 MHz, (CDCl$_3$): 8.64 (d, 1H), 8.38 (d, 1H), 7.87 (d, 2H), 7.85 (t, 1H), 7.78 (d, 2H), 7.38 (t, 1H), 7.25 (d, 2H), 7.03 (d, 2H), 4.11). LCMS: [M+1]=504.

Example 62

2-{5-[(4-Chlorophenyl)thio]-1-methyl-4-[4-(1H-pyrazol-1-yl)phenyl]-1H-imidazol-2-yl}pyridine

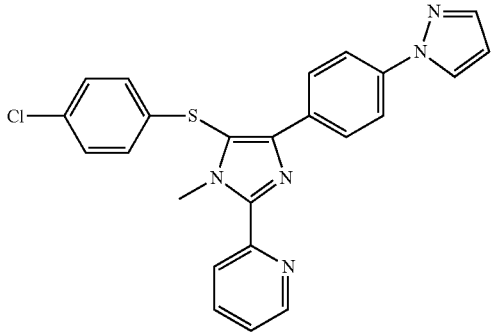 [SMILES: Cn1c(-c2ccccn2)nc(-c2ccc(-n3cccn3)cc2)c1Sc1ccc(Cl)cc1]

To a microwave tube were added 2-[5-[(4-chlorophenyl)thio]-4-(4-iodophenyl)-1-methyl-1H-imidazol-2-yl]pyridine (Example 61, 150 mg, 0.298 mmol), CuI (5.67 mg, 0.03 mmol), pyrazole (41 mg, 0.595 mmol), potassium carbonate (82 mg, 0.595 mmol), and 4 mL of NMP. The reaction was heated at 195° C. for 90 min via microwave. After filtration through Celite, the reaction mixture was purified by reverse phase HPLC to afford the title compound. 1H NMR (500 MHz, (CDCl$_3$): 8.66 (d, 1H), 8.37 (d, 1H), 8.24 (d, 2H), 7.96 (d, 1H), 7.86 (dt, 1H), 7.76 (d, 2H), 7.54 (d, 2H), 7.53 (m, 1H), 7.33 (dd, 1H), 7.24 (d, 2H), 7.06 (d, 2H), 6.48 (m, 1H), 4.16 (s, 3H). LCMS: m/z 444 (M+H)+.

Example 63

2-{5-[(4-Chlorophenyl)thio]-4-[4-(1H-imidazol-1-yl)phenyl]-1-methyl-1H-imidazol-2-yl}pyridine

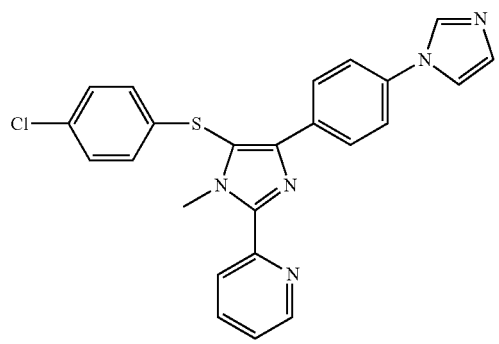 [SMILES: Cn1c(-c2ccccn2)nc(-c2ccc(-n3ccnc3)cc2)c1Sc1ccc(Cl)cc1]

To a microwave tube were added 2-[5-[(4-chlorophenyl)thio]-4-(4-iodophenyl)-1-methyl-1H-imidazol-2-yl]pyridine (Example 61, 150 mg, 0.30 mmol), CuI (57 mg, 0.30 mmol), pyrazole (61 mg, 0.89 mmol), N,N'-dimethylethylenediamine ((79 mg, 0.89 mmol), potassium t-butoxide (100 mg, 0.89 mmol), and 4 mL of NMP. The reaction was heated at 150° C. for 90 min via microwave. After filtration through Celite, the reaction mixture was purified by reverse phase HPLC to afford the title compound. 1H NMR (500 MHz, (CDCl$_3$): 8.65 (d, 1H), 8.37 (d, 1H), 8.24 (d, 2H), 7.98 (broad s, 1H), 7.84 (t, 1H), 7.43 (d, 2H), 7.36 (t, 1H), 7.25 (d, 2H), 7.04 (d, 2H), 4.15 (s, 3H). LCMS: m/z 444 (M+H)+.

The examples in Table 3 were prepared following similar procedures described in Example 63 using 2-[5-[(4-chlorophenyl)thio]-4-(4-iodophenyl)-1-methyl-1H-imidazol-2-yl]pyridine (Example 61) and appropriate heterocycles as the starting materials.

TABLE 3

| Example | Compound structure | LCMS rt (min) | M + 1 |
|---|---|---|---|
| 64 | 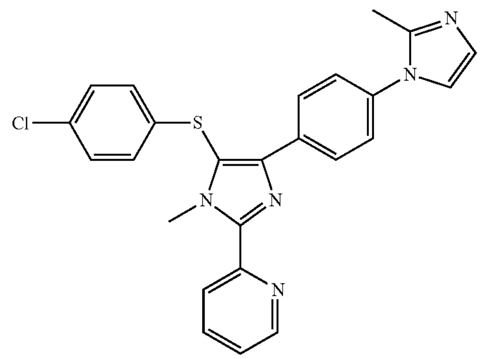 [SMILES: Cc1nccn1-c1ccc(-c2nc(-c3ccccn3)n(C)c2Sc2ccc(Cl)cc2)cc1] | 1.13 | 458 |
| 65 | 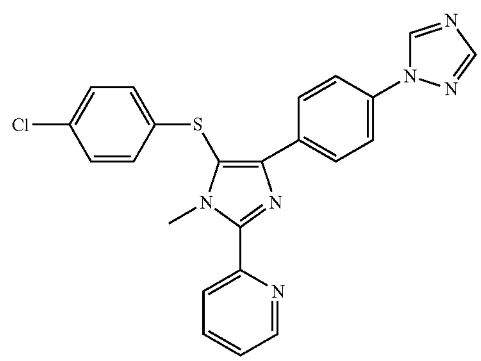 [SMILES: Cn1c(-c2ccccn2)nc(-c2ccc(-n3cncn3)cc2)c1Sc1ccc(Cl)cc1] | 1.19 | 445 |
| 66 | 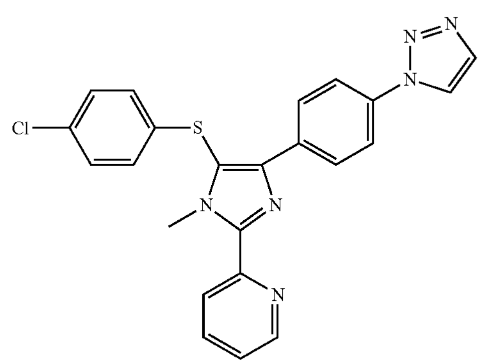 [SMILES: Cn1c(-c2ccccn2)nc(-c2ccc(-n3ccnn3)cc2)c1Sc1ccc(Cl)cc1] | 1.22 | 445 |
| 67 | 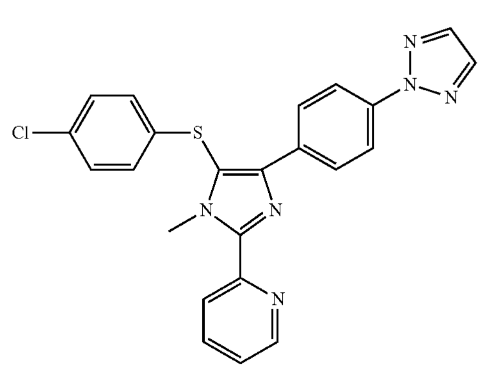 [SMILES: Cn1c(-c2ccccn2)nc(-c2ccc(-n3nccn3)cc2)c1Sc1ccc(Cl)cc1] | 1.26 | 445 |

TABLE 3-continued
| Example | Compound structure | LCMS rt (min) | M + 1 |
|---|---|---|---|
| 68 | 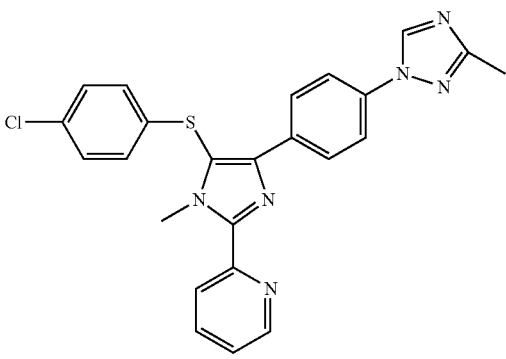 [SMILES: Cc1ncn(-c2ccc(-c3nc(-c4ccccn4)n(C)c3Sc3ccc(Cl)cc3)cc2)n1] | 1.19 | 459 |
| 69 | 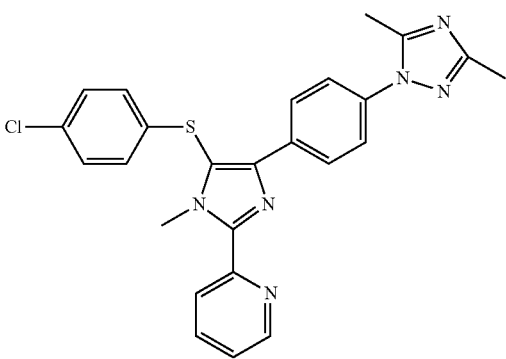 [SMILES: Cc1nc(C)n(-c2ccc(-c3nc(-c4ccccn4)n(C)c3Sc3ccc(Cl)cc3)cc2)n1] | 1.15 | 473 |
| 70 | 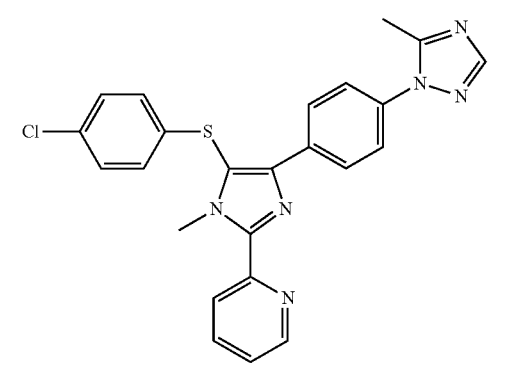 [SMILES: Cc1ncnn1-c1ccc(-c2nc(-c3ccccn3)n(C)c2Sc2ccc(Cl)cc2)cc1] | 1.19 | 459 |

Example 71

4-{5-[(4-Chlorophenyl)thio]-1-methyl-2-phenyl-1H-imidazol-4-yl}benzamide

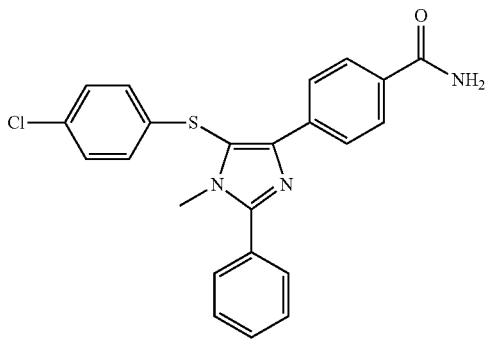

To 4-{5-[(4-chlorophenyl)thio]-1-methyl-2-phenyl-1H-imidazol-4-yl}benzonitrile (Example 2, 25 mg, 0.062 mmol) in 2 mL DMSO at 0° C. was added 1mL of 30% $H_2O_2$ (aq). A catalytic amount of $K_2CO_3$ was added and the reaction was stirred at 50° C. for 60 min. The reaction mixture was diluted with MeOH and the product was purified by reverse phase HPLC. The fractions containing the product were collected and diluted with EtOAc, washed with aq $NaHCO_3$, water, and brine. The organic layer was dried over $MgSO_4$, filtered, and concentrated to afford the title compound. 1H NMR (500 MHz, (CDCl$_3$): 8.23 (d, 2H), 7.84 (d, 2H), 7.78 (m, 2H), 7.58 (m, 3H), 7.28 (d, 2H), 7.08 (d, 2H), 6.23 (broad s, 1H), 5.82 (broad s, 1H), 3.72 (s, 3H). LCMS: m/z 420 (M+H)+.

Example 72

3-(4-{5-[(4-Chlorophenyl)thio]-1-methyl-2-phenyl-1H-imidazol-4-yl}phenyl)-1,2,4-oxadiazole

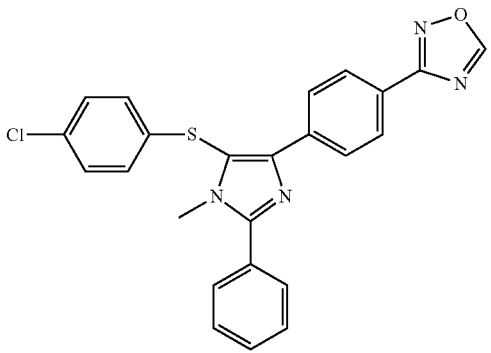 [SMILES: Cn1c(-c2ccccc2)nc(-c2ccc(-c3ncon3)cc2)c1Sc1ccc(Cl)cc1]

To 4-{5-[(4-chlorophenyl)thio]-1-methyl-2-phenyl-1H-imidazol-4-yl}benzonitrile (Example 2, 30 mg, 0.075 mmol) in 2 mL EtOH was added 0.25 mL of $HONH_2$ and catalytic amount of $K_2CO_3$. The reaction was heated at 120° C. for 60 min via microwave. The reaction mixture was concentrated to dryness and the residue was dissolved in 5 mL triethylorthoformate. Catalytic amount of TFA was added and the reaction was heated at 130° C. for 3 h. The volatiles were removed and the residue was purified by reverse phase HPLC to afford the title compound. 1H NMR (500 MHz, (CDCl$_3$): 8.74 (s, 1H), 8.27 (d, 2H), 8.18 (d, 2H), 7.72 (m, 2H), 7.53 (m, 3H), 7.25 (d, 2H), 7.06 (d, 2H), 3.68 (s, 3H). LCMS: m/z 445 (M+H)+.

Example 73

2-(4-{5-[(4-Chlorophenyl)thio]-1-methyl-2-phenyl-1H-imidazol-4-yl}phenyl)propan-2-ol

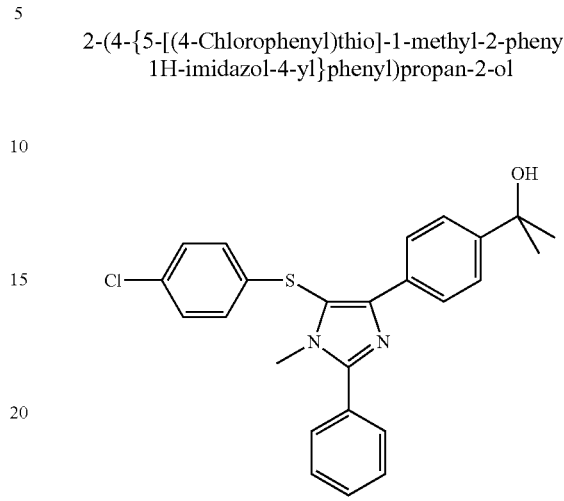

Step 1. To 4-{5-[(4-chlorophenyl)thio]-1-methyl-2-phenyl-1H-imidazol-4-yl}benzonitrile (Example 2, 35 mg, 0.087 mmol) in 0.75 mL of THF was added MeMgBr (3M in ether, 0.44 mmol) at 0° C. After heating at reflux for 2 hr, the reaction was cooled to rt and 5 mL 2N HCl was added, and was stirred for another hour. The reaction was quenched with aqueous sodium bicarbonate (pH=ca 7). The product was extracted with EtOAc, the combined extracts were washed with water and brine, dried over $MgSO_4$, filtered, and concentrated to dryness to give 1-(4-{5-[(4-chlorophenyl)thio]-1-methyl-2-phenyl-1H-imidazol-4-yl}phenyl)ethanone, which was used in the next step without further purification.

Step 2. To the crude product of Step 1 in 1 mL of THF was added 0.1 mmol of MeMgBr (3M in ether) at −78° C. After stirring at 0° C. for 1 hr, the reaction was quenched with aqueous $NH_4Cl$, and the product was extracted with EtOAc. The combined extracts were concentrated and the crude product was purified by reverse phase HPLC to afford the title compound. 1H NMR (500 MHz, (CDCl$_3$): 8.04 (d, 2H), 7.68 (m, 2H), 7.54 (d, 2H), 7.53 (m, 3H), 7.26 (d, 2H), 7.06 (d, 2H), 3.67 (s, 3H), 1.61 (s, 6H). LCMS: m/z 435 (M+H)+.

Example 74

4-{5-[(4-Chlorophenyl)thio]-1-methyl-2-phenyl-1H-imidazol-4-yl}benzoic acid

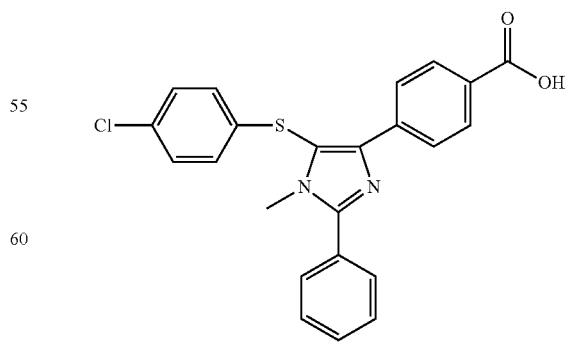

A mixture of 4-{5-[(4-Chlorophenyl)thio]-1-methyl-2-phenyl-1H-imidazol-4-yl}benzonitrile (Example 2, 120 mg, 0.299 mmol) in 4 mL of EtOH and 4 mL of 2 N NaOH was stirred at 90° C. for 4 h. The mixture was neutralized with 2 N HCl (pH=ca 5) and the product was extracted with EtOAc. The organic layer was concentrated to dryness, then the residue was purified by reverse phase HPLC to afford the title compound. 1H NMR (500 MHz, (CD$_3$OD): 8.02 (m, 4H), 7.73 (m, 2H), 7.68 (m, 3H), 7.32 (d, 2H), 7.09 (d, 2H), 3.67 (s, 3H). LCMS: m/z 421 (M+H)+.

Example 75

5-(4-{5-[(4-Chlorophenyl)thio]-1-methyl-2-phenyl-1H-imidazol-4-yl}phenyl)-1H-1,2,4-triazole

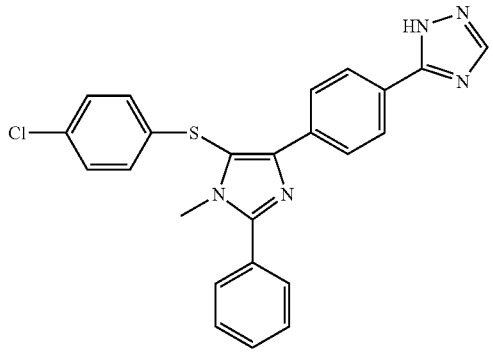 [SMILES: Cn1c(-c2ccccc2)nc(-c2ccc(-c3ncn[nH]3)cc2)c1Sc1ccc(Cl)cc1]

Step 1. A mixture of 4-{5-[(4-chlorophenyl)thio]-1-methyl-2-phenyl-1H-imidazol-4-yl}benzamide (Example 71, 35 mg, 0.083 mmol) in 3 mL of dimethylformamide-dimethylacetal was heated at 120° C. for 30 min. The volatiles were removed to afford 4-{5-[(4-chlorophenyl)thio]-1-methyl-2-phenyl-1H-imidazol-4-yl}-N-[(1E)-(dimethylamino)methylene]benzamide, which was used in the next step without further purification.

Step 2. A mixture of the crude product of Step 1, 2 mL of acetic acid and 0.15 mL of anhydrous hydrazine was stirred at 90° C. for 30 min. The reaction mixture was diluted with MeOH and was purified by reverse phase HPLC to afford the title compound. 1H NMR (500 MHz, (CD$_3$OD): 8.08 (s, 1H), 8.05 (m, 4H), 7.73 (m, 2H), 7.58 (m, 3H), 7.35 (d, 2H), 7.11 (d, 2H), 3.68 (s, 3H), 1.61 (s, 6H). LCMS: m/z 421 (M+H)+.

Example 76

2-(4-{5-[(4-Chlorophenyl)thio]-1-methyl-2-phenyl-1H-imidazol-4-yl}phenyl)-2-methylpropanenitrile

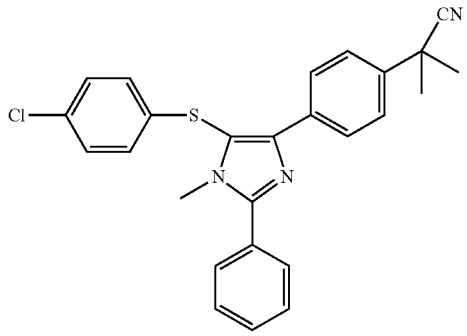 [SMILES: Cn1c(-c2ccccc2)nc(-c2ccc(C(C)(C)C#N)cc2)c1Sc1ccc(Cl)cc1]

Step 1. To 2-(4-{5-[(4-chlorophenyl)thio]-1-methyl-2-phenyl-1H-imidazol-4-yl}phenyl)propan-2-ol (Example 73, 300 mg, 0.69 mmol) in 4 mL of pyridine and 4 mL of acetic anhydride was added catalytic amount of DMAP. After stirring at 60° C. for 2 hr, the reaction was diluted with EtOAc, washed with water and brine, dried over MgSO$_4$, filtered, and concentrated to dryness to afford 1-(4-{5-[(4-chlorophenyl)thio]-1-methyl-2-phenyl-1H-imidazol-4-yl}phenyl)-1-methylethyl acetate which was used in the next step without further purification.

Step 2. A mixture of the product of Step 1 in 3 mL of THF and diethylaluminum cyanide (1M in THF, 6.29 mL, 6.29 mmol) was stirred at 60° C. for 1 hr. The reaction was quenched with aqueous Rochelle's salt, and the product was extracted with EtOAc. The combined extracts were concentrated and the residue was purified by reverser phase HPLC to afford the title compound. 1H NMR (500 MHz, (CD$_3$OD): 7.98 (d, 2H), 7.67 (m, 2H), 7.54 (d, 2H), 7.53 (m, 3H), 7.26 (d, 2H), 7.04 (d, 2H), 3.62 (s, 3H), 1.66 (s, 6H). LCMS: m/z 444 (M+H)+.

Example 77

2-(4-{5-[(4-Chlorophenyl)thio]-1-methyl-2-phenyl-1H-imidazol-4-yl}phenyl)-2-methylpropanamide

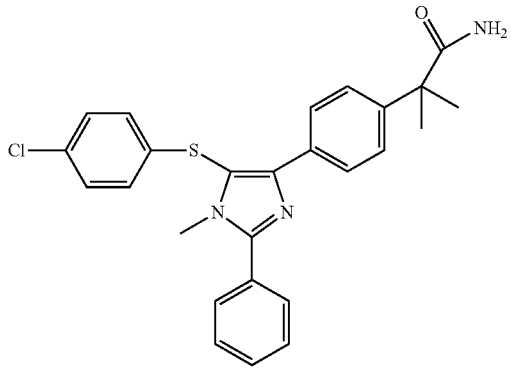 [SMILES: Cn1c(-c2ccccc2)nc(-c2ccc(C(C)(C)C(N)=O)cc2)c1Sc1ccc(Cl)cc1]

A suspension of 2-(4-{5-[(4-chlorophenyl)thio]-1-methyl-2-phenyl-1H-imidazol-4-yl}phenyl)-2-methylpropanenitrile (Example 76, 120 mg, 0.270 mmol) in 3 mL of EtOH and 2 mL of 2 N NaOH was stirred at 90° C. over two days. The mixture was neutralized with 2 N HCl (pH=ca 5) and the product was extracted with EtOAc. The extracts were concentrated to dryness, and the residue was purified by reverse phase HPLC to afford the title compound. 1H NMR (500 MHz, (CD$_3$OD): 7.88 (d, 2H), 7.74 (m, 2H), 7.58 (m, 3H), 7.44 (d, 2H), 7.26 (d, 2H), 7.31 (d, 2H), 3.64 (s, 3H), 1.58 (s, 6H). LCMS: m/z 462 (M+H)+.

Example 78

5-{5-[(4-Chlorophenyl)thio]-1-methyl-2-pyridin-2-yl-1H-imidazol-4-yl}pyridine-2-carbonitrile

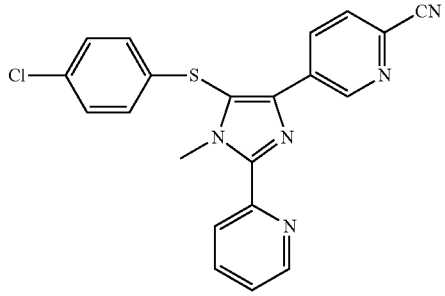

Step 1. 2-Bromo-5-(2-pyridin-2-yl-1H-imidazol-4-yl)pyridine was prepared from Intermediate 4 and 2-pyridylamidine HCl salt following the procedure described in Step 1 of Example 1. LCMS: m/z 301 (M+H)+.

Step 2. 2-Bromo-5-(2-pyridin-2-yl-1H-imidazol-4-yl)pyridine (Step 1, 1.2 g, 3.98 mmol), Zn(CN)$_2$ (0.56 g, 4.78 mmol), Pd$_2$(dba)$_3$ (0.58 g, 0.638 mmol), and DPPF (0.88 g, 1.6 mmol) were charged to a flask that was flushed with N$_2$. Wet DMF (DMF:water 99:1 v/v, 14 mL) was added, and nitrogen was bubbled through the solution for 30 min. The resulting mixture was heated at 120° C. overnight. After cooling, the reaction mixture was filtered through Celite, and the product was purified by reverse phase HPLC to afford 2-cyano-5-(2-pyridin-2-yl-1H-imidazol-4-yl)pyridine. LCMS: m/z 248 (M+H)+.

Step 3. Starting with 2-cyano-5-(2-pyridin-2-yl-1H-imidazol-4-yl)pyridine (Step 2) and following the procedure described in Step 2 of Example 1, 5-(5-iodo-2-pyridin-2-yl-1H-imidazol-4-yl)pyridine-2-carbonitrile was prepared. LCMS: m/z 374 (M+H)+.

Step 4. Starting with 5-(5-iodo-2-pyridin-2-yl-1H-imidazol-4-yl)pyridine-2-carbonitrile (Step 3) and following the procedure described in Step 3 of Example 1, 5-{5-[(4-chlorophenyl)thio]-2-pyridin-2-yl-1H-imidazol-4-yl}pyridine-2-carbonitrile was prepared. LCMS: ink 390 (M+H)+.

Step 5. Starting with 5-{5-[(4-chlorophenyl)thio]-2-pyridin-2-yl-1H-imidazol-4-yl}pyridine-2-carbonitrile (compound of Step 4) and following the procedure described in Example 2, the title compound was prepared. 1H NMR (500 MHz, (CDCl$_3$): 9.57 (s, 1H), 8.68 (d, 1H), 8.60 (d, 1H), 8.37 (d, 1H), 7.88 (t, 1H), 7.74 (d, 1H), 7.38 (dd, 1H), 7.24 (d, 2H), 7.02 (d, 2H), 4.17 (s, 3H). LCMS: m/z 404 (M+H)+.

Example 79

6-{5-[(4-chlorophenyl)thio]-1-methyl-2-pyridin-2-yl-1H-imidazol-4-yl}nicotinonitrile

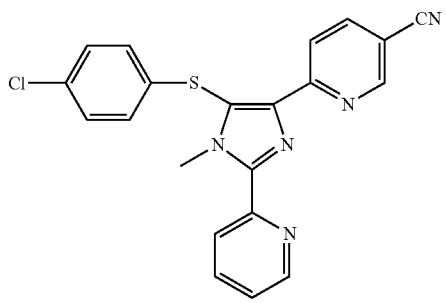 [SMILES: Cn1c(-c2ccccn2)nc(-c2ccc(C#N)cn2)c1Sc1ccc(Cl)cc1]

Starting with Intermediate 5 and 2-pyridylamidine HCl salt, the title compound was prepared following the procedure described in Example 2. 1H NMR (500 MHz, (CDCl$_3$): 8.98 (s, 1H), 8.67 (d, 1H), 8.41 (d, 1H), 8.38 (d, 1H), 7.98 (t, 1H), 7.84 (d, 1H), 7.38 (dd, 1H), 7.26 (d, 2H), 7.12 (d, 2H), 4.18 (s, 3H). LCMS: m/z 404 (M+H)+.

The examples in Table 4 were prepared using the procedures and starting materials shown in the table.

TABLE 4

| Example | Starting materials and Procedures followed | Compound structure | LCMS Rt (min) | [M + 1] |
|---|---|---|---|---|
| 80 | Starting with compound of Example 10 and following the procedure described for Example 72. | 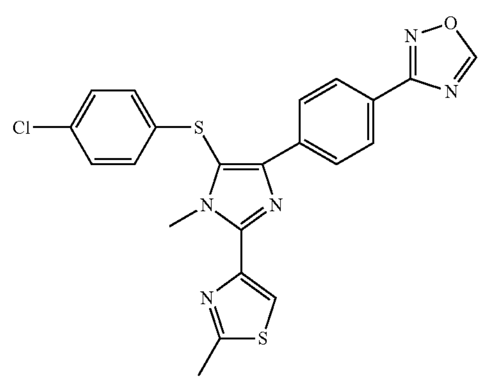 [SMILES: Cc1nc(-c2nc(-c3ccc(-c4ncon4)cc3)c(Sc3ccc(Cl)cc3)n2C)cs1] | 1.25 | 466 |
| 81 | Starting with compound of Example 23 and following the procedure described for Example 72. | 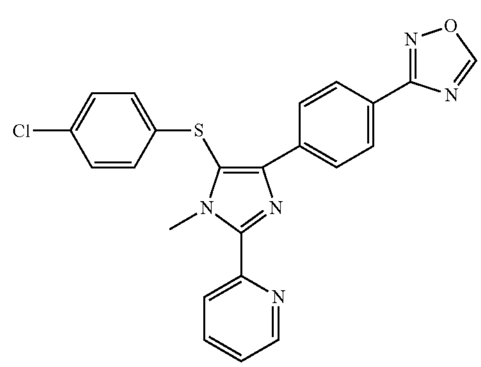 [SMILES: Cn1c(-c2ccccn2)nc(-c2ccc(-c3ncon3)cc2)c1Sc1ccc(Cl)cc1] | 1.30 | 446 |

TABLE 4-continued

| Example | Starting materials and Procedures followed | Compound structure | LCMS Rt (min) | [M + 1] |
|---|---|---|---|---|
| 82 | Starting with compound of Example 23 and following the procedure described for Example 72. | 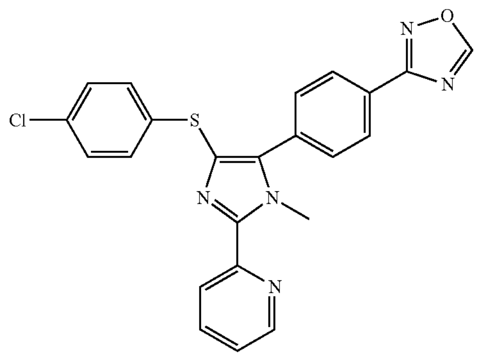 [SMILES: Cn1c(-c2ccccn2)nc(Sc2ccc(Cl)cc2)c1-c1ccc(-c2ncon2)cc1] | 1.30 | 446 |
| 83 | Starting with compound of Example 23 and following the procedure described for Example 71. | 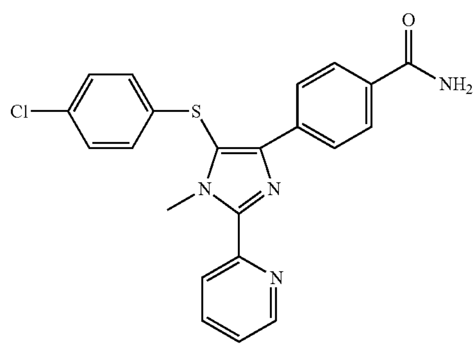 [SMILES: Cn1c(-c2ccccn2)nc(-c2ccc(C(N)=O)cc2)c1Sc1ccc(Cl)cc1] | 1.18 | 421 |
| 84 | Starting with compound of Example 23 and following the procedure described for Example 71. | 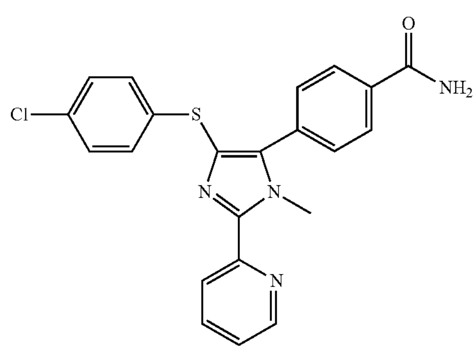 [SMILES: Cn1c(-c2ccccn2)nc(Sc2ccc(Cl)cc2)c1-c1ccc(C(N)=O)cc1] | 1.18 | 421 |
| 85 | Starting with compound of Example 23 and following the procedure described for Example 73. | 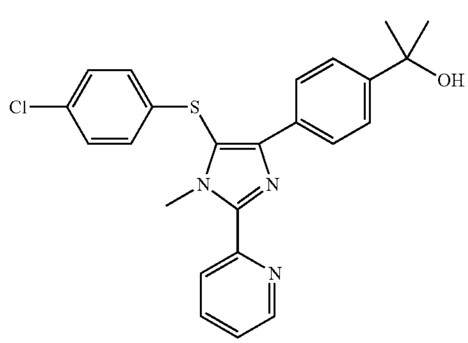 [SMILES: Cn1c(-c2ccccn2)nc(-c2ccc(C(C)(C)O)cc2)c1Sc1ccc(Cl)cc1] | 1.27 | 436 |

TABLE 4-continued

| Example | Starting materials and Procedures followed | Compound structure | LCMS Rt (min) | [M + 1] |
|---|---|---|---|---|
| 86 | Starting with compound of Example 23 and following the procedure described for Example 73. | 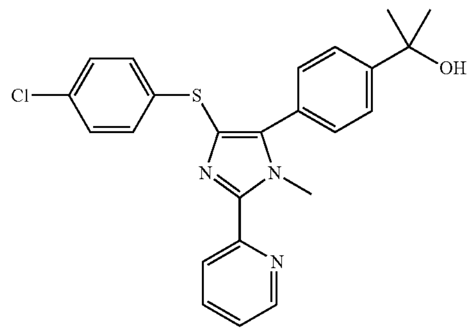 [SMILES: Cn1c(-c2ccccn2)nc(Sc2ccc(Cl)cc2)c1-c1ccc(C(C)(C)O)cc1] | 1.27 | 436 |
| 87 | Procedure of Example 72. | 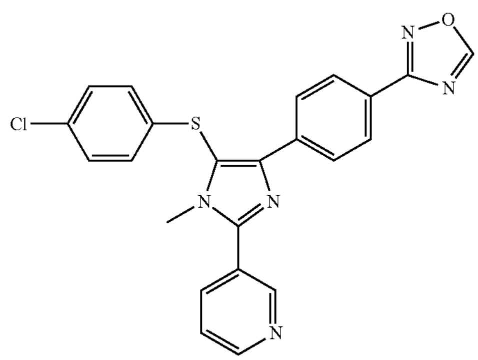 [SMILES: Cn1c(-c2cccnc2)nc(-c2ccc(-c3ncon3)cc2)c1Sc1ccc(Cl)cc1] | 1.29 | 446 |
| 88 | Procedure of Example 71. | 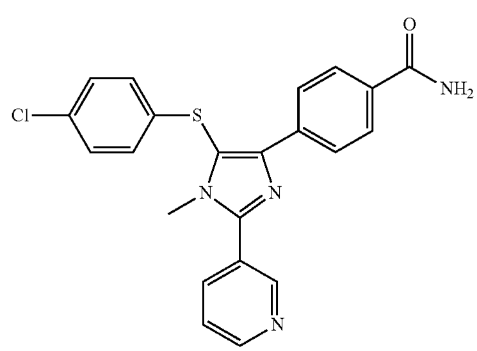 | 1.18 | 421 |
| 89 | Procedure of Example 72. | 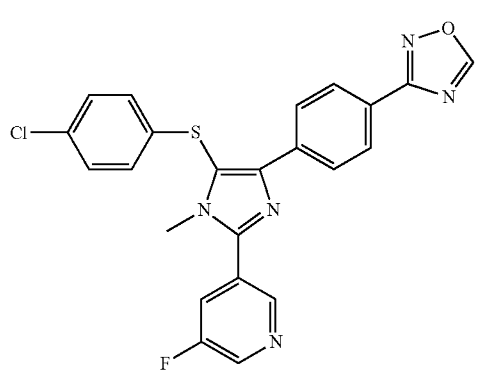 [SMILES: Cn1c(-c2cncc(F)c2)nc(-c2ccc(-c3ncon3)cc2)c1Sc1ccc(Cl)cc1] | 1.28 | 464 |

TABLE 4-continued

| Example | Starting materials and Procedures followed | Compound structure | LCMS Rt (min) | [M + 1] |
|---|---|---|---|---|
| 90 | Starting with compound of Example 19 and following the procedure described for Example 72. | 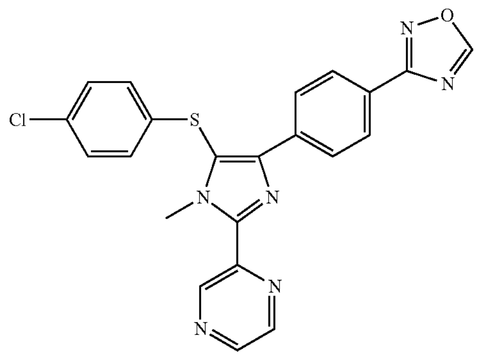 | 1.30 | 447 |
| 91 | Procedure of Example 72. | 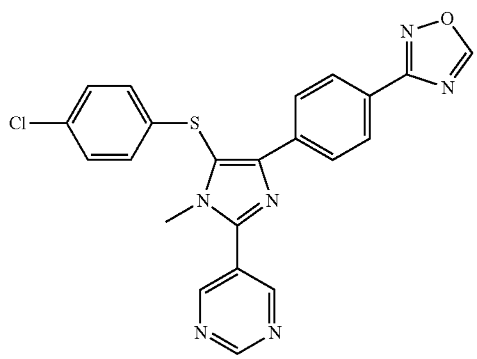 [SMILES: Cn1c(-c2cncnc2)nc(-c2ccc(-c3ncon3)cc2)c1Sc1ccc(Cl)cc1] | 1.28 | 447 |
| 92 | Starting with compound of Example 22 and following the procedure described for Example 71. | 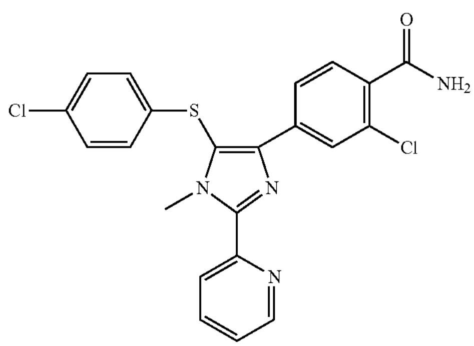 [SMILES: Cn1c(-c2ccccn2)nc(-c2ccc(C(N)=O)c(Cl)c2)c1Sc1ccc(Cl)cc1] | 1.33 | 455 |
| 93 | Starting with compound of Example 22 and following the procedure described for Example 73. | 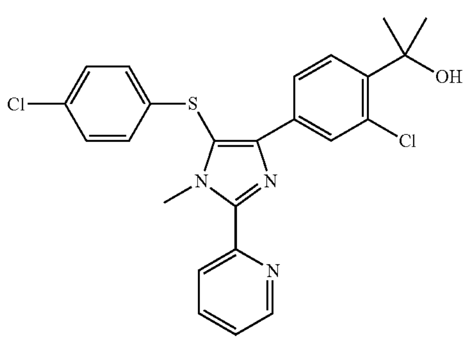 [SMILES: Cn1c(-c2ccccn2)nc(-c2ccc(C(C)(C)O)c(Cl)c2)c1Sc1ccc(Cl)cc1] | 1.37 | 470 |

TABLE 4-continued

| Example | Starting materials and Procedures followed | Compound structure | LCMS Rt (min) | [M + 1] |
|---|---|---|---|---|
| 94 | 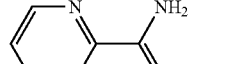 Procedure of Example 73. | 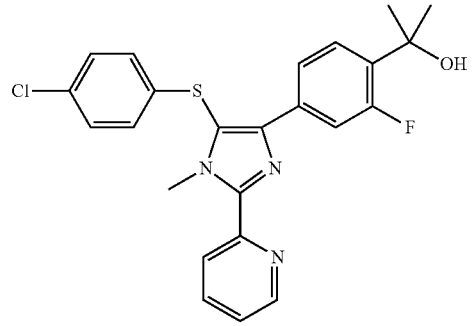 [SMILES: Cn1c(-c2ccccn2)nc(-c2ccc(C(C)(C)O)c(F)c2)c1Sc1ccc(Cl)cc1] | 1.26 | 454 |
| 95 | Starting with compound of Example 78 and following the procedure described for Example 73. | 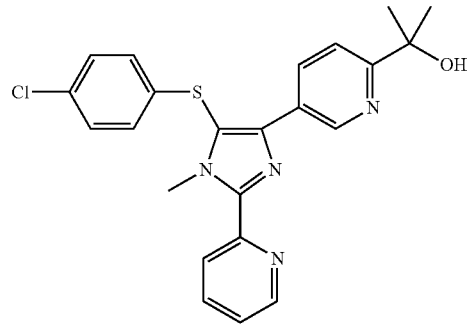 | 1.13 | 437 |
| 96 | Starting with compound of Example 79 and following the procedure described for Example 73. | 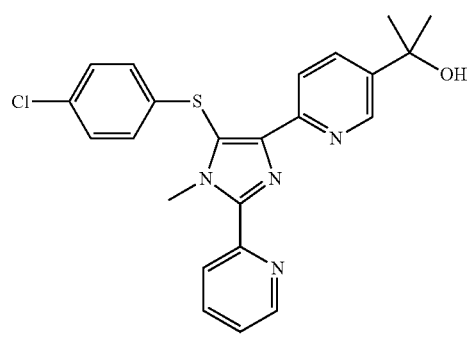 | 1.15 | 437 |
| 97 | Starting with compound of Example 79 and following the procedure described for Example 72. | 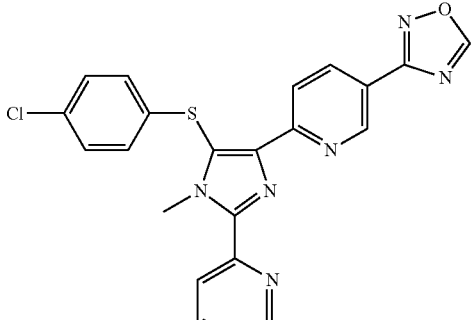 | 1.20 | 447 |

Example 98

4-{5-[(4-Chlorophenyl)thio]-1-methyl-2-pyridin-2-yl-1H-imidazol-4-yl}aniline

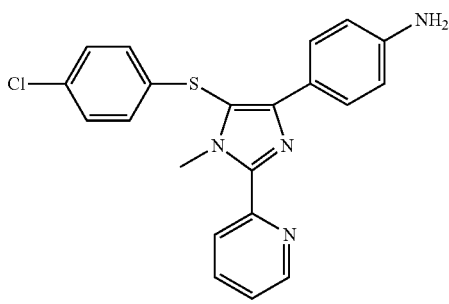 [SMILES: Cn1c(-c2ccccn2)nc(-c2ccc(N)cc2)c1Sc1ccc(Cl)cc1]

2-{4-(4-Bromophenyl)-5-[(4-chlorophenyl)thio]-1-methyl-1H-imidazol-2-yl}pyridine (Example 15, 300 mg, 0.57 mmol), Pd(dba)$_2$ (19 mg, 0.03 mmol), and biphenyl-PCy$_2$ (11.5 mg, 0.03 mmol) were charged into a flask that was flushed with nitrogen. Toluene (2.2 mL) was added, followed by LiHMDS (1M in PhMe, 2 mL, 2 mmol). After heating at 75° C. overnight, the reaction was quenched with aqueous NH$_4$Cl and diluted with EtOAc. The organic layer was washed with water and brine. The volatiles were evaporated and the residue was purified by reverse phase HPLC to afford the title compound. 1H NMR (500 MHz, (CD$_3$OD): 8.58 (broads, 1H), 8.18 (broad s, 1H), 7.98 (t, 1H), 8.27 (d, 2H), 7.68 (d, 2H), 7.46 (broad s, 7.07 (d, 2H), 6.78 (d, 2H), 3.98 (s, 3H). LCMS: m/z 393 (M+H)+.

Example 99

2-{5-[(4-Chlorophenyl)thio]-1-methyl-4-[4-(2-methyl-2H-tetrazol-5-yl)phenyl]-1H-imidazol-2-yl}pyridine

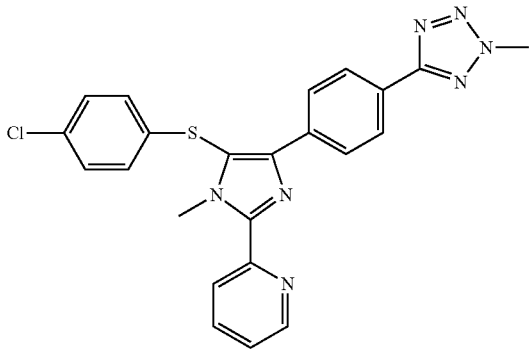 [SMILES: Cn1nnc(-c2ccc(-c3nc(-c4ccccn4)n(C)c3Sc3ccc(Cl)cc3)cc2)n1]

Step 1. A solution of 2-{4-(4-cyanophenyl)-5-[(4-chlorophenyl)thio]-1-methyl-1H-imidazol-2-yl}pyridine (Example 23, 160 mg, 0.41 mmol) and azidotrimethyltin (420 mg, 2.0 mmol) in xylene (1.5 mL) was heated at 140° C. under nitrogen for 2 hrs. After cooling, the reaction mixture was filtered through a pad of Celite and silica, and the filtrate was concentrated to afford 2-{5-[(4-Chlorophenyl)thio]-1-methyl-4-[4-(2H-tetrazol-5-yl)phenyl]-1H-imidazol-2-yl}pyridine, which was used in the next step without further purification.

Step 2. To the product of Step 1 in 1.5 mL of DMF was added K$_2$CO$_3$ (85 mg, 0.61 mmol). After stirring at rt for 30 min, MeI (0.05 mL, 0.82 mmol) was added and stirring continued for 1.5 h. The reaction mixture was diluted with MeOH/MeCN, and the precipitate was collected by filtration to give the title compound. 1H NMR (500 MHz, (CDCl$_3$): 8.44 (d, 1H), 8.39 (d, 1H), 8.27 (d, 2H), 8.19 (d, 2H), 7.88 (t, 1H), 7.36 (dd, 1H), 7.26 (d, 2H), 7.07 (d, 2H), 4.42 (s, 3H), 4.15 (s, 3H). LCMS: m/z 460 (M+H)+.

Example 100

5-Chloro-2-({1-methyl-4-[6-(methylsulfonyl)pyridin-3-yl]-2-pyridin-2-yl-1H-imidazol-5-yl}thio)pyridine

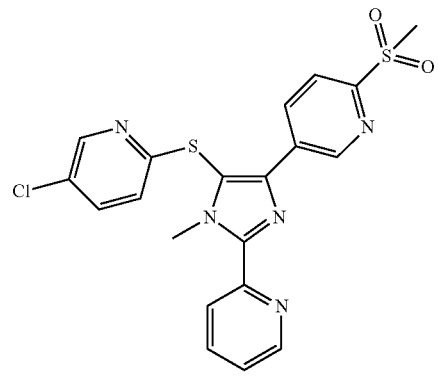 [SMILES: Cn1c(-c2ccccn2)nc(-c2ccc(S(C)(=O)=O)nc2)c1Sc1ccc(Cl)cn1]

Step 1: 1-(6-Bromopyridin-3-yl)ethanone was dissolved in 50 mL of chloroform and cooled to 0° C., to which was added catalytic amount of AlCl$_3$ and 2.65 mL of bromine in 25 mL of chloroform. The addition of bromine lasted 1 h to keep the reaction solution at 0° C. After stirring at 0° C. overnight, the mixture was diluted with dichloromethane, washed with aqueous sodium bicarbonate, water, and brine. The organic layer was dried (MgSO$_4$), filtered, and concentrated to afford 2-bromo-1-(6-bromopyridin-3-yl)ethanone which was used in the next step with out further purification. LCMS: [M+1]$^+$=279.

Step 2: 2-Pyridinecarboximidamide HCl salt (11.7 g, 74.3 mmol) and sodium bicarbonate (13.7 g, 163 mmol) were suspended in 100 mL of THF and 30 mL of water. The suspension was heated to reflux, to which was slowly added the product from the previous step (22.9 g, 82 mmol) in 70 mL of THF over 4 h. The reflux was continued overnight. The reaction mixture was cooled to rt, partially concentrated, and cooled in ice-water bath. The precipitate was collected by filtration, rinsed with two 50-mL portions of water, and air-dried to afford 2-bromo-5-(2-pyridin-2-yl-1H-imidazol-4-yl)pyridine. LCMS: [M+1]$^+$=300.

Step 3: The product from the previous step (21 g, 70 mmol) was dissolved in THF (160 mL), to which was added Cs$_2$CO$_3$ (29.6 g, 91 mmol) at 0° C. After stirring for 5 min, MeI (11 mL, 1 mmol) was added. After stirring overnight at rt, the reaction was quenched with aq NH$_4$Cl. The product was extracted with EtOAc and the organic layer was washed with water, brine, dried over MgSO$_4$, filtered, and concentrated. The residue was subject to silica column (0-50% EtOAc in hexanes) to give 12.5 g of 2-bromo-5-(1-methyl-2-pyridin-2-yl-1H-imidazol-4-yl)pyridine LCMS: [M+1]$^+$=315.

Step 4: To a solution of the product from the previous step (0.3 g, 0.952 mmol), excess copper (I) trifluoromethanesulfonate benzene complex, and excess sodium methanesulfinate was added excess N,N'-dimethylethane-1,2-diamine. The mixture was heated at 185° C. for 90 min via microwave irradiation. Water was added and the mixture was extracted with ethyl acetate. The organics were dried (MgSO$_4$) and concentrated to afford 1-methyl-4-[4-(methylsulfonyl)phenyl]-2-phenyl-1H-imidazole which was used with out further purification. LCMS: [M+1]$^+$=315.

Step 5: To a solution of Step 4 product (1.5 g, 4.77 mmol) in dichloromethane (15 mL) was added N-iodosuccinimide (1.07 mg, 4.77 mmol) and three drops trifluoroacetic acid. The reaction was stirred at rt for 3 h. The mixture was neutralized with aqueous sodium bicarbonate and the organics were extracted with dichloromethane. The organics were then washed with aqueous sodium thiosulfate, followed by three washes with water. The organics were dried (MgSO$_4$), concentrated, and purified by silica column eluting a gradient of 20-70% ethyl acetate in hexanes to give rise to the title compound as a brown solid. LCMS: [M+1]$^+$=440.

Step 6: To a dry suspension of the Step 5 product (1.2 g, 2.73 mmol), potassium carbonate (0.75 g, 5.45 mmol), copper (I) iodide (52 mg, 0.273 mmol), and Intermediate 1 (0.476 g, 3.27 mmol) in 10 mL isopropanol under an atmosphere of nitrogen was added ethylene glycol (0.3 mL, 5.45 mmol). The reaction mixture was stirred at 80° C. for 16 h. Water was added and the mixture was extracted with ethyl acetate. The organics were dried (MgSO$_4$), concentrated, and purified on silica gel column eluting a gradient of 20-100% ethyl acetate in hexanes to give rise to 5-Chloro-2-({1-methyl-4-[6-(methylsulfonyl)pyridin-3-yl]-2-pyridin-2-yl-1H-imidazol-5-yl}thio)pyridine (0.836 g, yield 67%). 1H NMR (500 MHz), [(CD$_3$)$_2$CO]: 9.43 (br, 1H), 8.78 (br, 1H), 8.45 (br, 2H), 8.07 (br, 2H), 7.81 (br, 2H), 7.3 (br, 1H), 4.23 (s, 3H), 3.22 (s, 3H). LCMS: [M+1]$^+$=458. Human FAAH lysate assay: IC$_{50}$ 48 nM.

The Examples in Table 5 were prepared following the procedures described in Example 100 using the appropriate thiol.

TABLE 5

| Example | Compound structure | LCMS rt (min) | M + 1 | hFAAH lysate IC$_{50}$ (nM) |
| --- | --- | --- | --- | --- |
| 101 | 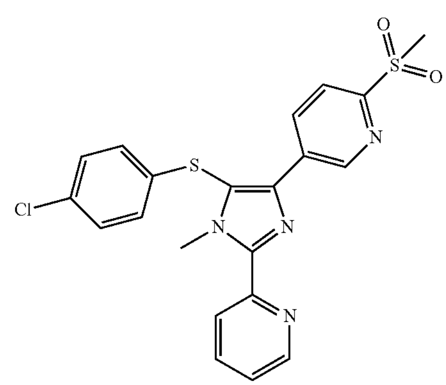 [SMILES: Cn1c(-c2ccccn2)nc(-c2ccc(S(C)(=O)=O)nc2)c1Sc1ccc(Cl)cc1] | 1.23 | 457 | 6.3 |
| 102 | 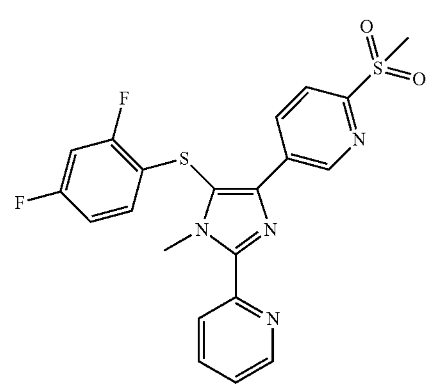 [SMILES: Cn1c(-c2ccccn2)nc(-c2ccc(S(C)(=O)=O)nc2)c1Sc1ccc(F)cc1F] | 1.21 | 459 | 15.4 |

TABLE 5-continued

| Example | Compound structure | LCMS rt (min) | M + 1 | hFAAH lysate IC$_{50}$ (nM) |
|---|---|---|---|---|
| 103 | 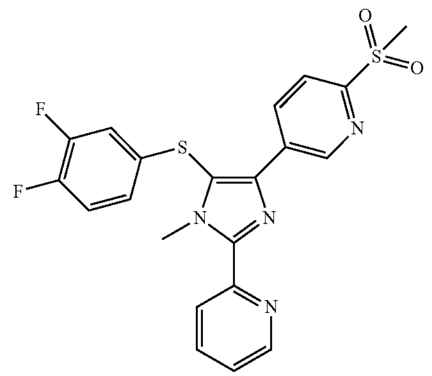 [SMILES: Cn1c(-c2ccccn2)nc(-c2ccc(S(C)(=O)=O)nc2)c1Sc1ccc(F)c(F)c1] | 1.20 | 459 | 37.6 |
| 104 | 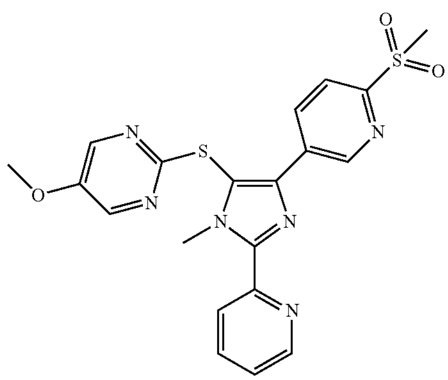 [SMILES: COc1cnc(Sc2c(-c3ccc(S(C)(=O)=O)nc3)nc(-c3ccccn3)n2C)nc1] | 1.12 | 455 | 202 |

Example 105

2-(5-{5-[(4-Chlorophenyl)thio]-1-methyl-2-pyridin-2-yl-1H-imidazol-4-yl}pyridin-2-yl)propan-2-ol

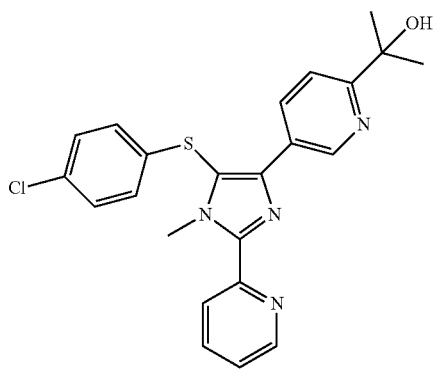

Step 1: 2-Bromo-5-(2-pyridin-2-yl-1-methylimidazol-4-yl)pyridine (Example 100, Step 3 product, 1.2 g, 3.98 mmol), Zn(CN)$_2$ (0.56 g, 4.78 mmol), Pd$_2$(dba)$_3$ (0.58 g, 0.638 mmol), and DPPF (0.88 g, 1.6 mmol) were charged to a flask that was degassed and then filled with N$_2$ (repeated three times). Wet DMF (DMF:water 99:1 v/v, 14 mL) was added, and nitrogen was bubbled through the solution for 30 min. The reaction was heated at 120° C. overnight. After cooling, the reaction mixture was filtered through Celite, and the product was purified by reverse phase HPLC to afford 2-cyano-5-(2-pyridin-2-yl-1H-imidazol-4-yl)pyridine. LCMS: m/z 248 (M+H)+.

Step 2: Starting with the product from the previous step and following the procedure described in Step 5 of Example 100, 5-(5-iodo-2-pyridin-2-yl-1-methyl-1H-imidazol-4-yl)pyridine-2-carbonitrile was prepared. LCMS: m/z 388 (M+H)+.

Step 3: Starting with the product from the previous step and the 4-chlorophenylthiol and following the procedure described in Step 6 of Example 100, 5-{5-[(4-Chlorophenyl)thio]-1-methyl-2-pyridin-2-yl-1H-imidazol-4-yl}pyridine-2-carbonitrile was prepared. 1H NMR (500 MHz, (CDCl$_3$): 9.57 (s, 1H), 8.68 (d, 1H), 8.60 (d, 1H), 8.37 (d, 1H), 7.88 (t, 1H), 7.74 (d, 1H), 7.38 (dd, 1H), 7.24 (d, 2H), 7.02 (d, 2H), 4.17 (s, 3H). LCMS: m/z 404 (M+H)+.

Step 4: To the product from the previous step (35 mg, 0.087 mmol) in 0.75 mL of THF was added MeMgBr (3M in ether, 0.44 mmol) at 0° C. After heated at reflux for 2 hr, the reaction was cooled to rt and 5 mL 2N HCl was added. After stirring at rt for 1 hr, the reaction was neutralized with aqueous sodium bicarbonate. The product was extracted with EtOAc, the combined extracts were washed with water and brine, dried over MgSO$_4$, filtered, and concentrated to dryness to give 1-(5-{5-[(4-chlorophenyl)thio]-1-methyl-2-pyridin-2-yl-1H-imidazol-4-yl}pyridin-2-yl)ethanone, which was used in the next step without further purification. LCMS: m/z 421 (M+H)+.

Step 5: To the crude product from the previous step in 1 mL of THF was added 0.1 mmol of MeMgBr (3M in ether) at −78° C. After stirring at 0° C. for 1 hr, the reaction was quenched with aqueous NH$_4$Cl, and the product was extracted with EtOAc. The organic layer was concentrated and the crude product was purified by reverse phase HPLC to afford the title compound. 1H NMR (500 MHz, (CDCl$_3$): 9.22 (d, 1H), 8.70 (br, 1H), 8.42 (br, 1H), 8.38 (m, 1H), 7.90 (m, 1H), 7.40 (d, 1H), 7.35 (d, 1H), 7.25 (d, 2H), 7.10 (d, 2H), 4.15 (s, 6H). LCMS: m/z 437 (M+H)+. Human FAAH lysate assay: IC$_{50}$=37.8 nM.

The Examples in Table 6 were prepared following the procedure described in Example 105.

TABLE 6

| Example | Compound structure | LCMS rt (min) | M + 1 | hFAAH lysate IC$_{50}$ (nM) |
|---------|-------------------|---------------|-------|------------------------------|
| 106 | 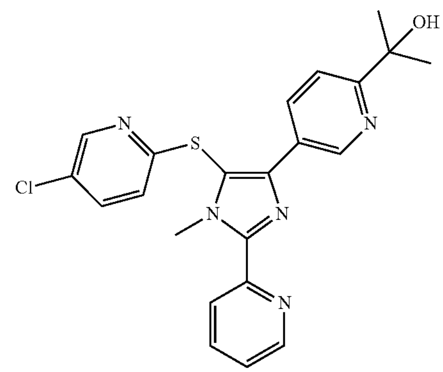 [SMILES: Cn1c(-c2ccccn2)nc(-c2ccc(C(C)(C)O)nc2)c1Sc1ccc(Cl)cn1] | 1.03 | 438 | 37.8 |
| 107 | 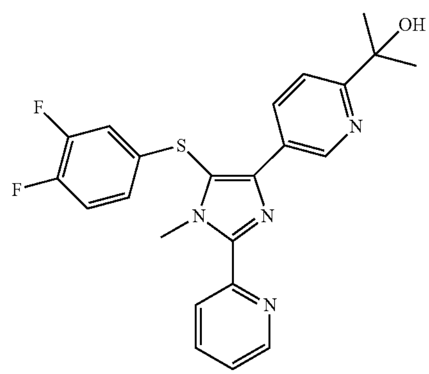 [SMILES: Cn1c(-c2ccccn2)nc(-c2ccc(C(C)(C)O)nc2)c1Sc1ccc(F)c(F)c1] | 1.07 | 439 | 60.2 |
| 108 | 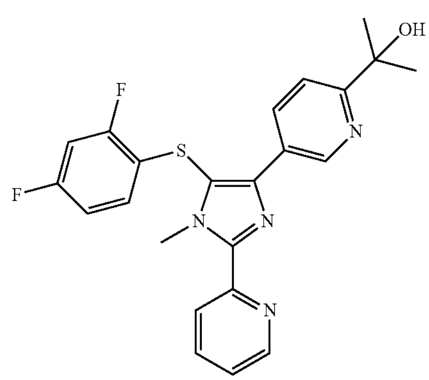 [SMILES: Cn1c(-c2ccccn2)nc(-c2ccc(C(C)(C)O)nc2)c1Sc1ccc(F)cc1F] | 1.06 | 439 | 33.2 |

TABLE 6-continued

| Example | Compound structure | LCMS rt (min) | M + 1 | hFAAH lysate IC$_{50}$ (nM) |
|---|---|---|---|---|
| 109 | 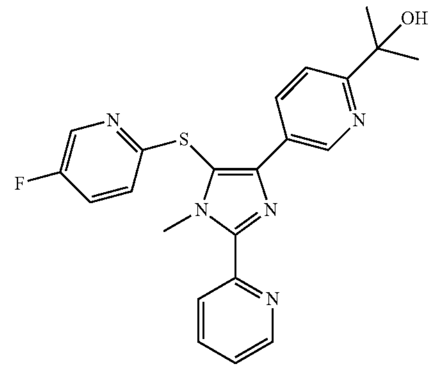 [SMILES: Cn1c(-c2ccccn2)nc(-c2ccc(C(C)(C)O)nc2)c1Sc1ccc(F)cn1] | 0.99 | 422 | 133.6 |
| 110 | 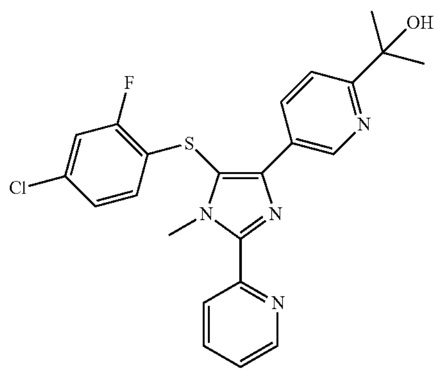 [SMILES: Cn1c(-c2ccccn2)nc(-c2ccc(C(C)(C)O)nc2)c1Sc1ccc(Cl)cc1F] | 1.10 | 455 | 33.7 |
| 111 | 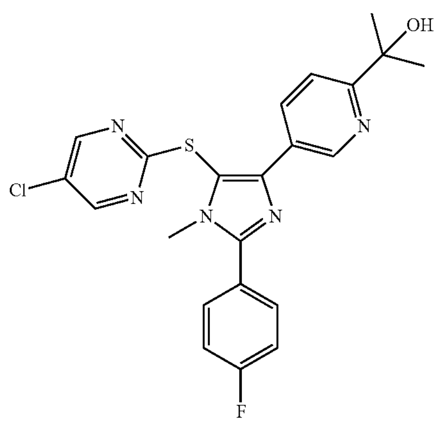 [SMILES: Cn1c(-c2ccc(F)cc2)nc(-c2ccc(C(C)(C)O)nc2)c1Sc1ncc(Cl)cn1] | 1.00 | 455 | 122.7 |
| 112 | 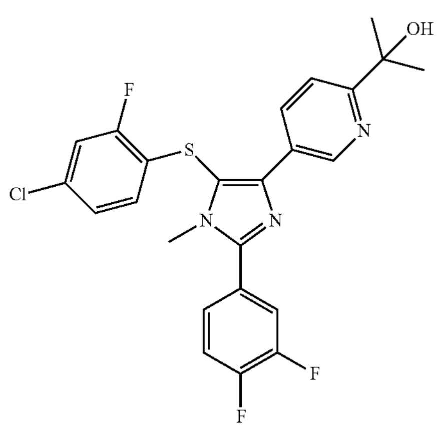 [SMILES: Cn1c(-c2ccc(F)c(F)c2)nc(-c2ccc(C(C)(C)O)nc2)c1Sc1ccc(Cl)cc1F] | 1.20 | 490 | 113.9 |

TABLE 6-continued

| Example | Compound structure | LCMS rt (min) | M + 1 | hFAAH lysate IC$_{50}$ (nM) |
|---|---|---|---|---|
| 113 | 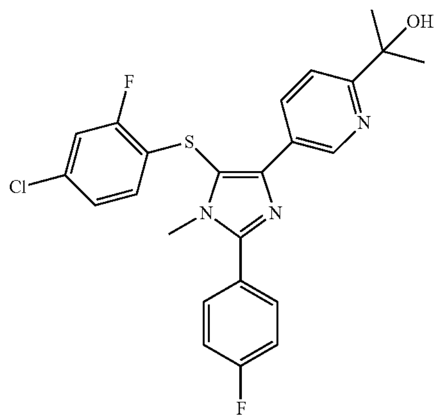 [SMILES: Cn1c(-c2ccc(F)cc2)nc(-c2ccc(C(C)(C)O)nc2)c1Sc1ccc(Cl)cc1F] | 1.10 | 472 | 67.9 |
| 114 | 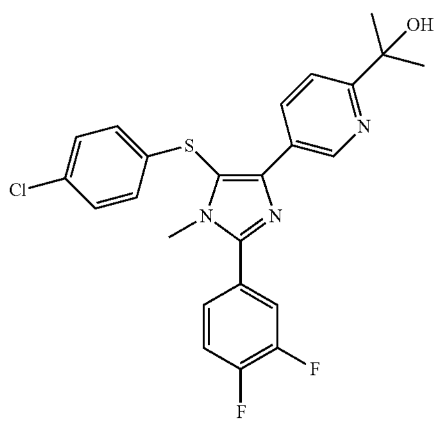 [SMILES: Cn1c(-c2ccc(F)c(F)c2)nc(-c2ccc(C(C)(C)O)nc2)c1Sc1ccc(Cl)cc1] | 1.10 | 472 | 87.4 |
| 115 | 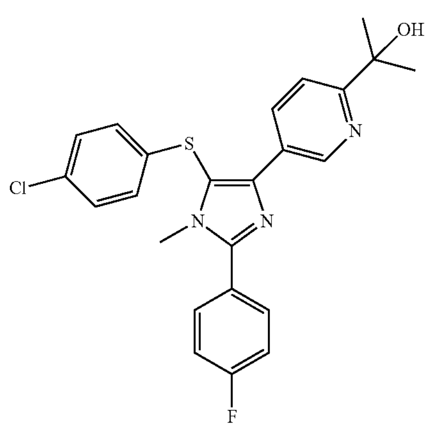 [SMILES: Cn1c(-c2ccc(F)cc2)nc(-c2ccc(C(C)(C)O)nc2)c1Sc1ccc(Cl)cc1] | 1.00 | 454 | 67 |

Example 116

5-[(4-chlorophenyl)thio]-4-[4-(2-furyl)phenyl]-1-methyl-2-pyridin-2-yl-1H-imidazol-3-ium trifluoroacetate

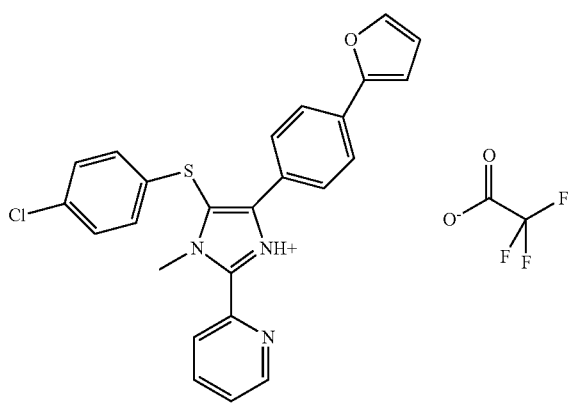 [SMILES: Cn1c(-c2ccccn2)[nH+]c(-c2ccc(-c3ccco3)cc2)c1Sc1ccc(Cl)cc1 ; O=C([O-])C(F)(F)F]

A mixture of 2-{4-(4-bromophenyl)-5-[(4-chlorophenyl)thio]-1-methyl-1H-imidazol-2-yl}pyridine (Example 15, 200 mg, 0.438 mmol), 2-furylboronic acid (49 mg, 0.438 mmol), bis(triphenylphosphine)palladium (II) chloride (50 mg, 0.044 mmol), was suspended in THF (3 mL) and sodium carbonate (1 mL of 1 M aqueous solution). The reaction was heated at 150° C. for 45 min via microwave irradiation. Water was added and the mixture was extracted with ethyl acetate. The organics were dried (MgSO$_4$) and concentrated. The residue was purified by reverse phase HPLC to afford the title compound (3 mg, 1.22%). $^1$H NMR (500 MHz, (CD$_3$)$_2$CO): δ 8.71 (d, 1H), 8.40 (m, 1H), 8.23 (d, 2H), 8.00 (m, 1H), 7.76 (d, 2H), 7.64 (d, 1H), 7.46 (m, 1H), 7.36 (d, 2H), 7.20 (d, 2H), 6.88 (d, 1H), 6.57 (d, 1H) 4.20 (s, 3H). LCMS: m/z 444.1 (M+H)+. Human FAAH lysate assay: IC$_{50}$=17.5 nM.

The examples in Table 7 were prepared according to the procedure described for Example 116 using the appropriate boronic acid and either 2-{4-(4-bromophenyl)-5-[(4-chlorophenyl)thio]-1-methyl-1H-imidazol-2-yl}pyridine (Example 15) or the analagously prepared 2-{[4-(4-bromophenyl)-1-methyl-2-pyridin-2-yl-1H-imidazol-5-yl]thio}-5-chloropyridine as starting materials.

TABLE 7

| Example | Compound structure | LCMS rt (min) | M + 1 | hFAAH lysate IC$_{50}$ (nM) |
|---|---|---|---|---|
| 117 | 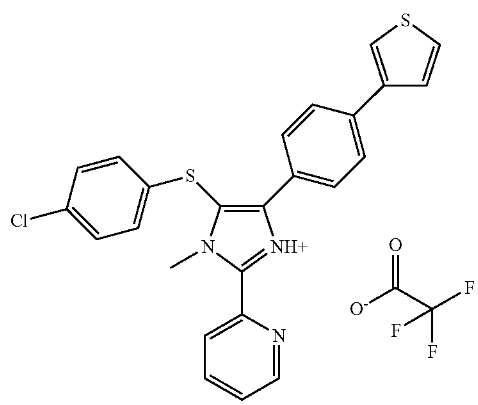 [SMILES: Cn1c(-c2ccccn2)[nH+]c(-c2ccc(-c3ccsc3)cc2)c1Sc1ccc(Cl)cc1 ; O=C([O-])C(F)(F)F] | 1.25 | 460.0 | 8.7 |
| 118 | 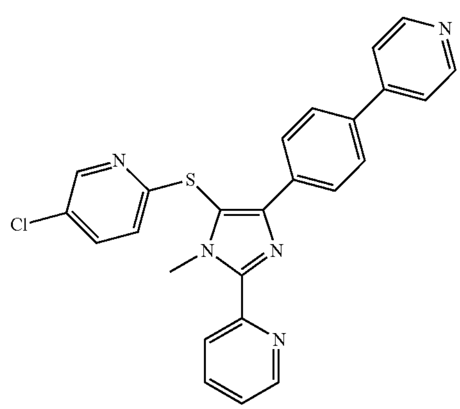 [SMILES: Cn1c(-c2ccccn2)nc(-c2ccc(-c3ccncc3)cc2)c1Sc1ccc(Cl)cn1] | 1.07 | 456.1 | 7.7 |

Example 119

2-{5-[(4-chlorophenyl)thio]-1-methyl-4-[4-(1,3-thia-zol-2-yl)phenyl]-1H-imidazol-2-yl}pyridine

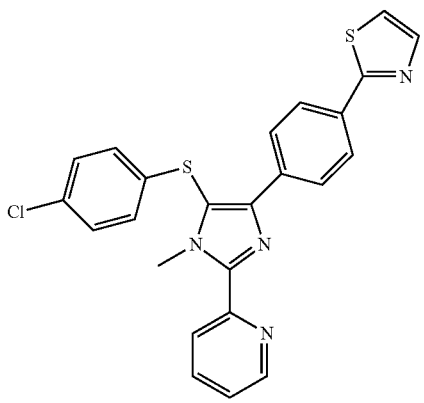 [SMILES: Cn1c(-c2ccccn2)nc(-c2ccc(-c3nccs3)cc2)c1Sc1ccc(Cl)cc1]

A mixture of 2-{4-(4-bromophenyl)-5-[(4-chlorophenyl)thio]-1-methyl-1H-imidazol-2-yl}pyridine (Example 15, 200 mg, 0.438 mmol), 2-(tributylstannyl)-1,3-thiazole (0.138 mL, 0.438 mmol), and tetrakis (50 mg, 0.044 mmol) was dissolved in toluene and heated at 150° C. for 20 min via microwave irradiation. The solvent was evaporated and the residue purified via column chromatography to afford the title compound. $^1$H NMR (500 MHz, $(CD_3)_2CO$): δ 8.71 (d, 1H), 8.40 (d, 1H), 8.40 (d, 2H), 8.32 (d, 2H), 8.00 (m, 1H), 7.90 (d, 1H), 7.63 (d, 1H), 7.46 (m, 1H), 7.36 (d, 2H), 7.20 (d, 2H), 4.18 (s, 3H). LCMS: m/z 461.0 (M+H)+. Human FAAH lysate assay: $IC_{50}$=14.3 nM.

The examples in Table 8 were prepared according to the procedure described for Example 119 using the appropriate stannane and either 2-{4-(4-bromophenyl)-5-[(4-chlorophenyl)thio]-1-methyl-1H-imidazol-2-yl}pyridine (Example 15) or the analagously prepared 2-{[4-(4-bromophenyl)-1-methyl-2-pyridin-2-yl-1H-imidazol-5-yl]thio}-5-chloropyridine as starting materials.

TABLE 8

| Example | Compound structure | LCMS rt (min) | M + 1 | hFAAH lysate $IC_{50}$ (nM) |
|---|---|---|---|---|
| 120 | 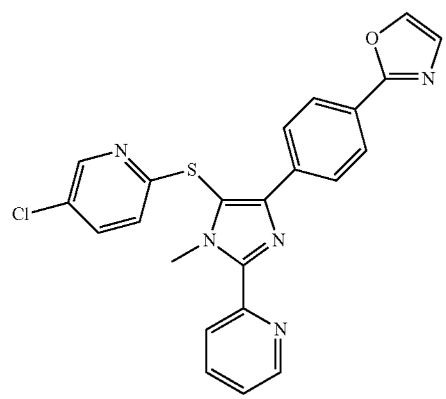 [SMILES: Cn1c(-c2ccccn2)nc(-c2ccc(-c3ncco3)cc2)c1Sc1ccc(Cl)cn1] | 1.17 | 446.0 | 26.4 |
| 121 | 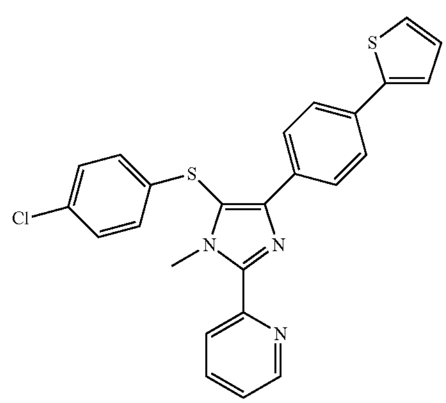 [SMILES: Cn1c(-c2ccccn2)nc(-c2ccc(-c3cccs3)cc2)c1Sc1ccc(Cl)cc1] | 1.20 | 460.2 | 18.5 |

TABLE 8-continued

| Example | Compound structure | LCMS rt (min) | M + 1 | hFAAH lysate IC$_{50}$ (nM) |
|---|---|---|---|---|
| 122 | 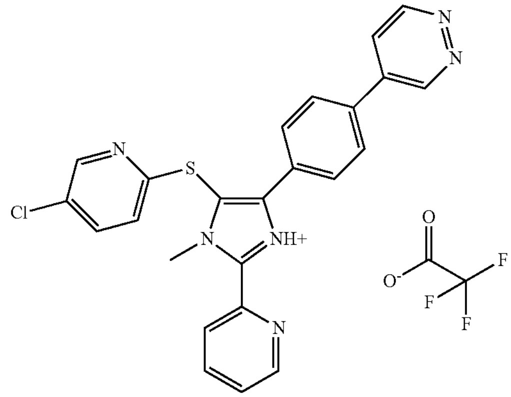 [SMILES: Cn1c(-c2ccccn2)[nH+]c(-c2ccc(-c3ccnnc3)cc2)c1Sc1ccc(Cl)cn1 ; O=C([O-])C(F)(F)F] | 1.12 | 457.1 | 15.7 |

Example 123

Ethyl 4-{5-[(5-chloropyridin-2-yl)thio]-1-methyl-1H-imidazol-4-yl}benzoate

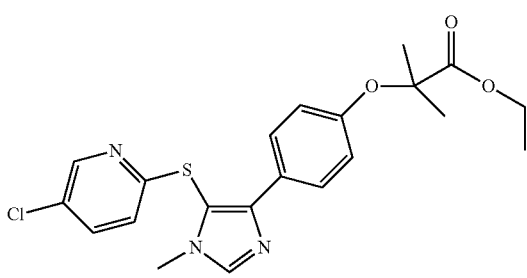 [SMILES: CCOC(=O)C(C)(C)Oc1ccc(-c2ncn(C)c2Sc2ccc(Cl)cn2)cc1]

Step 1. A solution of 2-bromo-1-(4-hydroxyphenyl)ethanone (20 g, 93 mmol) in formamide (75 mL) was heated at 140° C. for 16 h. To the cooled mixture was added imidazole (20 g, 294 mmol), TBS-Cl (31 g, 206 mmol), and DMF (40 mL). The resulting suspension was stirred at rt for 16 h. Water was added and the mixture was extracted with ethyl acetate. The organics were dried (MgSO$_4$) and concentrated. The residue was subject to silica column chromatography (eluting a mixture of DCM:TEA:MeOH 40:2:1) to give 4-(4-{[tert-butyl(dimethyl)silyl]oxy}phenyl)-1H-imidazole (15 g, 59%). LCMS: m/z 275.2 (M+H)+.

Steps 2-3. The product from the previous step was reacted under the conditions described in Intermediate 7 (Steps 2-3) to provide 4-(4-{[tert-butyl(dimethyl)silyl]oxy}phenyl)-5-iodo-1-methyl-1H-imidazole. LCMS: m/z 415.2 (M+H)+.

Step 4. The product from the previous step was reacted under the conditions described in Example 36 to provide 2-[4-(4-{[tert-butyl(dimethyl)silyl]oxy}phenyl)-1-methyl-1H-imidazol-5-yl]-5-chloropyridine. LCMS: m/z 432.3 (M+H)+.

Step 5. The product from the previous step (750 mg, 1.736 mmol) was dissolved in THF (6 mL), TBAF (1M in THF, 2.08 mL). After stirring at rt for 2 h, the reaction was quenched with aqueous NH$_4$Cl and diluted with EtOAc. The organic layer was washed with water and brine. The volatiles were evaporated and the residue was purified by reverse phase HPLC to afford 4-{5-[(5-chloropyridin-2-yl)thio]-1-methyl-1H-imidazol-4-yl}phenol. 1H NMR (500 MHz, (CD$_3$)$_2$CO): δ 8.43 (s, 1H), 7.97 (s, 1H), 7.88 (d, 2H), 7.71 (d, 1H), 6.91 (d, 1H), 6.82 (d 2H) 3.72 (s 3H). LCMS: m/z 318.1 (M+H)+.

Step 6. Ethyl 2-bromoisobutyrate (3 mL, 20.14 mmol) was added to a solution of the product from the previous step (3.2 g, 10.07 mmol) and cesium carbonate (10 g, 30.7 mmol) in acetonitrile (13 mL). The mixture was stirred at 50° C. over the weekend, Water was added and the mixture was extracted with ethyl acetate. The organics were dried (MgSO$_4$) and concentrated to afford the title compound as a pale orange oil which was used in the subsequent steps with out further purification. LCMS: in/z 374.1 (M+H)+.

Example 124

2-(4-{5-[(5-chloropyridin-2-yl)thio]-1-methyl-1H-imidazol-4-yl}phenoxy)-2-methylpropanamide

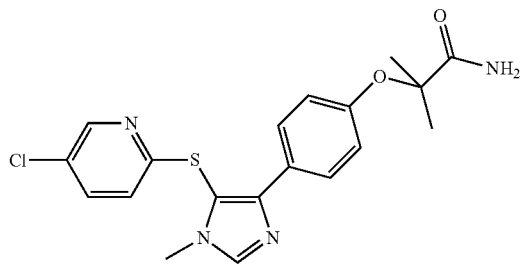 [SMILES: Cn1cnc(-c2ccc(OC(C)(C)C(N)=O)cc2)c1Sc1ccc(Cl)cn1]

Step 1. To a solution of Example 123 (0.2 g, 0.495 mmol) in ethanol (2 mL) and water (1 mL) was added excess potassium hydroxide. The resulting mixture was heated to reflux for 1 h, cooled, neutralized with aqueous ammonium chloride and extracted several times with ethyl acetate affording 2-(4-{5-[(5-chloropyridin-2-yl)thio]-1-methyl-1H-imidazol-4-yl}phenoxy)-2-methylpropanoic acid which was used in the next Step with out further purification.

Step 2. To a solution of the product from the previous step (105 mg, 0.259 mmol), 1-hydroxylbenzotriazole hydrate (99 mg, 0.648 mmol), N-[3-(dimethylamino)propyl]-N'-ethylcarbodiimide hydrochloride (124 mg, 0.648 mmol), in dioxane (1 mL) was added ammonia (0.5M in dioxane) (1 mL, 0.5 mmol) and Hunig's base (0.272 Ml, 1.555 mmol). The resulting mixture was heated to 80° C. for 3 h and the mixture was subjected to reverse phase HPLC. The fractions containing the product were collected and concentrated. The residue was diluted with ethyl acetate, washed with aqueous sodium bicarbonate, water, and brine. The organic layer was dried (MgSO$_4$), filtered, and concentrated to afford the title compound. 1H NMR (500 MHz, (CD$_3$)$_2$CO): δ 8.42 (s, 1H), 7.91-7.98 (br, 5H), 6.93 (d, 2H) 3.70 (s, 3H), 1.48 (s, 6H). (LCMS: m/z 403.3 (M+H)+. Human FAAH lysate assay: IC$_{50}$=36.0 nM.

Example 125

5-[(5-chloropyridin-2-yl)thio]-4-[4-(2-hydroxy-1,1-dimethylethoxy)phenyl]-1-methyl-1H-imidazol-3-ium trifluoroacetate

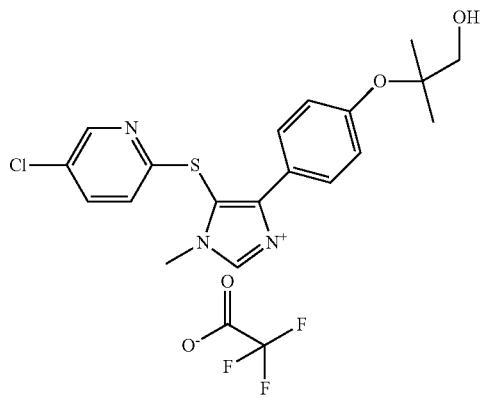

To a solution of Example 123 (50 mg, 129 mmol) in methanol (1 mL) at 0° C. was added excess NaBH$_4$. The reaction was allowed to warm to room temperature over the weekend. the mixture was subjected to reverse phase HPLC. The fractions containing the product were collected and concentrated to afford the title compound. 1H NMR (500 MHz, (CD$_3$)$_2$CO): δ 8.42 (s, 1H), 7.91-7.98 (br, 5H), 6.93 (d, 2H) 3.84 (s, 3H), 3.56 (s, 2H), 1.30 (s, 6H). LCMS: m/z 403.3 (M+H)+. Human FAAH lysate assay: IC$_{50}$=197.9 nM.

Example 126

3-(4-{5-[(5-chloropyridin-2-yl)thio]-1-methyl-1H-imidazol-4-yl}phenoxy)-1,1,1-trifluoro-3-methylbutan-2-ol

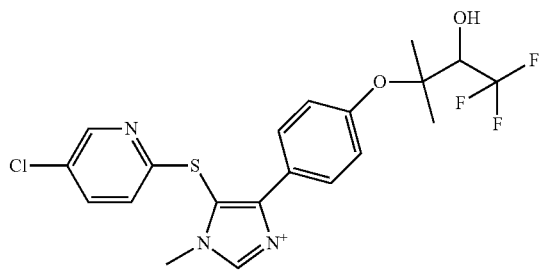

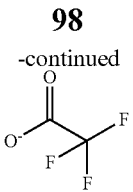

Step 1. To a dry solution of Example 123 (1 g, 2.174 mmol) under an atmosphere of nitrogen was added DIBAL-H (1.5 M in toluene) at −78° C. The reaction was stirred at −78° C. for 30 min. The solution was diluted with an aqueous solution of Rochelle's salt and extracted with EtOAc. The organic layer was removed, dried, filtered and concentrated giving rise to 2-(4-{5-[(5-chloropyridin-2-yl)thio]-1-methyl-1H-imidazol-4-yl}phenoxy)-2-methylpropanal which was used immediately in the next step. LCMS: m/z 388.3 (M+H)+.

Step 2. A solution of the product from the previous step (294 mg, 0.786 mmol), Arduenga's carbene (264 mg, 0.786), and (trifluoromethyl)trimethylsilane (0.377 mL, 2.357 mmol) in DMF (10 mL) was stirred at rt for 16 h. The solution was diluted with 2N HCl and extracted with EtOAc. The organic layer was removed, dried, filtered and concentrated giving rise to an oil. The oil was dissolved in THF and treated with 2 mL of TBAF (1M in THF). The solution was concentrated and purified by reverse phase HPLC. The fractions containing the product were collected and concentrated to afford the title compound. 1H NMR (500 MHz, (CD$_3$)$_2$CO): δ 8.44 (s, 1H), 8.17 (s, 1H), 7.94 (d, 2H), 7.75 (d, 1H), 7.09-7.06 (br, 3H), 4.20 (m, 1H), 3.76 (s, 3H), 1.43 (s, 3H), 1.39 (s, 3H). LCMS: m/z 458.1 (M+H)+. Human FAAH lysate assay: IC$_{50}$=185.5 nM.

Example 127

4-{5-[(4-chlorophenyl)thio]-1-methyl-2-pyridin-2-yl-1H-imidazol-4-yl}-N-(2-hydroxy-1-methylethyl)benzamide

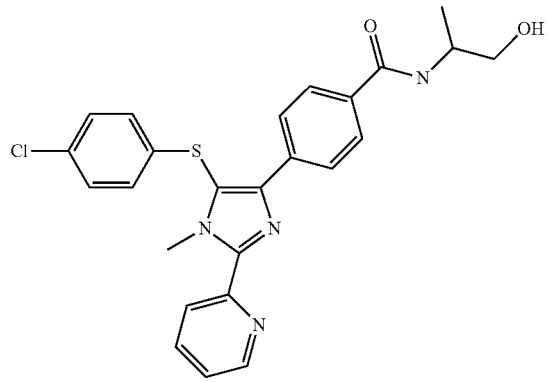 [SMILES: CC(CO)NC(=O)c1ccc(-c2nc(-c3ccccn3)n(C)c2Sc2ccc(Cl)cc2)cc1]

Step 1. A solution of methyl 4-(5-iodo-1-methyl-2-pyridin-2-yl-1H-imidazol-4-yl)benzoate (Intermediate 7, Step 3, 1.5 g, 3.58 mmol) and lithium hydroxide (0.257 g, 10.73 mmol) in acetonitrile (6 mL) and water (6 mL) was heated to 50° C. for 2 h. The mixture was concentrated and extracted with EtOAc. The organics were dried (MgSO$_4$) and concentrated to afford 4-(5-iodo-1-methyl-2-pyridin-2-yl-1H-imidazol-4-yl)benzoic acid. LCMS: m/z 406.0 (M+H)+.

Step 2. To a dry solution of the product from the previous step (500 mg, 1.234 mmol), and PyOP (963 mg, 1.851 mmol) in DMF (5 mL) was added DL-2-amino-1-propanol (0.145 mL, 1.851 mmol), and N-methylmorpholine (0.407 mL, 3.70 mmol). The reaction was stirred at rt for 4 h under an atmosphere of nitrogen. Water was added and the mixture was extracted with EtOAc. The organics were dried (MgSO₄) and concentrated to afford N-(2-hydroxy-1-methylethyl)-4-(5-iodo-1-methyl-2-pyridin-2-yl-1H-imidazol-4-yl)benzamide. LCMS: m/z 462.1 (M+H)+.

Step 3. The title compound was prepared from the product of the previous step by following the same procedure as described in Step 3 for Example 1. 1H NMR (500 MHz, CD₃OD): δ 8.69 (d, 1H), 8.18 (d, 1H), 8.08 (d, 2H), 7.99 (m, 1H), 7.87 (d, 2H), 7.46 (m, 1H), 7.30 (d, 2H), 7.08 (d, 2H), 4.20 (m, 1H), 3.64-3.56 (br, 2H), 1.25 (d, 3H). LCMS: 479.1 (M+H)+. Human FAAH lysate assay: IC$_{50}$=77.9 nM.

Example 128

3-[(4-chlorophenyl)thio]-2-[4-(methylsulfonyl)phenyl]-5,6,6a,7,8,9,10,10a-octahydroimidazo[1,2-h]-1,7-naphthyridine

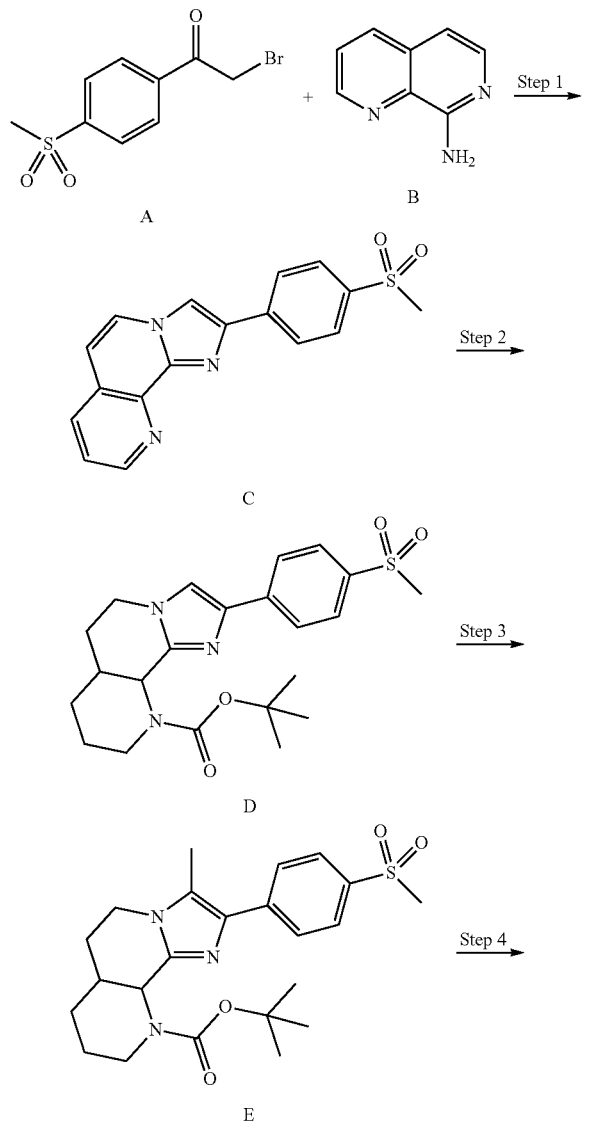

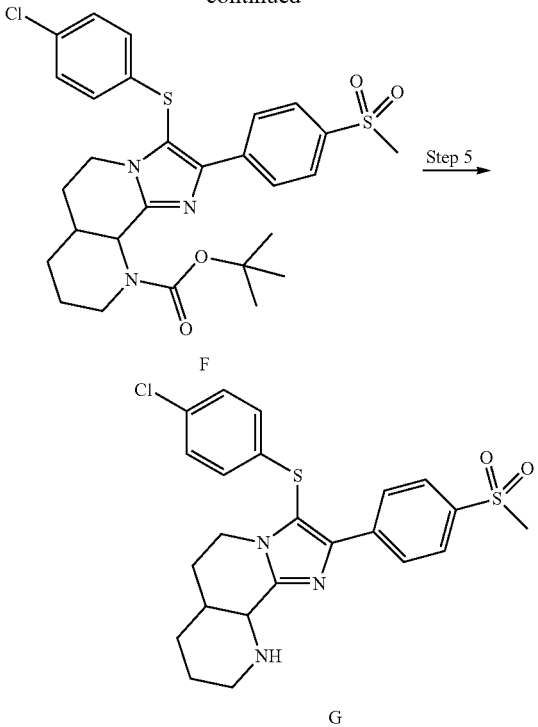

Step 1: Mixed the naphthyridineamine B (781 mg, 5.38 mmol) and NaHCO₃ (904 mg, 10.76 mmol) in THF (10 ml) and water (3.0 ml) and heated to reflux. The bromide A (1.94 g, 7.0 mmol) would not dissolve in THF (10 ml) so it was added over a few min. from a pipette as a suspension. Refluxed for 4 hrs then cooled to rt and stirred over the weekend. Diluted with EtOAc and water, filtered the reddish-brown solids and washed with EtOAc and water.

Dissolved the solids in CH₂Cl₂ with a small amount of MeOH, dried over MgSO₄, filtered, evaporated and dried under high vac at rt. The reddish-brown foam was purified by flash chromatography (SiO₂, 2¼"×3"; 10% IPA-CH₂Cl₂) Pink solids. wt=1.382 g (79%). LC-MS: [M+H]⁺=324.

Step 2: Dissolved the sulfone C (200 mg, 0.618 mmol) in acetic acid (20 ml) in a Parr bottle, added PtO₂ (40 mg, 0.176 mmol) and reduced with H₂ at 45 psi overnight. Filtered and added fresh catalyst to the filtrate; heated to 50 deg. C. and continued reduction with H₂ at atmospheric press. Heated for 2 hrs then cooled to rt and continued reduction overnight. Filtered, added fresh catalyst (40 mg) for a third time and placed in a Parr bottle. Reduced with H₂ at 42 psi over the weekend. Filtered through filtercel to remove catalyst and evaporated filtrate to dryness. Added sat'd. NaHCO₃ and extracted with CH₂Cl₂ (3×), washed extracts with brine, dried over MgSO₄, decolorized with charcoal, filtered and evaporated. Dried the foam under high vac at rt. Purified by prep TLC (SiO₂, 20×20 cm, 1000 microns, 2 plates; 10% IPA-CH₂Cl₂). wt=88 mg (43%). LC-MS: two peaks both with same MS (cis-trans isomers) [M+H]=332.

Dissolved the amine (88 mg, 0.266 mmol) and TEA (0.044 ml, 0.309 mmol) in CH₂Cl₂ (5 ml) and added BOC anhydride (70 mg, 0.309 mmol). Stirred overnight at rt. LC-MS showed a lot of amine SM. so a large excess of both TEA and BOC anhydride was added; stirred over the weekend. Evaporated solvent and replaced with EtOAc. Washed with water and brine, dried over MgSO₄, filtered, evaporated and dried under high vac at rt. Amber oil. wt=133 mg. LC-MS: two major peaks with same MS [M+H]⁺=432.

Step 3: Dissolved sulfone D (132 mg, 0.263 mmol) in CH₂Cl₂ (5.0 ml) and added NIS (76 mg, 0.338 mmol) followed by TFA (1 drop). Stirred the solution at rt overnight. (LC-MS indicated that the reaction was complete after ~2 hrs). Diluted with CH₂Cl₂, washed with sat'd. NaHCO₃ (1×), 10% Na₂S₂O₃ (2×) and brine (1×). Dried over MgSO₄, filtered, evaporated and dried under high vac at rt. Amber oil. wt=138 mg (94%). LC-MS: two major peaks (~2:1) with same MS [M+H]⁺=558. Used without further purification.

Step 4: Suspended the iodide E (137 mg, 0.246 mmol), neocuproine (13 mg, 0.62 mmol), CuI (12 mg, 0.063 mmol), p-chlorothiophenol (53.3 mg, 0.369 mmol) and K₂CO₃ (102 mg, 0.737 mmol) in a sealed vial with CPME (3.0 ml). Degassed by bubbling in N₂ gas briefly then blanketed the vessel with N₂, sealed with a threaded Teflon stopper and heated with stirring at 100 deg. C. Heated overnight. Cooled to rt after 17 hrs. Diluted with CH₂Cl₂ and added water to dissolve K₂CO₃ and salts. Separated layers and extracted aqueous with CH₂Cl₂ (2×). Washed combined extracts with brine (1×), dried over MgSO₄, filtered, evaporated and dried under high vac. rt. Purified by prep TLC (SiO₂, 20×20 cm, 1000 microns, 2 plates; hexane-EtOAc-MeOH, 12:8:2) Isolated two bands.
wt less polar band=21 mg (15%). wt more polar band=28 mg (20%). LC-MS: same for each band with [M+H]⁺=574.

Step 5: 3-[(4-chlorophenyl)sulfanyl]-2-[4-(methylsulfonyl)phenyl]-5,6,6a,7,8,9,10,10a-octahydroimidazo[1,2-h][1,7]naphthyridine (G; the title compound). Dissolved the BOC protected amine (more polar isomer) F (25.1 mg, 0.044 mmol) in CH₂Cl₂ (1 ml) and added 4M HCl in dioxane (2.0 ml). Stirred at rt. Solids pptd. Evaporated to dryness and added a small amount of CH₂Cl₂ to the residue. Diluted with toluene and evaporated (2×). Dried the pink solids under high vac. at rt. wt=23 mg (96%). LC-MS: [M+H]+=474. 1H NMR (500 MHz, CD₃OD) aromatic (d8.37, 7.96, 7.3 and 7.06, all d, 2H ea), aliphatic H (d4.3-0.95, various d,m, 12H), S—CH₃ (d3.1, s, 3H). Human FAAH lysate assay: IC₅₀=98.02 nM.

The example 129 in Table 9 was prepared following the same procedures as in Steps 1, 3 and 4 in Example 129 using the appropriate starting material.

Example 130

2-(4-{3-[(4-chlorophenyl)sulfanyl]imidazo[1,2-h][1,7]naphthyridin-2-yl}phenyl)propan-2-ol

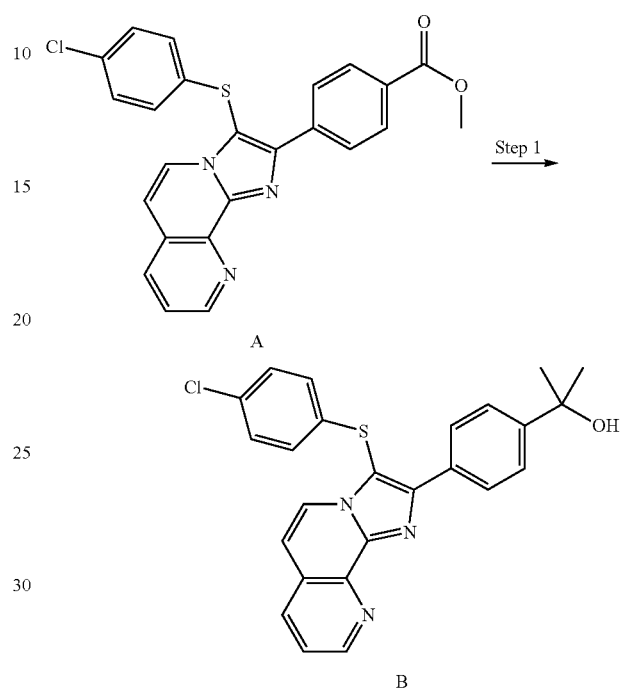

A

B

Dissolved the ester A (75 mg, 0.168 mmol) in THF (5 ml) and added 3M CH₃MgCl in THF (0.280 ml, 0.841 mmol). Stirred at rt overnight. Quenched with sat'd. NH₄Cl, added some water and EtOAc and separated layers; washed organic layer with brine (1×), dried over MgSO₄, filtered, evaporated and dried under high vac at rt. Foam. Purified by prep TLC (SiO₂, 20×20 cm, 1000 microns, 2 plates; hexane-EtOAc-MeOH, 12:8:2) Yellow glass. wt=36 mg (48%). LC-MS: [M+H]+=446. 1H NMR (500 MHz, CDCl₃) aromatics

TABLE 9

| Example | Compound Structure | LCMS rt (min) | M + 1 | hFAAH lysate IC₅₀ (nM) |
|---|---|---|---|---|
| 129 | 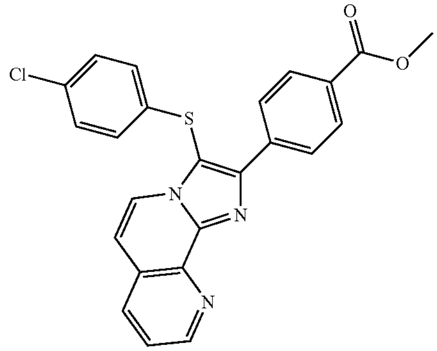 [SMILES: COC(=O)c1ccc(-c2nc3c4ncccc4ccn3c2Sc2ccc(Cl)cc2)cc1] | 3.48 | 446 | 12.15 |

(d9.13-7.0, 8 d, 1 m, 13H total), OH (d3.52, s, ~1H), CH₃'s (d1.61, s, 6H). Human FAAH lysate assay: IC$_{50}$=47.13 nM.

Example 131

6-{5-[(5-chloropyridin-2-sulfanyl]-2-cyclopropyl-1-methyl-1H-imidazol-4-yl}-2-difluoromethyl)quinoline

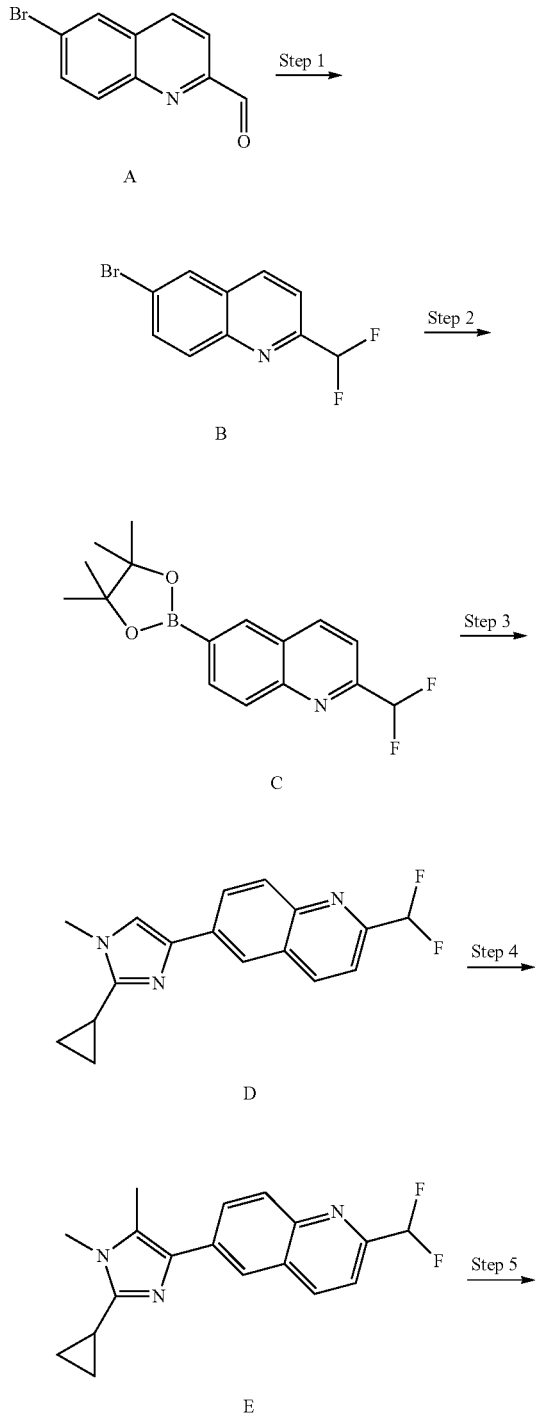

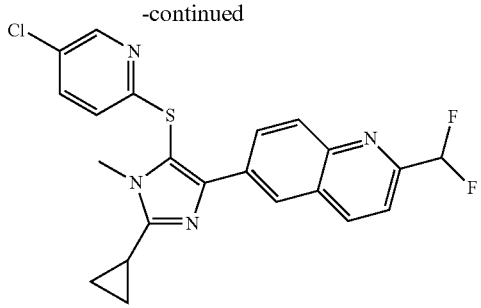

Step 1: Suspended the aldehyde A (472 mg, 2 mmol) in CH$_2$Cl$_2$ (2 ml) and added a solution of Deoxo-Fluor (0.627 ml, 3.4 mmol) in CH$_2$Cl$_2$ (2 ml) followed by EtOH (0.023 ml, 0.4 mmol). Most solids dissolved. Stirred over the weekend at rt. Diluted with CH$_2$Cl$_2$ and added sat'd. NaHCO$_3$. Extracted with CH$_2$Cl$_2$ (3×), washed extracts with brine (1×), dried over MgSO$_4$, filtered, evaporated and dried under high vac at rt. Light brownish orange solids. wt=507 mg (98%) LC-MS: [M+H]+=258, 260 for 1 Br. Used without further purification.

Step 2: Mixed the bromide B (504 mg, 1.953 mmol), BISPIN (506 mg, 1.992 mmol), PdCl$_2$(dppf) (43 mg, 0.059 mmol) and KOAc (575 mg, 5.86 mmol) with DMSO (4.0 ml) in a sealed vial. Degassed by bubbling in N$_2$ gas and then blanketing vessel with N$_2$ and sealed with a Teflon stopper. Heated to 80-90 deg. C. Heated and stirred overnight. Cooled to rt after 16 hrs. Diluted with water and extracted with EtOAc (3×), washed with brine (1×), dried over MgSO$_4$, decolorized with charcoal, filtered, evaporated and dried under high vac at rt. Viscous amber oil which solidified on drying. wt=429 mg. LC-MS: [M+H]+=306. Used without further purification.

Step 3: Dissolved commercially available 2-cyclopropyl-4-iodo-1-methyl-1H-imidazole (241 mg, 0.973 mmol), the boronic acid C (429 mg, 1.167 mmol) and PdCl$_2$(dppf) (21.4 mg, 0.029 mmol) in DMF (3.2 ml) and added Na$_2$CO$_3$ (516 mg, 4.87 mmol) and water (0.72 ml) in a sealed tube and degassed by bubbling in N$_2$ gas, placed under N$_2$ and sealed with a threaded Teflon stopper. Heated to 90 deg C. for 6 hrs. then cooled to rt and stirred over the weekend. Diluted with water and extracted with CH$_2$Cl$_2$ (3×), washed extracts with brine (1×), dried over MgSO$_4$, decolorized with charcoal, filtered, evaporated filtrate to dryness and dried under high vac at rt. The viscous dark brown oil was purified by prep TLC (SiO$_2$, 20×20 cm, 1000 microns, 3 plates; hexane-EtOAc, 1:1). Off-white solids. wt=102 mg (35%). LC-MS: [M+H]+=300.

Step 4: Dissolved the imidazole D (100 mg, 0.334 mmol) in CH$_2$Cl$_2$ (2 ml) and added NIS (83 mg, 0.368 mmol) and 1 drop of TFA. The clear amber solution was stirred at rt for 2 hrs. Diluted with CH$_2$Cl$_2$ and washed with sat'd. NaHCO$_3$, dilute Na$_2$S$_2$O$_3$ and brine (1× ea); dried over MgSO$_4$, filtered, evaporated and dried under high vac at rt. Off-white solids. wt=114 mg (80%). LC-MS: [M+H]+=426.

Step 5: Mixed the iodide E (57 mg, 0.134 mmol) and 3-chloro-6-pyridinethiol (21.5 mg, 0.147 mmol) in IPA (5 ml) in a sealed tube and added CuI (2.8 mg, 0.015 mmol), K$_2$CO$_3$ (37 mg, 0.268 mmol) and ethylene glycol (0.015 ml, 0.268 mmol). Degassed by bubbling in N$_2$ gas for several min., blanketed under N$_2$ and sealed the flask with a Teflon stopper. Heated to 80 deg. C. Stirred and heated the suspension overnight. Cooled to rt and evaporated to dryness. Added water to the residue and extracted with CH$_2$Cl$_2$ (3×); washed extracts with brine (1×), dried over MgSO$_4$, filtered and evaporated to dryness. Purified by prep TLC (SiO$_2$, 20×20 cm, 1000 micron, 1 plate; hexane-EtOAc, 3:1) Developed in chamber 3× allowing separation of product from SM. Colorless glass. wt=31 mg (52%) LC-MS: [M+H]+=443. 1H NMR (500 MHz, CDCl3) aromatics (d8.5, s, d, 2H; d8.42, s, 1H; d8.3, 8.1, 7.7, 7.5 and 6.81, all d, 1H ea), CHF$_2$ (d 6.79, t with large coupling constant, 1H), CH$_3$ (d3.73, s, 3H), CH cyclopropyl (d1.98, m, 1H), CH$_2$—CH$_2$ cyclopropyl (d1.25 and 1.13, both m, 2H ea). Human FAAH lysate assay: IC$_{50}$=17.9 nM.

Example 132

6-{5-[(5-chloropyridin-2-yl)thio]-2-cyclopropyl-1-methyl-1H-imidazol-4-yl}-N,N-dimethylquinoline-2-carboxamide The Example 132 in Table 10 was prepared following the same procedures as in Example 131 replacing Step 1 as follows.

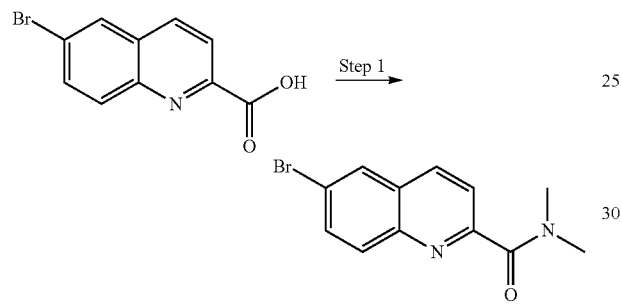

Step 1: Suspended the 6-bromoquinoline-2-carboxylic acid (1.0 g, 3.93 mmol) in CH$_2$Cl$_2$ (20 ml), added DMF (0.912 ml, 11.78 mmol) and cooled in an ice bath. Added oxalyl chloride (0.688 ml, 7.86 mmol) dropwise over a few min. Warmed to rt and stirred for 1 hr then bubbled in dimethylamine gas for several min. Stirred the dark amber mixture at rt overnight. Diluted with water and extracted with CH$_2$Cl$_2$ (3×). Washed extracts with brine (1×), dried over MgSO$_4$, decolorized with charcoal, filtered, evaporated and dried under high vac, rt. Amber oil which solidified on drying. wt=990 mg (90%). LC-MS: [M+H]+=279, 281.

Example 133

5-[(4-chlorophenyl)thio]-2-iodo-1-methyl-4-[4-(methylsulfonyl)phenyl]-1H-imidazole

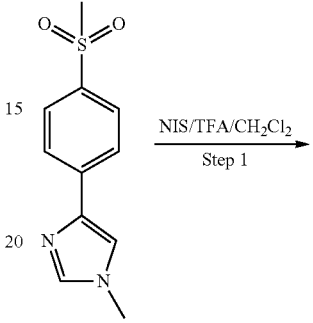

TABLE 10

| Example | Compound Structure | LCMS rt (min) | M + 1 | hFAAH lysate IC$_{50}$ (nM) |
|---------|-------------------|---------------|-------|------------------------------|
| 132 | 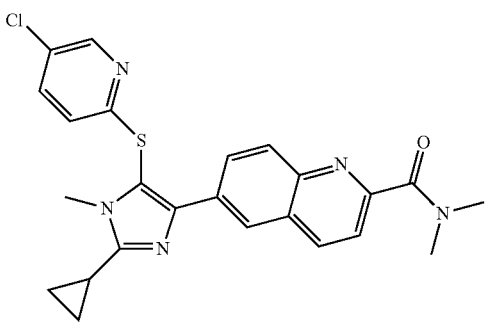 [SMILES: CN(C)C(=O)c1ccc2cc(-c3nc(C4CC4)n(C)c3Sc3ccc(Cl)cn3)ccc2n1] | 1.02 | 464 | 144 |

-continued

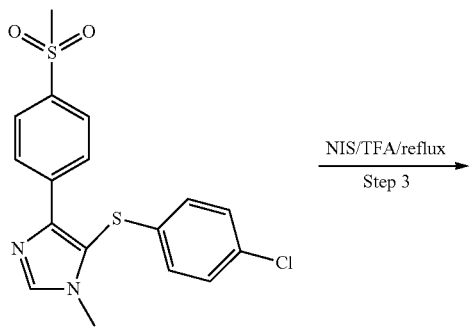

NIS/TFA/reflux
Step 3

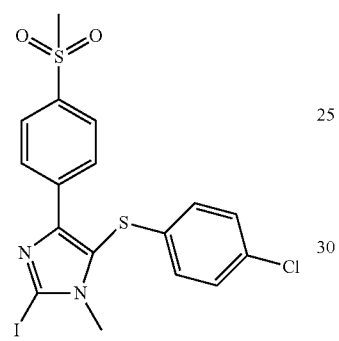

Step 1: To the solution of 1-methyl-4-[4-(methylsulfonyl) phenyl]-1H-imidazole (2.3 g, 9.73 mmol) in CH₂Cl₂ (6 ml) was added TFA (3.0 ml, 38.9 mmol), and NIS (2.41 g, 10.71) at rt. After being stirred at rt for 3 h, the reaction mixture was diluted with CH₂Cl₂, quenched with NaHCO₃ (aq), washed with aq Na₂S₂O₃, water and brine. Dried over Na₂SO₄, filtered and concentrated to afford 5-iodo-1-methyl-4-[4-(methylsulfonyl)phenyl]-1H-imidazole (3.4 g) which was used in the next step without further purification. LCMS: [M+1]⁺=363.0

Step 2: To a dry suspension of the Step 1 product (1.0 g, 2.76 mmol), potassium carbonate (1.15 g, 8.28 mmol), copper (I) iodide (53 mg, 0.276 mmol), and 4-chlorobenzenethiol (0.439 g, 3.04 mmol) in isopropanol (10 ml) under an atmosphere of nitrogen was added ethylene glycol (0.46 ml, 8.28 mmol). The reaction mixture was stirred at 80° C. for 16 h. Water was added and the mixture was extracted with ethyl acetate. The organics were dried (MgSO₄), concentrated, and purified on silica gel column eluting a gradient of 6-50% acetone in CH₂Cl₂ to give 5-[(4-chloropbenyl)sulfanyl]-1-methyl-4-[4-(methylsulfonyl)phenyl]-1H-imidazole (860 mg). LCMS: [M+1]⁺=379.1

Step 3: To the solution of Step 2 product (200 mg, 0.528 mmol) in CH₂Cl₂ (0.5 ml) was added TFA (3 ml) and NIS (238 mg, 1.06 mmol) at rt, and then reaction mixture was heated to reflux overnight. Reaction mixture was cooled to rt and concentrated. To the residue was added CH₂Cl₂, quenched with NaHCO₃ (aq), washed with aq Na₂S₂O₃, water and brine. Dried over Na₂SO₄, filtered and concentrated. Separated by prep TLC (hex:EtOAc=1:1) to give 5-[(4-chlorophenyl)sulfanyl]-2-iodo-1-methyl-4-[4-(methylsulfonyl)phenyl]-1H-imidazole as light yellow solid (180 mg). LCMS: [M+1]⁺=505.0 Human FAAH lysate assay: IC₅₀=15.6 nM.

Example 134

4-{5-[(4-chlorophenyl)sulfanyl]-1-methyl-4-[4-(methylsulfonyl)phenyl]-1H-imidazol-2-yl}-1-methyl-1H-pyrazole

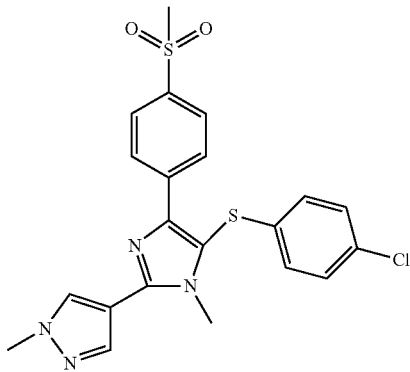 [SMILES: Cn1cc(-c2nc(-c3ccc(S(C)(=O)=O)cc3)c(Sc3ccc(Cl)cc3)n2C)cn1]

A mixture of Example 133 compound (60 mg, 0.119 mmol), methylpyrazole boronic acid (29.7 mg, 0.143 mmol), Pd(PPh₃)₄ (13.7 mg, 0.012 mmol), K₃PO₄ (50.5 mg, 0.238 mmol, aq) in dioxane (2 ml) was vacuumed and purged to N₂ for 3 times, then reaction mixture was heated at 110° C. for 3 hrs. Reaction mixture was diluted with EtOAc, washed with brine dried and concentrated. Separated by prep TLC (hex:EtOAc:CH₃OH=6:5:1) to give 4-{5-[(4-chlorophenyl)sulfanyl]-1-methyl-4-[4-(methylsulfonyl)phenyl]-1H-imidazol-2-yl}-1-methyl-1H-pyrazole (25 mg) 1H NMR (500 MHz), [(CDCl₃]: 8.35 (m, 1H), 7.95 (m, 3H), 7.25 (m, 3H), 7.01 (m, 2H), 4.10 (s, 3H), 3.78 (s, 3H), 3.10 (s, 3H). LCMS: [M+1]⁺=459.0. Human FAAH lysate assay: IC₅₀=13.9 nM.

The Examples in Table 11 were prepared following the procedures described in Example 134 using the appropriate Boronic acid.

TABLE 11

| Example | Compound structure | LCMS rt (min) | M + 1 | hFAAH lysate IC$_{50}$ (nM) |
|---|---|---|---|---|
| 135 | 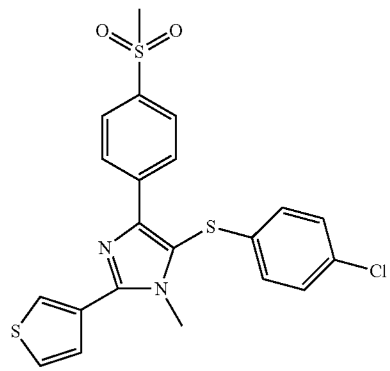 [SMILES: Cn1c(-c2ccsc2)nc(-c2ccc(S(C)(=O)=O)cc2)c1Sc1ccc(Cl)cc1] | 3.13 | 461.0 | 25.9 |
| 136 | 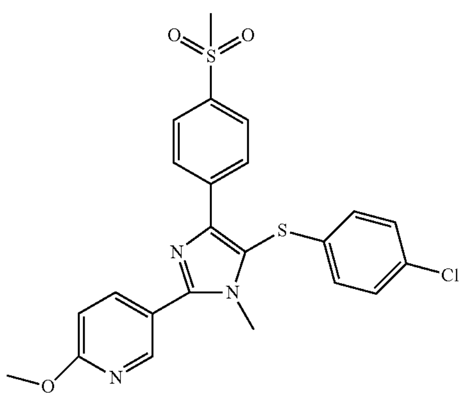 [SMILES: COc1ccc(-c2nc(-c3ccc(S(C)(=O)=O)cc3)c(Sc3ccc(Cl)cc3)n2C)cn1] | 3.19 | 486.1 | 122.3 |

Example 137

5-[(4-chlorophenyl)sulfanyl]-1-methyl-4-[4-(methyl-sulfonyl)phenyl]-2-(thiophen-2-yl)-1H-imidazole

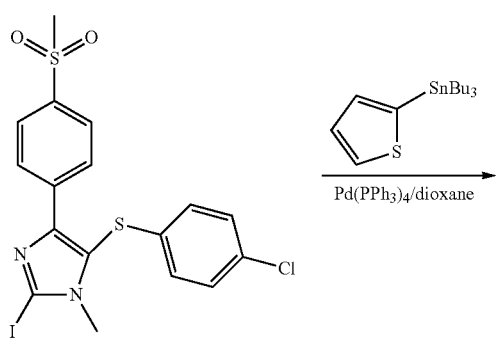

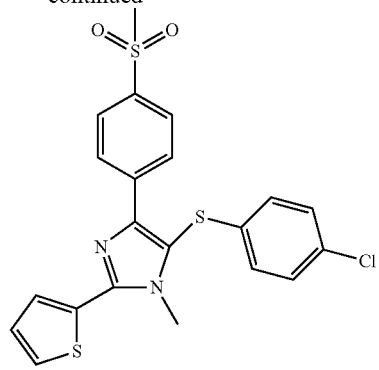

A mixture of Example 133 compound (34 mg, 0.067 mmol), thiophene tin reagent (22.34 μl, 0.0704 mmol) and Pd(PPh$_3$)$_4$ (77.42 mg, 0.067 mmol) in dioxane (1 ml) was vacuumed and purged to N$_2$ for 3 times, then reaction mixture was heated at 110° C. for 4 hrs. The reaction mixture was cooled to rt, added KF (sat, 1 ml), stirred at rt for one hour, filtered, washed with EtOAc, and separated to two layers. The organic layer was washed with brine, dried, filtered, concentrated, and separated by prep TLC (CH$_2$Cl$_2$:Hex:EtOAc=3:3:1) to afford 5-[(4-chlorophenyl)sulfanyl]-1-methyl-4-[4-

(methylsulfonyl)phenyl]-2-(thiophen-2-yl)-1H-imidazole (25 mg). 1H NMR (500 MHz), [CDCl₃]: 8.38 (m, 2H), 7.95 (m, 2H), 7.50 (m, 2H), 7.40 (m, 2H), 7.15 (m, 1H), 7.10 (m, 2H), 3.82 (s, 3H), 3.05 (s, 3H). LCMS: [M+1]⁺=461.0. Human FAAH lysate assay: IC₅₀=16.5 nM.

The Examples in Table 12 were prepared following the procedures described in Example 137 using the appropriate tin reagents.

TABLE 12

| Example | Compound structure | LCMS rt (min) | M + 1 | hFAAH lysate IC₅₀ (nM) |
|---|---|---|---|---|
| 138 | 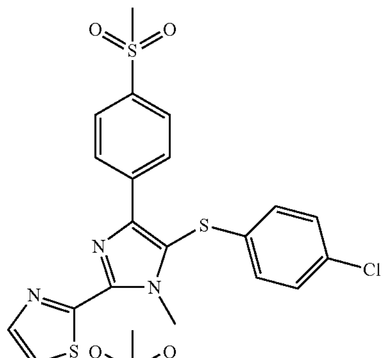 | 1.23 | 462.0 | 24.75 |
| 139 | 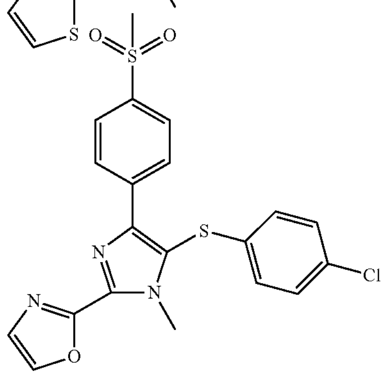 | 1.18 | 446.1 | 21.2 |

Example 140

3-4-({5-[(4-chlorophenyl)sulfanyl]-2-(1-ethyl-1H-pyrazol-3-yl)-1-methyl-1H-imidazol-4-yl)phenyl)-1,2,4-oxadiazole

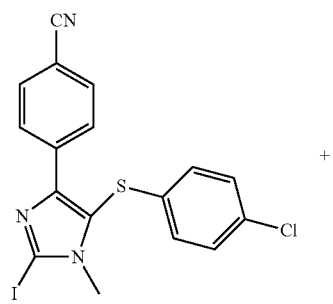

+

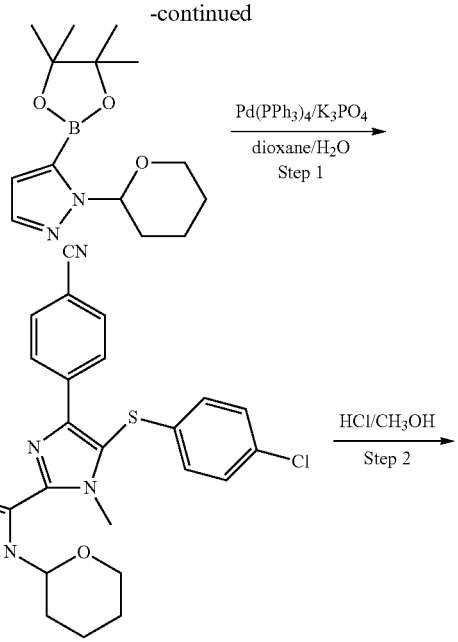

-continued

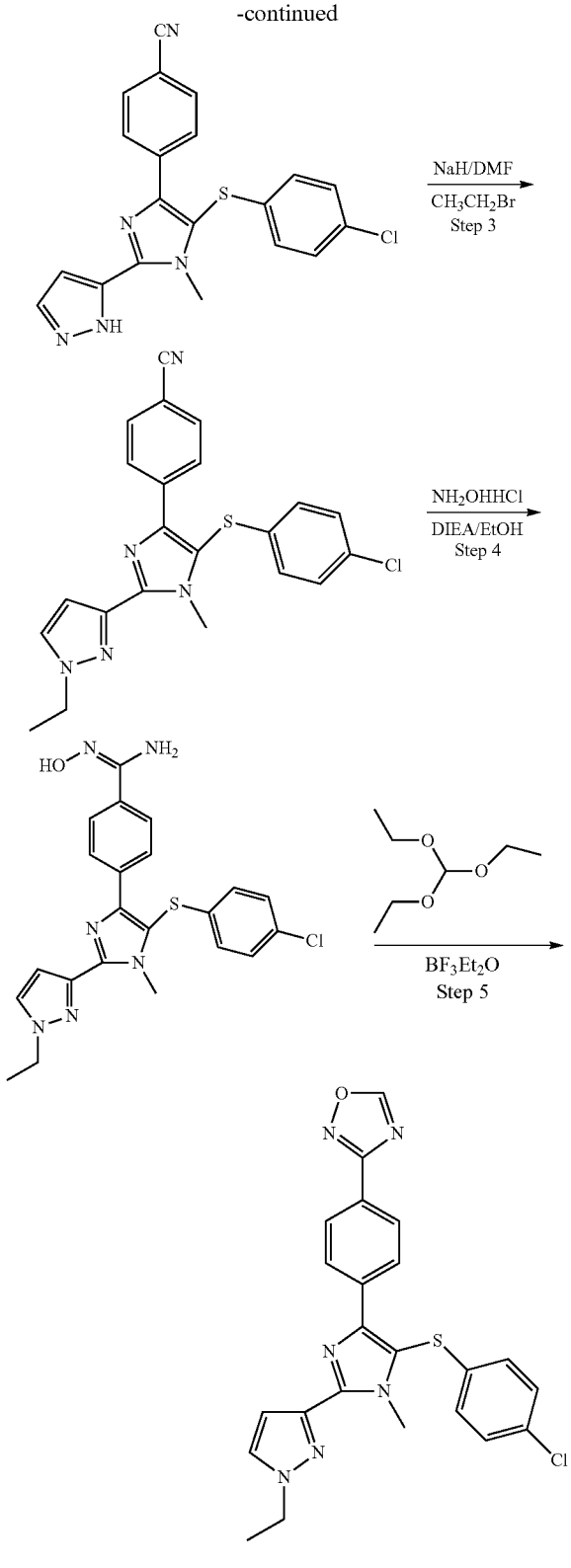

Step 1: The same procedure in Example 134 was used in this step and the starting material iodoimidazole was prepared following the similar procedure of Step 1 in Example 133. LCMS: [M+1]$^+$=476.1.

Step 2: To a solution of step 1 product (2.4 g, 5.04 mmol) in $CH_3OH$ (25 ml) was added HCl (37%, 1.66 ml, 20.2 mmol) at rt, then heated at 50° C. for 1 h. The reaction mixture was concentrated. To the residue was added $Et_2O$, filtered and collected to give 4-{5-[(4-chlorophenyl)sulfanyl]-1-methyl-2-(1H-pyrazol-5-yl)-1H-imidazol-4-yl}benzonitrile (2.1 g), which was used for the next reaction without purification. LCMS: [M+1]$^+$=392.1

Step 3: To a solution of the step 2 product (400 mg, 1.02 mmol) in DMF (8 ml) at 0° C. was added NaH (82 mg, 2.04 mmol). After stirred at 0° C. for 0.5 hr, $CH_3CH_2Br$ (0.114 ml, 1.53 mmol) was added and stirred at 0° C. for one hour, and then at rt overnight. The reaction mixture was quenched with water, extracted with EtOAc, washed with brine, dried over $Na_2SO_4$, filtered, concentrated, and separated by HPLC (8-100% EtOAc in hex) to give 4-{5-[(4-chlorophenyl)sulfanyl]-2-(1-ethyl-1H-pyrazol-3-yl)-1-methyl-1H-imidazol-4-yl}benzonitrile (250 mg) as yellow solid. LCMS: [M+1]$^+$=420.1

Step 4: To a suspension of step 3 product C-5 (240 mg, 0.572 mmol) in EtOH (5 ml) was added hydroxylamine (199 mg, 2.86 mmol) and DMA (0.498 ml, 2.86 mmol). After stirred at rt for 10 min, the reaction mixture was heated at 80° C. for 2 hrs. and then concentrated. To the residue was added EtOAc and washed with $Na_2CO_3$ (aq), organic layer was dried, and concentrated to give 4-{5-[(4-chlorophenyl)sulfanyl]-2-(1-ethyl-1H-pyrazol-3-yl)-1-methyl-1H-imidazol-4-yl}-N'-hydroxybenzenecarboximidamide (230 mg), which was used for further reaction without purification. LCMS: [M+1]$^+$=453.2.

Step 5: To a suspension of step 4 product (250 mg, 0.552 mmol) in triethyl orthoformate (9.09 ml, 55.2 mmol) was added $BF_3$ etherate (0.699 μl, 5.52 μmol) and the mixture stirred at 110° C. for overnight. The reaction mixture was diluted with EtOAc and washed with $NaHCO_3$ (aq), organic layer was dried, and concentrated. The residue was purified on silica gel column eluting a gradient of 8-70% EtOAc in hexane to afford 3-(4-{5-[(4-chlorophenyl)sulfanyl]-2-(1-ethyl-1H-pyrazol-3-yl)-1-methyl-1H-imidazol-4-yl}phenyl)-1,2,4-oxadiazole (130 mg; more polar; the major regioisomer. There was also a minor regioisomer that was the subject of the next example). 1H NMR (500 MHz), [$CDCl_3$]: 8.78 (s, 1H), 8.28 (m, 2H), 8.15 (m, 2H), 7.55 (m, 1H), 7.22 (m, 2H), 7.06 (m, 2H), 6.95 (m, 1H), 4.28 (q, 2H), 4.00 (s, 3H), 1.60 (t, 3H). LCMS: [M+1]$^+$=463.1 (rt=1.16 min). Human FAAH lysate assay: $IC_{50}$=28.7 nM.

Example 141

3-(4-{5-[(4-chlorophenyl)sulfanyl]-2-(1-ethyl-1H-pyrazol-5-yl)-1-methyl-1H-imidazol-4-yl}phenyl)-1,2,4-oxadiazole

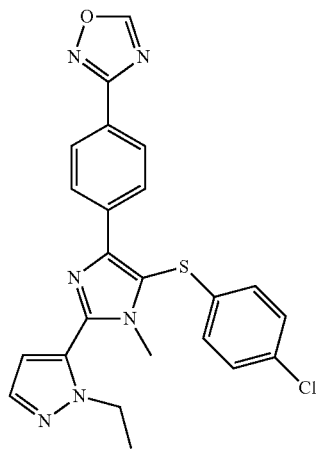 [SMILES: CCn1nccc1-c1nc(-c2ccc(-c3ncon3)cc2)c(Sc2ccc(Cl)cc2)n1C]

From the Step 5 of Example 140, a minor regioisomer was also isolated, which was 3-(4-{5-[(4-chlorophenyl)sulfanyl]-

2-(1-ethyl-1H-pyrazol-5-yl)-1-methyl-1H-imidazol-4-yl}phenyl)-1,2,4-oxadiazole (20 mg; less polar). 1H NMR (500 MHz), [CDCl$_3$]: 8.78 (s, 1H), 8.28 (m, 2H), 8.10 (m, 2H), 7.62 (m, 1H), 7.26 (m, 2H), 7.06 (m, 2H), 6.55 (m, 1H), 4.60 (q, 2H), 3.78 (s, 3H), 1.60 (t, 3H). LCMS: [M+1]$^+$=463.1 (rt=1.23 min). Human FAAH lysate assay: IC$_{50}$=67.9 nM.

Example 142

3-(4-{5-[(4-chlorophenyl)sulfanyl]-1-methyl-2-[1-(propan-2-yl)-1H-pyrazol-3-yl]-1H-imidazol-4-yl}phenyl)-1,2,4-oxadiazole

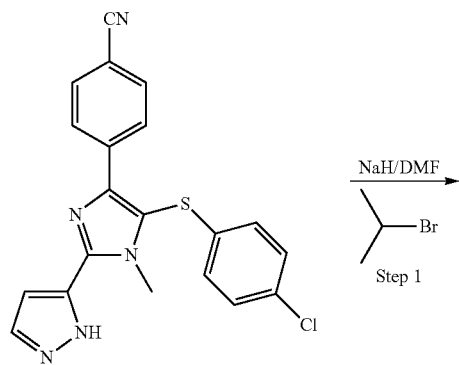

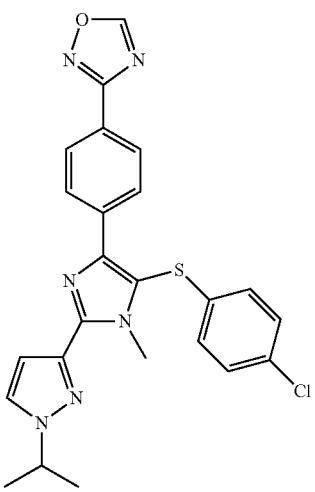

Step 1: This step followed the similar procedure of Step 3 in Example 140 except that bromoethane was replaced with 2-bromopropane. LCMS: [M+1]$^+$=434.1.

Step 2: This step followed the similar procedure of Step 4 in Example 140. LCMS: [M+1]$^+$=467.3.

Step 3: This step followed the similar procedure of Step 5 in Example 140. 1H NMR (500 MHz), [CDCl$_3$]: 8.78 (s, 1H), 8.28 (m, 2H), 8.16 (m, 2H), 7.56 (m, 1H), 7.22 (m, 2H), 7.04 (m, 2H), 6.95 (m, 1H), 4.58 (m, 1H), 4.00 (s, 3H), 1.56 (d, 6H). LCMS: [M+1]$^+$=447.3. Human FAAH lysate assay: IC$_{50}$=15.6 nM.

Example 143

3-(4-{5-[(4-chlorophenyl)sulfanyl]-1-methyl-2-(1-methyl-1H-pyrazol-3-yl)-1H-imidazol-4-yl}phenyl)-1,2,4-oxadiazole

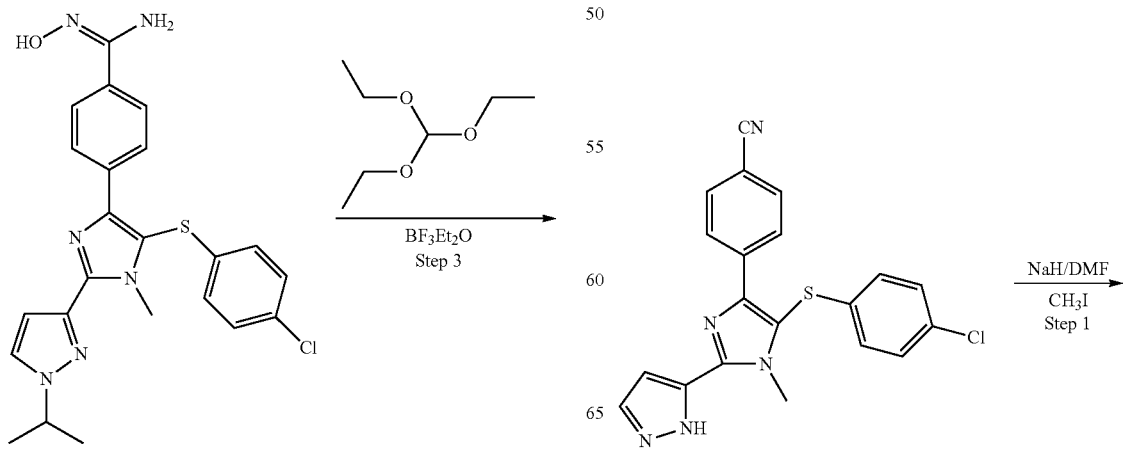

Example 144

3-(4-{5-[(4-chlorophenyl)sulfanyl]-2-(1-cyclopropyl-1H-pyrazol-3-yl)-1-methyl-1H-imidazol-4-yl}phenyl)-1,2,4-oxadiazole

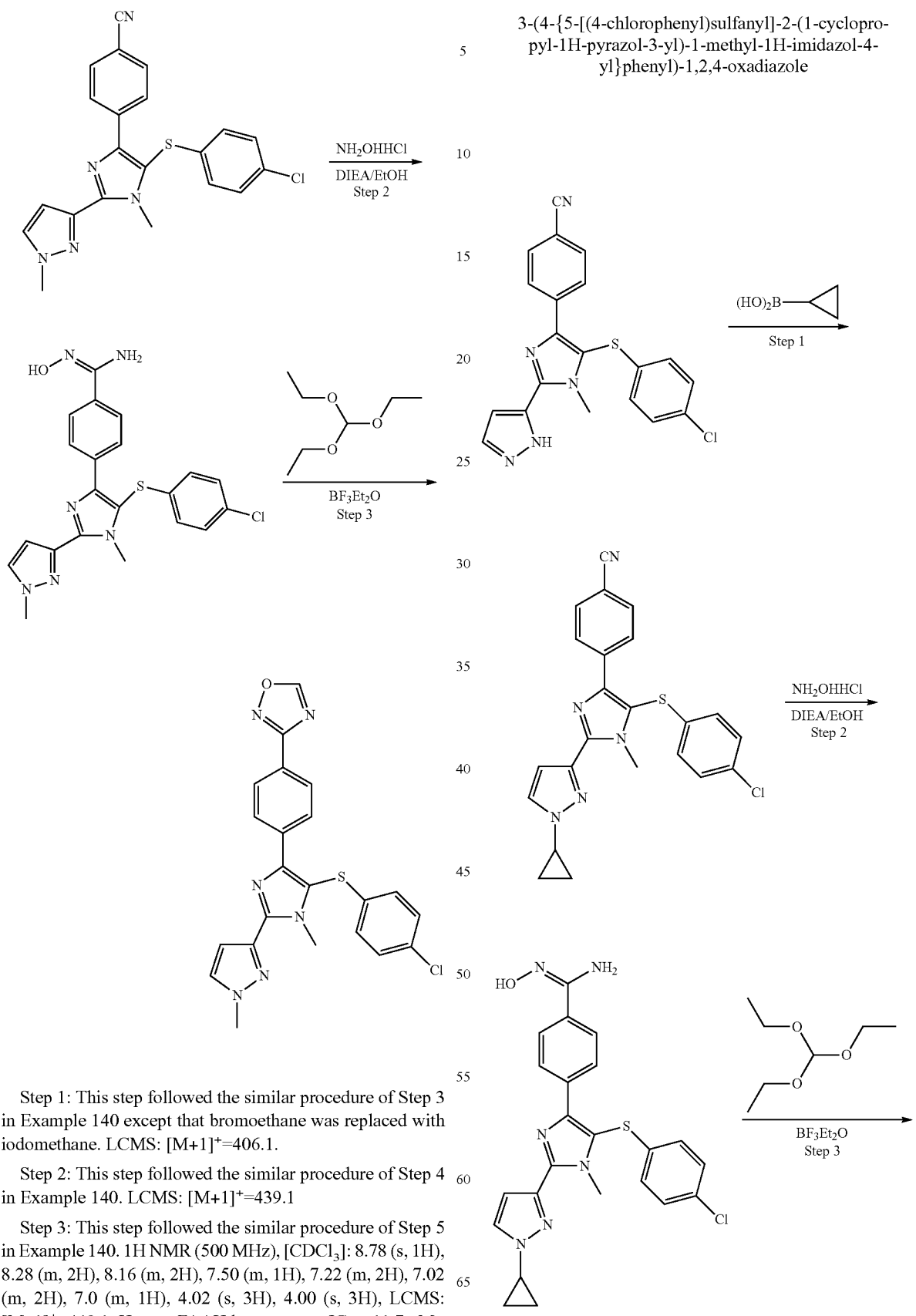

Step 1: This step followed the similar procedure of Step 3 in Example 140 except that bromoethane was replaced with iodomethane. LCMS: [M+1]$^+$=406.1.

Step 2: This step followed the similar procedure of Step 4 in Example 140. LCMS: [M+1]$^+$=439.1

Step 3: This step followed the similar procedure of Step 5 in Example 140. 1H NMR (500 MHz), [CDCl$_3$]: 8.78 (s, 1H), 8.28 (m, 2H), 8.16 (m, 2H), 7.50 (m, 1H), 7.22 (m, 2H), 7.02 (m, 2H), 7.0 (m, 1H), 4.02 (s, 3H), 4.00 (s, 3H), LCMS: [M+1]$^+$=449.1. Human FAAH lysate assay: IC$_{50}$=11.7 nM.

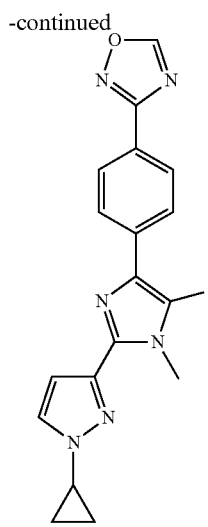

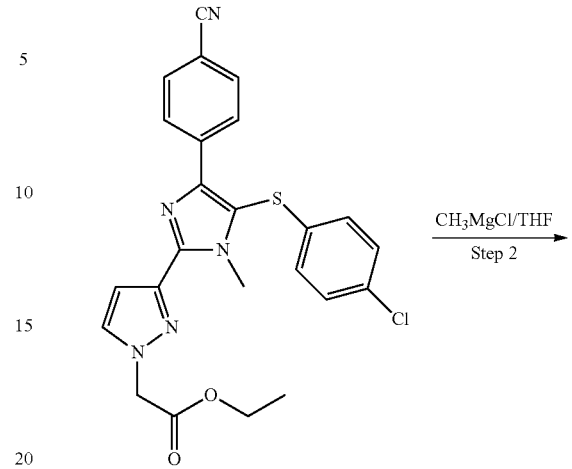

Step 1: To a mixture of Step 2 product of Example 140 (150 mg, 0.383 mmol), cyclopropyl boronic acid (132 mg, 1.53 mmol) and Cu(II) acetate (139 mg, 0.766 mmol) in dioxane (2.0 ml) were added DMAP (187 mg, 1.53 mmol), $Cs_2CO_3$ (125 mg, 0.383 mmol) and 1,10-phenanthroline (276 mg, 1.53 mmol) in a sealed tube under $N_2$, stirred at rt for 30 min and then heated at 90° C. for overnight. Reaction mixture was diluted water, extracted with EtOAc, washed with brine and dried over $Na_2SO_4$, filtered, concentrated, and separated by prep TLC (hex:EtOAc=2:1) to afford 4-{5-[(4-chlorophenyl)sulfanyl]-2-(1-cyclopropyl-1H-pyrazol-3-yl)-1-methyl-1H-imidazol-4-yl}benzonitrile (60 mg) as white solid. LCMS: $[M+1]^+=432.0$.

Step 2: This step followed the similar procedure of Step 4 in Example 140. LCMS: $[M+1]^+=465.0$.

Step 3: This step followed the similar procedure of Step 5 in Example 140. 1H NMR (500 MHz), [$CDCl_3$]: 8.78 (s, 1H), 8.28 (m, 2H), 8.16 (m, 2H), 7.58 (m, 1H), 7.22 (m, 2H), 7.04 (m, 2H), 6.96 (m, 1H), 4.00 (s, 3H), 3.70 (m, 1H), 1.12 (m, 2H), 1.05 (m, 2H). LCMS: $[M+1]^+=475.0$. Human FAAH lysate assay: $IC_{50}=7.4$ nM.

Example 145

4-{5-[(4-chlorophenyl)sulfanyl]-2-[1-(2-hydroxy-2-methylpropyl)-1H-pyrazol-3-yl]-1-methyl-1H-imidazol-4-yl}benzonitrile

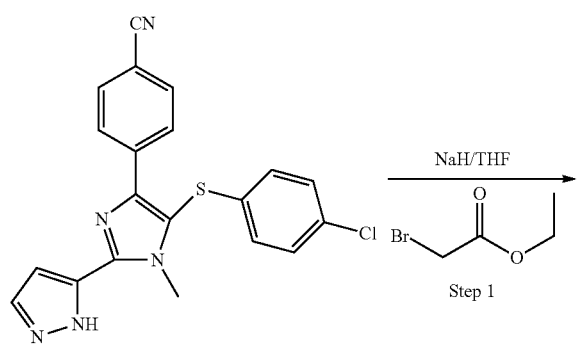

Step 1: To a mixture of Step 2 product of Example 140 (100 mg, 0.255 mmol) in THF (2 ml) at 0° C. was added NaH (20.4 mg, 0.510 mmol). After stirred at 0° C. for 1 hr, ethyl bromo acetate (0.034 ml, 0.306 mmol) was added and then stirred at 0° C. for one hour. Reaction mixture was quenched with water, extracted with EtOAc, washed with brine, dried over $Na_2SO_4$, filtered, concentrated, separated by prep. TLC (Hex: EtOAc=2:1) to give ethyl (3-{5-[(4-chlorophenyl)sulfanyl]-4-(4-cyanophenyl)-1-methyl-1H-imidazol-2-yl}-1H-pyrazol-1-yl)acetate (70 mg) desired compound. LCMS: $[M+1]^+=478.0$.

Step 2: To a solution of the step 1 product (30 mg, 0.063 mmol) in THF (2 ml) at 0° C. was added $CH_3MgCl$ (0.105 ml, 0.314 mmol, 3M in THF). After being stirred at 0° C. for 0.5 hr, the reaction mixture was allowed to warm up to rt and stirred for overnight. The reaction mixture was quenched with $NH_4Cl$, extracted with EtOAc, washed with brine, dried over $Na_2SO_4$, filtered, concentrated, and separated by prep. TLC (Hex:EtOAc=1:1) to afford 4-{5-[(4-chlorophenyl)sulfanyl]-2-[1-(2-hydroxy-2-methylpropyl)-1H-pyrazol-3-yl]-1-methyl-1H-imidazol-4-yl}benzonitrile (7 mg). 1H NMR (500 MHz), [$CDCl_3$]: 8.28 (m, 2H), 7.70 (m, 2H), 7.58 (m, 1H), 7.25 (m, 3H), 7.02 (m, 2H), 4.16 (m, 2H), 3.98 (s, 3H), 1.60 (s, 6H). LCMS: [M+1]⁺=464.2. Human FAAH lysate assay: IC₅₀=23.1 nM.

Example 146

2-{5-[(4-chlorophenyl)sulfanyl]-1-methyl-4-[4-(1,2,4-oxadiazol-3-yl)phenyl]-1H-imidazol-2-yl}propan-2-ol

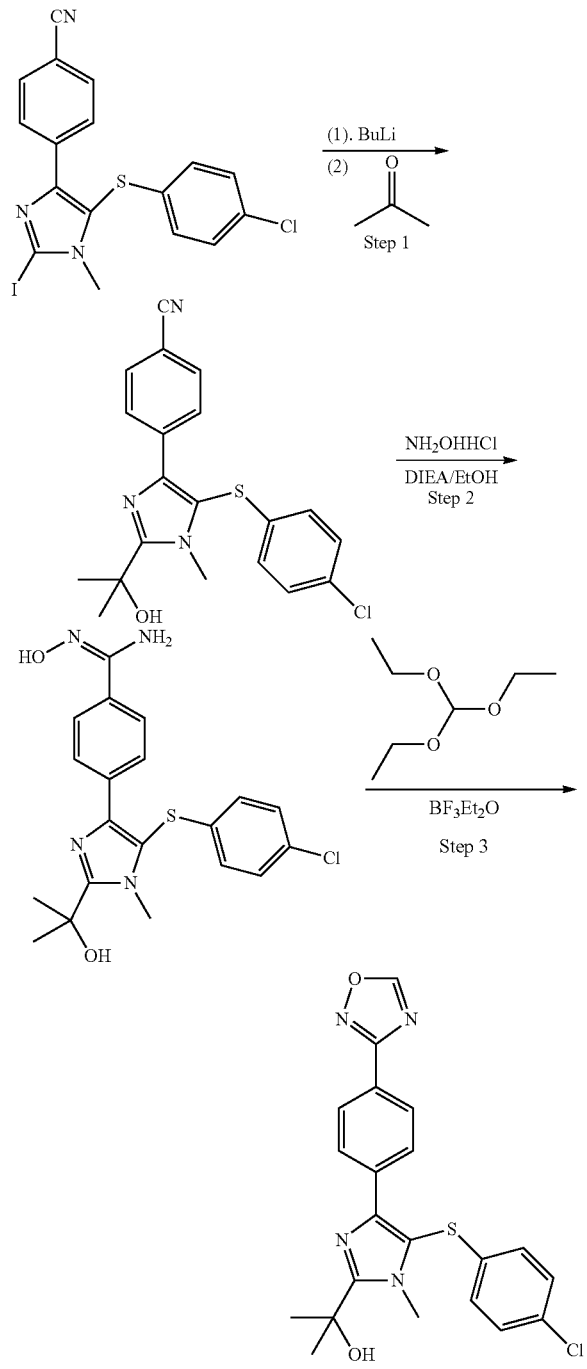

Step 1: To a solution of the iodoimidazole (Example 140 starting material, 100 mg, 0.221 mmol) in THF (2 ml) was added n-BuLi (0.097 ml, 0.244 mmol, 2.5 M) at −78° C. After being stirred at −78° C. for half hour, acetone (0.02 mL, 0.266 mmol) was added and the reaction was stirred for another 2 hrs. The reaction mixture was quenched with NH₄Cl, extracted with EtOAc, washed with brine, dried, concentrated, and purified by prep TLC (hex:EtOAc=2:1) to give 4-{5-[(4-chlorophenyl)sulfanyl]-2-(2-hydroxypropan-2-yl)-1-methyl-1H-imidazol-4-yl}benzonitrile (25 mg) as white solid LCMS: [M+1]⁺=384.3.

Step 2: This step followed the similar procedure of Step 4 in Example 140. LCMS: [M+1]⁺=417.3.

Step 3: To a suspension of Step 2 product (120 mg, 0.288 mmol) in triethyl orthoformate (4.74 ml, 28.8 mmol) was added BF₃ etherate (0.365 μl, 2.88 μmol) and the mixture stirred at 110° C. for overnight. The reaction mixture was diluted with EtOAc and washed with NaHCO₃ (aq), organic layer was dried, and concentrated. The residue was purified by prep TLC (hex:EtOAc=2:1) to give 2-{5-[(4-chlorophenyl)sulfanyl]-1-methyl-4-[4-(1,2,4-oxadiazol-3-yl)phenyl]-1H-imidazol-2-yl}propan-2-ol (7 mg, more polar product. There was a less polar product which is the subject of Example 147). 1H NMR (500 MHz), [CDCl₃]: 8.78 (s, 1H), 8.28 (m, 2H), 8.15 (m, 2H), 7.25 (m, 2H), 7.02 (m, 2H), 3.81 (s, 3H), 1.80 (s, 6H). LCMS: [M+1]⁺=427.0 (rt=1.10). Human FAAH lysate assay: IC₅₀=208.4 nM.

Example 147

3-(4-{5-[(4-chlorophenyl)sulfanyl]-2-(2-ethoxypropan-2-yl)-1-methyl-1H-imidazol-4-yl}phenyl)-1,2,4-oxadiazole

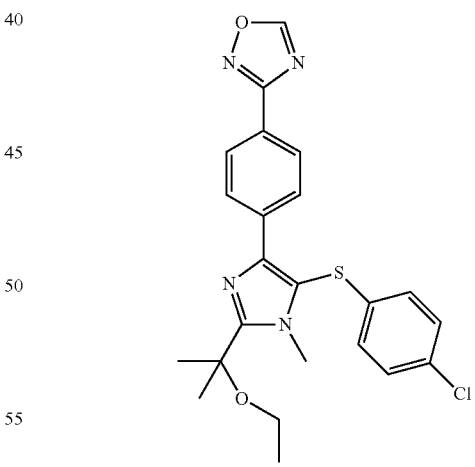

From Step 3 of Example 147, the title compound 3-(4-{5-[(4-chlorophenyl)sulfanyl]-2-(2-ethoxypropan-2-yl)-1-methyl-1H-imidazol-4-yl}phenyl)-1,2,4-oxadiazole was also isolated (52 mg, less polar product). 1H NMR (500 MHz), [CDCl₃]: 8.78 (s, 1H), 8.22 (m, 2H), 8.16 (m, 2H), 7.22 (m, 2H), 6.98 (m, 2H), 3.80 (s, 3H), 3.30 (q, 2H), 1.78 (s, 6H), 1.21 (t, 3H). LCMS: [M+1]⁺=455.2 (rt=1.23). Human FAAH lysate assay: IC₅₀=24.4 nM.

Example 148

2-(5-{5-[(5-chloropyridin-2-yl)sulfanyl]-2-(5-cyclopropylisoxazol-3-yl)-1-methyl-1H-imidazol-4-yl}pyridin-2-yl)propan-2-ol

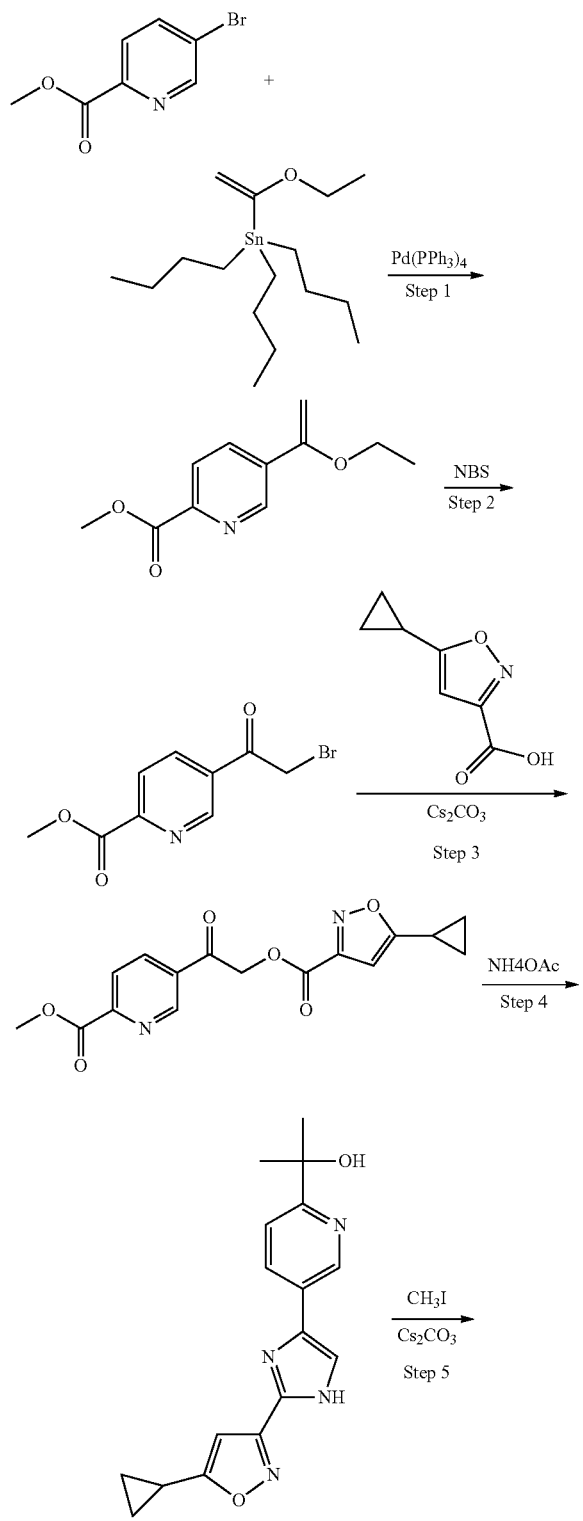

Step 1: To a solution of methyl 5-bromopyridine-2-carboxylate (5.0 g, 23.1 mg) in dioxane (80 ml) was added Pd(PPh$_3$)$_4$ (1.34 g, 1.16 mmol) and tributyl(1-ethoxyethenyl)stannane (8.60 ml, 25.5 mmol). After stirring the reaction mixture at reflux temp for overnight, the mixture was diluted with ethyl acetate, washed with 10% KF solution (aqueous), filtered though celite, dried, concentrated, and separated by HPLC (8-70% EtOH in hexane) to give methyl 5-(1-ethoxyethenyl)pyridine-2-carboxylate (4.8 g). LCMS: [M+H]$^+$=208.2

Step 2: To a solution of step 1 product (780 mg, 3.76 mmol) in THF (37.5 ml) and H$_2$O (2.5 ml) was added NBS (670 mg, 3.76 mmol) in one portion. The solution was stirred at rt for 10 min, solvent was removed and purified on silica gel column eluting a gradient of 8-75% EtOAc in hexane to afford methyl 5-(bromoacetyl)pyridine-2-carboxylate (0.92 g) LCMS: [M+H]$^+$=258.1, 260.1.

Step 3: To a solution of 5-cyclopropylisoxazole-3-carboxylic acid (153 mg, 1.00 mmol) in ethanol (6 ml) was added cesium carbonate (165 mg, 0.506 mmol). After stirring the reaction mixture for 1 hr, it was concentrated. The residue was dissolved in DMF (2 ml), Step 2 product (258 mg, 1.00 mmol) was added and the reaction was stirred for 1 hr. The reaction mixture was diluted with EtOAc, washed with water, the organic layer was dried and concentrated to afford methyl 5-({[(5-cyclopropylisoxazol-3-yl)carbonyl]oxy}acetyl)pyridine-2-carboxylate (380 mg) as an yellow oil, which was used in the next step without purification. LCMS: $[M+H]^+$=331.2.

Step 4: To a solution of the product from Step 3 (330 mg, 1.0 mmol) in xylene (3 ml) was added ammonium acetate (771 mg, 10 mmol) and heated to reflux for 2 hrs. The reaction mixture was cooled to rt, diluted with EtOAc, washed with NaHCO$_3$, the organic layer was dried, concentrated, and separated by prep TLC (hex:EtOAc: CH3OH=6:5:1) to give 2-{5-[2-(5-cyclopropylisoxazol-3-yl)-1H-imidazol-4-yl]pyridin-2-yl}propan-2-ol (60 mg) as yellow solid. LCMS: $[M+H]^+$=311.2.

Step 5: To a solution of product from Step 4 (60 mg, 0.193 mmol) in THF (1 ml) was added cesium carbonate (126 mg, 0.387 mmol). After being stirred for 10 min, CH$_3$I (0.013 ml, 0.213 mmol) was added and the reaction was stirred for 4 hrs. The reaction mixture was diluted with EtOAc, washed with NaHCO$_3$ (sat), dried, concentrated, and separated by prep TLC (hex:EtOAc:CH$_3$OH=6:5:1) to give 2-{5-[2-(5-cyclopropylisoxazol-3-yl)-1-methyl-1H-imidazol-4-yl]pyridin-2-yl}propan-2-ol (45 mg) LCMS: $[M+H]^+$=325.3.

Step 6: This step followed the procedure of Step 1 in Example 133. LCMS: $[M+1]^+$=451.1.

Step 7: This step followed the procedure of Step 2 in Example 133. 1H NMR (500 MHz), [(CD$_3$OD]: 8.95 (s, 1H), 8.41 (m, 1H), 8.25 (m, 1H), 7.70 (m, 2H), 7.20 (m, 1H), 6.70 (m, 1H), 4.00 (s, 3H), 2.22 (m, 1H), 1.52 (s, 6H), 1.18 (m, 2H), 1.02 (m, 2H). LCMS: $[M+1]^+$=468.3. Human FAAH lysate assay: IC$_{50}$=91.0 nM.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

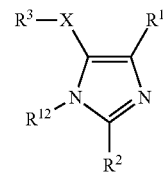

-continued

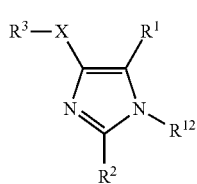
II

X is S or SO;
R$^{12}$ is selected from the group consisting of:
(1) —C$_{1-4}$alkyl,
(2) -haloC$_{1-4}$alkyl,
(3) H;
n is 0, 1 or 2;
R$^1$ is selected from the group consisting of:
(1) aryl, and
(2) HET$^1$,
wherein choice (1) and (2), is optionally mono or di-substituted with substituents R$^4$ and R$^5$, which are independently selected from the group consisting of:
(a) halo,
(b) —CN,
(c) mono, di or tri-halo C$_{1-4}$ alkyl,
(d) —OC$_{1-4}$ alkyl, optionally substituted with hydroxy, halo or amino,
(e) —C$_{1-4}$alkyl optionally substituted with one or two substituents selected from hydroxyl, CN, —CHF$_2$ and —CF$_3$,
(f) —C$_{1-2}$alkyl-C$_{3-6}$cycloalkyl optionally substituted with hydroxy, halo or CN,
(g) —S(O)$_n$C$_{1-4}$alkyl,
(h) —S(O)$_n$NR$^6$R$^7$,
(i) —C(O)—NH—NR$^8$R$^9$,
(j) —C(O)—OH,
(k) —C(O)—OC$_{1-4}$alkyl, optionally substituted with halo or hydroxy,
(l) —C(O)—NR$^{10}$R$^{11}$,
(m) —C(O)—C$_{1-4}$alkyl optionally mono, di or tri substituted with halo,
(o) —C(NR$^{12}$)—NR$^{13}$R$^{14}$,
(p) HET$^4$,
(q) aryl,
(r) —C(O)—NH—NH—C(O)H,
(s) —CH$_2$—C(O)—O—C$_{1-4}$alkyl, whereas the CH$_2$ may be optionally substituted with C$_{1-4}$ alkyl or OH
(t) —CH$_2$—C(O)NR$^{15}$R$^{16}$, whereas the CH$_2$ may be optionally substituted with C$_{1-4}$ alkyl or OH, and
(u) —NR$^{17}$R$^{18}$,
wherein choices (p) and (q) are each optionally mono or di-substituted with substituents selected from
(1) halo,
(2) —CN,
(3) —OH,
(4) —C$_{1-4}$alkyl optionally substituted with hydroxy, halo or cyano,
(5) —CF$_3$,
(6) —OC$_{1-4}$alkyl optionally substituted with hydroxyl or halo,
(7) —C(O)OH, and
(8) —C(O)O—C$_{1-3}$alkyl;
(9) —C(O)—NR$^{19}$R$^{20}$,
(10) —NH$_2$,
(11) Oxo,
(12) =S, wherein R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$ and R$^{20}$, are each independently selected from H and C$_{1-4}$alkyl,
or
R$^6$ and R$^7$ or R$^8$ and R$^9$ or R$^{10}$ and R$^{11}$ or R$^{13}$ and R$^{14}$ or R$^{15}$ and R$^{16}$ or R$^{17}$ and R$^{18}$ or R$^{19}$ and R$^{20}$ are joined together so that together with the atoms to which they are attached there is formed a 5-membered heterocyclic ring of 4 to 7 atoms, said ring containing 1, 2, 3 or 4 heteroatoms selected from N, O and S, said ring being optionally mono or di-substituted with substituents independently selected from halo, hydroxyl, oxo, C$_{1-4}$alkyl, hydroxyC$_{1-4}$alkyl, haloC$_{1-4}$alkyl, —C(O)—C$_{1-4}$alkyl and —S(O)nC$_{1-4}$alkyl;
R$^2$ is selected from the group consisting of:
(1) aryl,
(2) HET$^3$,
(3) —CH$_2$-aryl,
(4) —CH$_2$—HET$^3$,
(5) —C$_{1-6}$alkyl, and
(6) —C$_{3-6}$cycloalkyl,
wherein choice (1), (2), (3), (4), (5) and (6) is optionally mono or di-substituted with substituents independently selected from the group consisting of
(a) halo,
(b) —CN,
(c) —OH,
(d) —C$_{1-4}$alkyl optionally substituted with hydroxy, halo or cyano,
(e) —CF$_3$,
(f) —OC$_{1-4}$alkyl optionally substituted with hydroxyl or halo,
(g) —C(O)O—C$_{1-3}$alkyl;
R$^3$ is selected from the group consisting of:
(1) aryl,
(2) HET$^5$, and
(3) C$_{3-6}$cycloalkyl,
wherein choice (1), (2) and (3) are each optionally mono or di-substituted with substituents independently selected from the group consisting of
(a) hydroxy,
(b) halo,
(c) —C$_{3-6}$cycloalkyl,
(d) —OC3-5cycloalkyl,
(e) —C$_{1-4}$ alkyl,
(f) —OC$_{1-4}$ alkyl,
(g) —C(O)CH$_3$
(h) mono, di or tri-halo C$_{1-4}$ alkyl,
(i) mono, di or tri-halo —OC$_{1-4}$ alkyl, and
(j) —S(O)$_n$—C$_{1-4}$ alkyl.

2. A compound of claim 1
wherein:
R$^1$ is selected from the group consisting of:
(1) phenyl,
(2) pyridinyl,
(3) pyridazinyl,
(4) pyrimidinyl,
(5) pyrazinyl,
(6) thiazolyl,
(7) thienyl,
(8) pyrrolyl, (9) oxazolyl, and
(10) a bicyclic ring selected from the group consisting of:

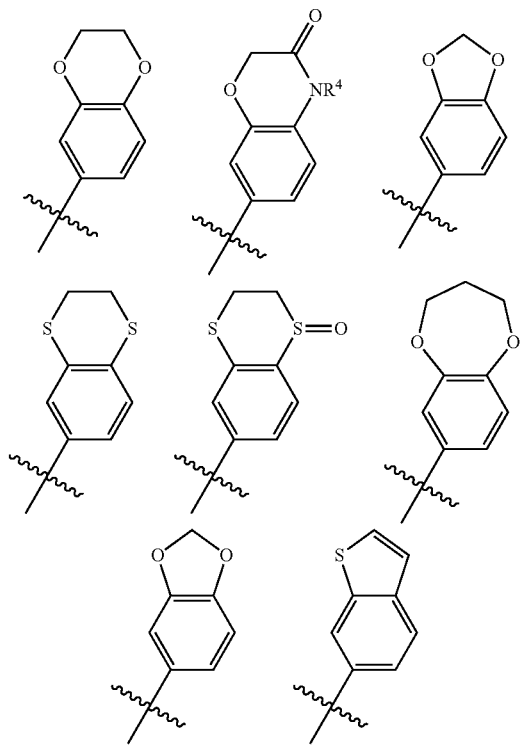

wherein choice of (1) to (9) are each optionally mono or di-substituted with substituents $R^4$ and $R^5$, which are independently selected from the group consisting of
(a) halo,
(b) —CN,
(c) mono, di or tri-halo $C_{1-4}$ alkyl,
(d) —O—$C_{1-4}$alkyl, optionally substituted with hydroxyl, halo or amino
(e) —$C_{1-4}$alkyl optionally substituted with hydroxyl or CN,
(f) —$C_{1-2}$alkyl-$C_{3-6}$cycloalkyl optionally substituted with hydroxy,
(h) —$S(O)_nC_{1-4}$alkyl wherein n is 0, 1 or 2,
(i) —$S(O)_nNR^6R^7$,
(j) —C(O)—$NR^{10}R^{11}$,
(k) $HET^4$,
(l) aryl, and
wherein choices (k) and (l) are each optionally mono or di-substituted with substituents selected from
(1) halo,
(2) —CN,
(3) —OH,
(4) —$C_{1-4}$alkyl optionally substituted with hydroxy, halo or cyano,
(5) —$CF_3$,
(6) —$OC_{1-4}$alkyl optionally substituted with hydroxyl or halo,
(7) —C(O)OH,
(8) —C(O)O—$C_{1-3}$alkyl, and
(9) —C(O)—$NR^{19}R^{20}$,
wherein $R^6$, $R^7$, $R^{10}$, $R^{11}$, $R^{19}$ and $R^{20}$, are each independently selected from H and $C_{1-4}$alkyl, or $R^6$ and $R^7$ or $R^{10}$ and $R^{11}$ or $R^{19}$ and $R^{20}$ are joined together so that together with the atoms to which they are attached there is formed a 5 membered heterocyclic ring of 4 to 7 atoms, said ring containing 1, 2, 3 or 4 heteroatoms selected from N, O and S, said ring being optionally mono or di-substituted with substituents independently selected from halo, hydroxyl, $C_{1-4}$alkyl, —C(O)—$C_{1-4}$alkyl and —$S(O)_nC_{1-4}$alkyl.

3. A compound of claim 2 wherein:
$R^1$ is selected from the group consisting of:
(1) phenyl,
(2) pyridinyl,
(3) pyrimidinyl,
(4) pyrazinyl, and
(5) pyridazinyl,
optionally mono or di-substituted with substituents $R^4$ and $R^5$, which are independently selected from the group consisting of
(a) —$C_{1-4}$alkyl optionally substituted with hydroxy,
(b) —$S(O)_nC_{1-4}$alkyl,
(c) —C(O)—$NR^{10}R^{11}$,
(d) $HET^4$, and
(e) halo,
wherein choice (d) is optionally mono or di-substituted with substituents selected from:
(1) halo,
(2) —CN,
(3) —OH,
(4) —$C_{1-4}$alkyl optionally substituted with hydroxy, halo or cyano,
(5) —$CF_3$,
(6) —$OC_{1-4}$alkyl optionally substituted with hydroxyl or halo,
(7) —C(O)OH, and
(8) —C(O)O—$C_{1-3}$alkyl, and
(9) —C(O)—$NR^{19}R^{20}$,
wherein $R^{10}$, $R^{11}$, $R^{19}$ and $R^{20}$ are each independently selected from H and $C_{1-4}$alkyl, or $R^{10}$ and $R^{11}$ or $R^{19}$ and $R^{20}$ are joined together so that together with the atoms to which they are attached there is formed a 5 membered heterocyclic ring of 4 to 7 atoms, said ring containing 1, 2, 3 or 4 heteroatoms selected from N, O and S, said ring being optionally mono or di-substituted with substituents independently selected from halo, hydroxyl, $C_{1-4}$alkyl, —C(O)—$C_{1-4}$alkyl and —$S(O)nC_{1-4}$alkyl.

4. A compound of claim 1 wherein:
$R^2$ is selected from the group consisting of:
(1) aryl,
(2) $HET^3$,
(3) —$C_{1-6}$alkyl, and
(4) —$C_{1-6}$cycloalkyl,
wherein choice (1), (2), (3), and (4) is optionally mono or di-substituted with substituents independently selected from the group consisting of
(a) halo,
(b) —CN,
(c) —OH,
(d) -Hydroxy $C_{1-4}$alkyl,
(e) —$C_{1-4}$alkyl,
(f) —$C_{1-4}$haloalkyl, and
(g) —$OC_{1-4}$alkyl, optionally substituted with halo or hydroxyl.

5. A compound of claim 4 wherein:
R² is selected from the group consisting of:
(1) aryl, and
(2) HET³,
wherein choice (1) and (2) are each optionally mono or di-substituted with substituents independently selected from the group consisting of
(a) halo,
(b) —CN,
(c) —OH,
(d) -hydroxy $C_{1-4}$ alkyl,
(e) —CH₃,
(f) —CF₃, and
(g) —OCH₃.

6. A compound of claim 5 wherein:
R² is selected from the group consisting of:
(1) phenyl,
(2) pyridinyl,
(3) pyridazinyl,
(4) pyrimidinyl,
(5) pyrizinyl,
(5) thiazolyl,
(6) oxazolyl, and
(7) pyrazolyl,
wherein choice (1), (2), (3), (4), (5), (6) and (7) are each optionally mono or di-substituted with halo, $OC_{1-4}$alkyl optionally substituted with halogen, —$C_{1-4}$-haloalkyl, hydroxyl and CN.

7. A compound of claim 1 wherein
R³ is selected from the group consisting of:
(1) aryl, and
(2) HET⁵,
wherein choice (1) and (2) are each optionally mono or di-substituted with substituents independently selected from the group consisting of:
(a) halo,
(b) —$C_{1-6}$cycloalkyl,
(c) —$C_{1-4}$ alkyl,
(d) —$OC_{1-4}$ alkyl,
(e) mono, di or tri-halo $C_{1-4}$ alkyl, and
(f) mono, di or tri-halo —$OC_{1-4}$ alkyl.

8. A compound of claim 7 wherein
R³ is selected from the group consisting of:
(1) phenyl,
(2) pyrimidinyl,
(3) pyridinyl,
wherein choices (1), (2) and (3) are each optionally mono or di-substituted with halo, halo$C_{1-4}$alkyl, or —$OC_{1-4}$alkyl optionally substituted with halo.

9. A compound of claim 1 wherein X is S and R¹² is methyl.

10. A compound of claim 1 of the Formula

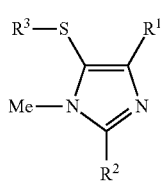

Ia

R¹ is selected from the group consisting of:
(1) phenyl,
(2) pyridinyl,
(3) pyridazinyl,
(4) pyrimidinyl,
(5) pyrazinyl,
(6) thiazolyl,
(7) thienyl,
(8) pyrrolyl,
(9) oxazolyl, and
(10) a bicyclic ring selected from the group consisting of:

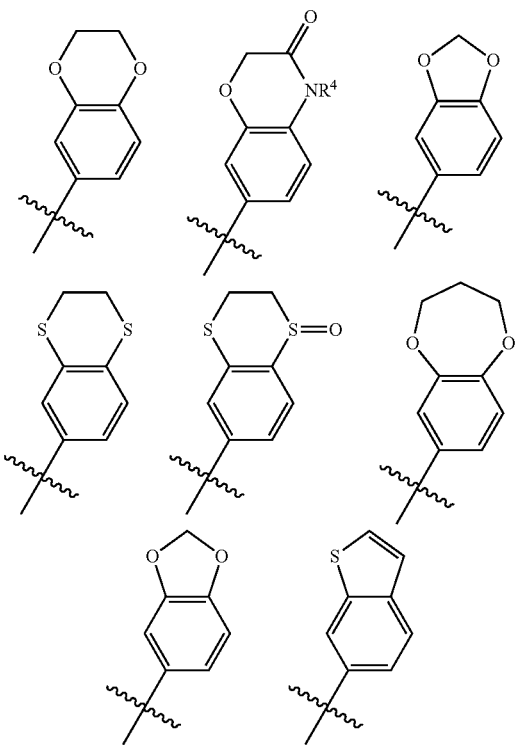

wherein choice of (1) to (9) are each optionally mono or di-substituted with substituents R⁴ and R⁵, which are independently selected from the group consisting of
(a) halo,
(b) —CN,
(c) mono, di or tri-halo $C_{1-4}$ alkyl,
(d) —O—$C_{1-4}$alkyl, optionally substituted with hydroxyl, halo or amino
(e) —$C_{1-4}$alkyl optionally substituted with hydroxyl or CN,
(f) —$C_{1-2}$alkyl-$C_{1-6}$cycloalkyl optionally substituted with hydroxy,
(h) —S(O)$_n C_{1-4}$alkyl wherein n is 0, 1 or 2,
(i) —S(O)$_n$NR⁶R⁷,
(j) —C(O)—NR¹⁰R¹¹,
(k) HET⁴,
(l) aryl, and
wherein choices (k) and (l) are each optionally mono or di-substituted with substituents selected from
(1) halo,
(2) —CN,
(3) —OH,
(4) —$C_{1-4}$alkyl optionally substituted with hydroxy, halo or cyano, (5) —$CF_3$,
(6) —$OC_{1-4}$alkyl optionally substituted with hydroxyl or halo,
(7) —C(O)OH,
(8) —C(O)O—$C_{1-3}$alkyl, and
(9) —C(O)—$NR^{19}R^{20}$,
wherein $R^6$, $R^7$, $R^{10}$, $R^{11}$, $R^{19}$ and $R^{20}$, are each independently selected from H and $C_{1-4}$alkyl, or
$R^6$ and $R^7$ or $R^{10}$ and $R^{11}$ or $R^{19}$ and $R^{20}$ are joined together so that together with the atoms to which they are attached there is formed a 5 membered heterocyclic ring of 4 to 7 atoms, said ring containing 1, 2, 3 or 4 heteroatoms selected from N, O and S, said ring being optionally mono or di-substituted with substituents independently selected from halo, hydroxyl, $C_{1-4}$alkyl, —C(O)—$C_{1-4}$alkyl and —S(O)n$C_{1-4}$alkyl;
$R^2$ is selected from the group consisting of:
  (1) aryl,
  (2) $HET^3$,
  (3) —$C_{1-6}$alkyl, and
  (4) —$C_{1-6}$cycloalkyl,
wherein choice (1), (2), (3), and (4) is optionally mono or di-substituted with substituents independently selected from the group consisting of
  (a) halo,
  (b) —CN,
  (c) —OH,
  (d) -hydroxy $C_{1-4}$alkyl,
  (e) —$C_{1-4}$alkyl,
  (f) —$C_{1-4}$-haloalkyl, and
  (g) —$OC_{1-4}$alkyl, optionally substituted with halo or hydroxyl; and
$R^3$ is selected from the group consisting of:
  (1) aryl, and
  (2) $HET^5$,
  wherein choice (1) and (2) are each optionally mono or di-substituted with substituents independently selected from the group consisting of
    (a) halo,
    (b) —$C_{3-6}$cycloalkyl,
    (c) —$C_{1-4}$ alkyl,
    (d) —$OC_{1-4}$ alkyl,
    (e) mono, di or tri-halo $C_{1-4}$ alkyl, and
    (f) mono, di or tri-halo —$OC_{1-4}$ alkyl.

11. A compound of claim 10 wherein
$R^1$ is selected from the group consisting of:
  (1) phenyl,
  (2) pyridinyl,
  (3) pyrimidinyl,
  (4) pyrazinyl, and
  (5) pyridazinyl,
optionally mono or di-substituted with substituents $R^4$ and $R^5$, which are independently selected from the group consisting of
  (a) —$C_{1-4}$alkyl optionally substituted with hydroxy,
  (b) —$S(O)_nC_{1-4}$alkyl,
  (c) —C(O)—$NR^{10}R^{11}$,
  (d) $HET^4$, and
  (e) halo,
wherein choice (d) is optionally mono or di-substituted with substituents selected from:
  (1) halo,
  (2) —CN,
  (3) —OH,
  (4) —$C_{1-4}$alkyl optionally substituted with hydroxy, halo or cyano,
  (5) —$CF_3$,
  (6) —$OC_{1-4}$alkyl optionally substituted with hydroxyl or halo,
  (7) —C(O)OH, and
  (8) —C(O)O—$C_{1-3}$alkyl, and
  (9) —C(O)—$NR^{19}R^{20}$,
wherein $R^{10}$, $R^{11}$, $R^{19}$ and $R^{20}$ are each independently selected from H and $C_{1-4}$alkyl, or $R^{10}$ and $R^{11}$ or $R^{19}$ and $R^{20}$ are joined together so that together with the atoms to which they are attached there is formed a 5 membered heterocyclic ring of 4 to 7 atoms, said ring containing 1, 2, 3 or 4 heteroatoms selected from N, O and S, said ring being optionally mono or di-substituted with substituents independently selected from halo, hydroxyl, $C_{1-4}$-alkyl, —C(O)—$C_{1-4}$alkyl and —S(O)n$C_{1-4}$alkyl;
$R^2$ is selected from the group consisting of:
  (1) phenyl,
  (2) pyridinyl,
  (3) pyridazinyl,
  (4) pyrimidinyl,
  (5) pyrizinyl,
  (5) thiazolyl,
  (6) oxazolyl, and
  (7) pyrazolyl,
wherein choice (1), (2), (3), (4), (5), (6) and (7) are each optionally mono or di-substituted with halo, $OC_{1-4}$alkyl optionally substituted with halogen, —$C_{1-4}$-haloalkyl, hydroxyl and CN; and
$R^3$ is selected from the group consisting of:
  (1) phenyl,
  (2) pyrimidinyl,
  (3) pyridinyl,
    wherein choices (1), (2) and (3) are each optionally mono or di-substituted with halo, halo$C_{1-4}$-alkyl, or —$OC_{1-4}$-alkyl optionally substituted with halo.

12. A compound according to claim 1 selected from the group consisting of:
  4-{5-[(4-Chlorophenyl)thio]-2-phenyl-1H-imidazol-4-yl}benzonitrile,
  4-{5-[(4-Chlorophenyl)thio]-1-methyl-2-phenyl-1H-imidazol-4-yl}benzonitrile,
  4-{4-[(4-chlorophenyl)thio]-1-methyl-2-phenyl-1H-imidazol-5-yl}benzonitrile,
  5-[(4-Chlorophenyl)thio]-1,2-dimethyl-4-[4-(methylsulfonyl)phenyl]-1H-imidazole,
  5-[(4-Chlorophenyl)thio]-2-ethyl-1-methyl-4-[4-(methylsulfonyl)phenyl]-1H-imidazole,
  5-[(4-Chlorophenyl)thio]-2-isopropyl-1-methyl-4-[4-(methylsulfonyl)phenyl]-1H-imidazole,
  5-[(4-Chlorophenyl)thio]-2-cyclopentyl-1-methyl-4-[4-(methylsulfonyl)phenyl]-1H-imidazole,
  5-[(4-Chlorophenyl)thio]-2-cyclohexyl-1-methyl-4-[4-(methylsulfonyl)phenyl]-1H-imidazole,
  5-[(4-chlorophenyl)thio]-1-methyl-4-[4-(methylsulfonyl)phenyl]-2-(tetrahydro-2H-pyran-4-yl)-1H-imidazole,
  4-{5-[(4-chlorophenyl)thio]-1-methyl-1H-imidazol-4-yl}benzonitrile,
  4-{5-[(4-Chlorophenyl)thio]-2-iodo-1-methyl-1H-imidazol-4-yl}benzonitrile,
  4-{5-[(4-chlorophenyl)thio]-1-ethyl-2-phenyl-1H-imidazol-4-yl}benzonitrile,
  5-Chloro-2-({1-methyl-4-[4-(1,3,4-oxadiazol-2-yl)phenyl]-2-pyridin-2-yl-1H-imidazol-5-yl}thio)pyridine,
  2-{5-[(4-Chlorophenyl)thio]-1-methyl-4-[4-(5-methyl-1,3,4-oxadiazol-2-yl)phenyl]-1H-imidazol-2-yl}pyridine,
  4-{5-[(4-Chlorophenyl)thio]-1-methyl-2-pyridin-2-yl-1H-imidazol-4-yl}-N'-formylbenzohydrazide, 2-{5-[(4-Chlorophenyl)thio]-1-methyl-4-[4-(1,3,4-thiadiazol-2-yl)phenyl]-1H-imidazol-2-yl}pyridine,
5-(4-{5-[(4-Chlorophenyl)thio]-1-methyl-2-pyridin-2-yl-1H-imidazol-4-yl}phenyl)-1,3,4-oxadiazol-2-amine,
5-(4-{5-[(4-Chlorophenyl)thio]-1-methyl-2-pyridin-2-yl-1H-imidazol-4-yl}phenyl)-1,3,4-oxadiazol-2(3H)-one,
5-(4-{5-[(4-Chlorophenyl)thio]-1-methyl-2-pyridin-2-yl-1H-imidazol-4-yl}phenyl)-1,3,4-oxadiazol-2(3H)-thione,
1-(4-{5-[(4-Chlorophenyl)thio]-1-methyl-2-pyridin-2-yl-1H-imidazol-4-yl}phenyl)ethanone,
1-(4-{5-[(4-Chlorophenyl)thio]-1-methyl-2-pyridin-2-yl-1H-imidazol-4-yl}phenyl)ethanol,
1-(4-{5-[(4-Chlorophenyl)thio]-1-methyl-2-pyridin-2-yl-1H-imidazol-4-yl}phenyl)-2,2-difluoroethanone,
1-(4-{5-[(4-Chlorophenyl)thio]-1-methyl-2-pyridin-2-yl-1H-imidazol-4-yl}phenyl)-2,2-difluoroethanol,
1-(4-{5-[(4-Chlorophenyl)thio]-1-methyl-2-pyridin-2-yl-1H-imidazol-4-yl}phenyl)-2,2,2-trifluoroethanone,
1-(4-{5-[(4-Chlorophenyl)thio]-1-methyl-2-pyridin-2-yl-1H-imidazol-4-yl}phenyl)-2,2,2-trifluoroethanol,
Methyl 2-(4-{5-[(4-chlorophenyl)thio]-1-methyl-2-pyridin-2-yl-1H-imidazol-4-yl}phenyl)-2-methylpropanoate,
2-[5-[(4-Chlorophenyl)thio]-4-(4-iodophenyl)-1-methyl-1H-imidazol-2-yl]pyridine,
2-{5-[(4-Chlorophenyl)thio]-1-methyl-4-[4-(1H-pyrazol-1-yl)phenyl]-1H-imidazol-2-yl}pyridine,
2-{5-[(4-Chlorophenyl)thio]-4-[4-(1H-imidazol-1-yl)phenyl]-1-methyl-1H-imidazol-2-yl}pyridine,
4-{5-[(4-Chlorophenyl)thio]-1-methyl-2-phenyl-1H-imidazol-4-yl}benzamide,
3-(4-{5-[(4-Chlorophenyl)thio]-1-methyl-2-phenyl-1H-imidazol-4-yl}phenyl)-1,2,4-oxadiazole,
2-(4-{5-[(4-Chlorophenyl)thio]-1-methyl-2-phenyl-1H-imidazol-4-yl}phenyl)propan-2-ol,
4-{5-[(4-Chlorophenyl)thio]-1-methyl-2-phenyl-1H-imidazol-4-yl}benzoic acid,
5-(4-{5-[(4-Chlorophenyl)thio]-1-methyl-2-phenyl-1H-imidazol-4-yl}phenyl)-1H-1,2,4-triazole,
2-(4-{5-[(4-Chlorophenyl)thio]-1-methyl-2-phenyl-1H-imidazol-4-yl}phenyl)-2-methylpropanenitrile,
2-(4-{5-[(4-Chlorophenyl)thio]-1-methyl-2-phenyl-1H-imidazol-4-yl}phenyl)-2-methylpropanamide,
5-{5-[(4-Chlorophenyl)thio]-1-methyl-2-pyridin-2-yl-1H-imidazol-4-yl}pyridine-2-carbonitrile,
6-{5-[(4-chlorophenyl)thio]-1-methyl-2-pyridin-2-yl-1H-imidazol-4-yl}nicotinonitrile,
4-{5-[(4-Chlorophenyl)thio]-1-methyl-2-pyridin-2-yl-1H-imidazol-4-yl}aniline, and
2-{5-[(4-Chlorophenyl)thio]-1-methyl-4-[4-(2-methyl-2H-tetrazol-5-yl)phenyl]-1H-imidazol-2-yl}pyridine, or a pharmaceutically acceptable salt thereof.

13. A compound according to claim 1 selected from the group consisting of:

| Example | Compound structure |
|---|---|
| 4 | 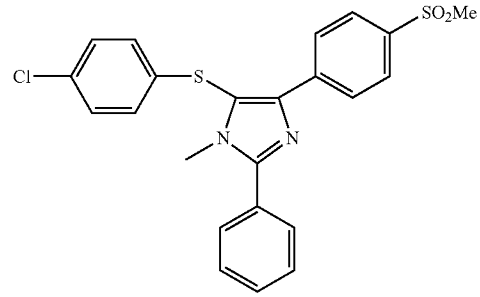 |
| 5 | 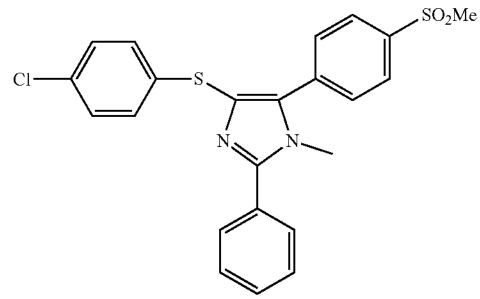 [SMILES: Cn1c(-c2ccccc2)nc(Sc2ccc(Cl)cc2)c1-c1ccc(S(C)(=O)=O)cc1] |
| 6 | 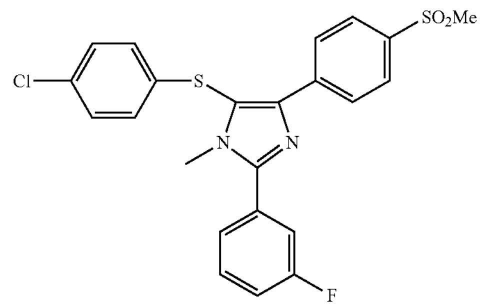 [SMILES: Cn1c(-c2cccc(F)c2)nc(-c2ccc(S(C)(=O)=O)cc2)c1Sc1ccc(Cl)cc1] |
| 7 | 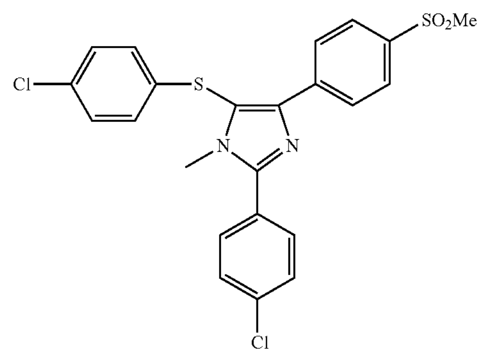 [SMILES: Cn1c(-c2ccc(Cl)cc2)nc(-c2ccc(S(C)(=O)=O)cc2)c1Sc1ccc(Cl)cc1] |
| 8 | 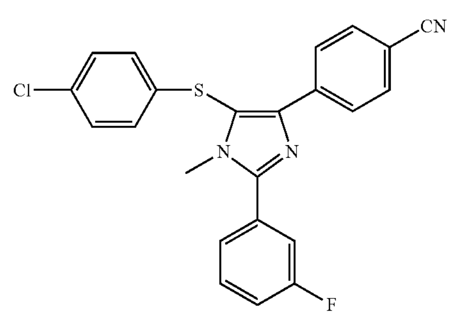 [SMILES: Cn1c(-c2cccc(F)c2)nc(-c2ccc(C#N)cc2)c1Sc1ccc(Cl)cc1] |

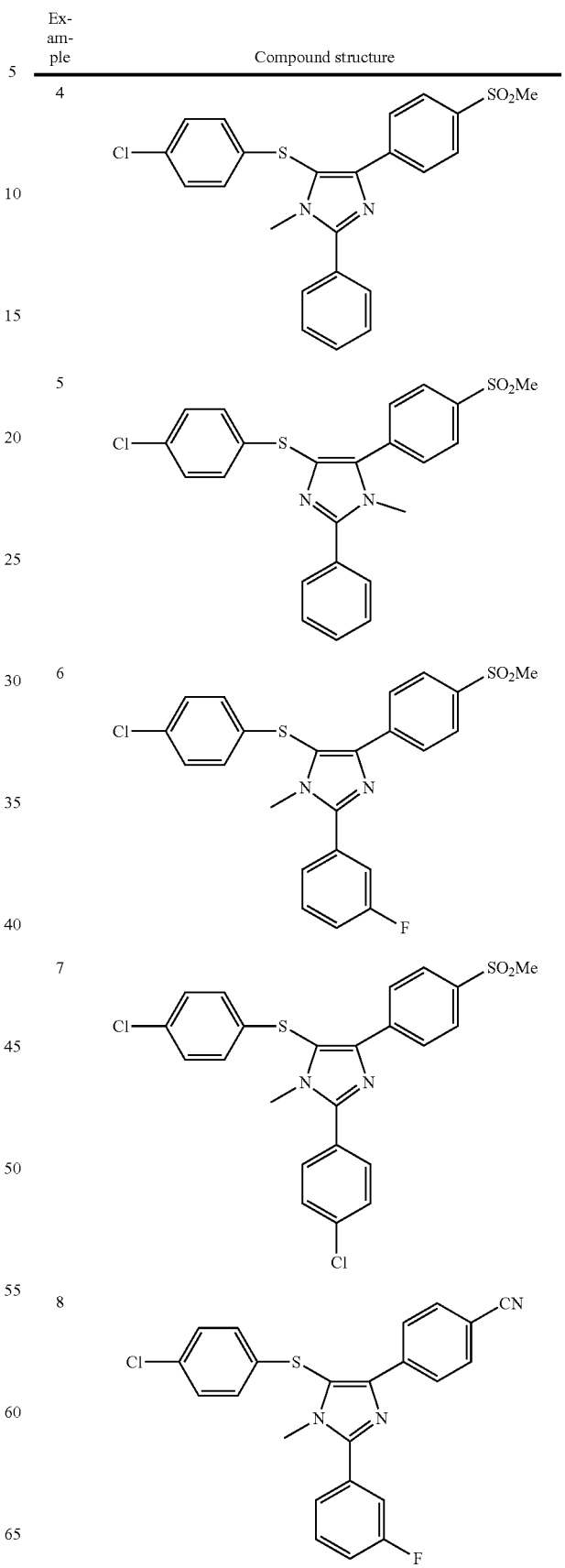

-continued
| Example | Compound structure |
|---|---|
| 9 | 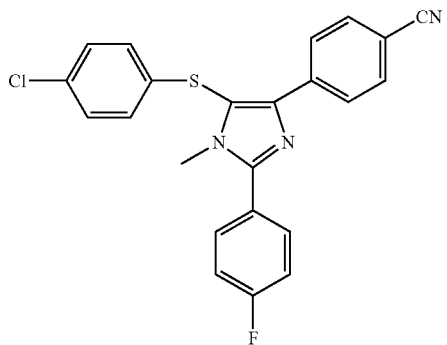 [SMILES: Cn1c(-c2ccc(F)cc2)nc(-c2ccc(C#N)cc2)c1Sc1ccc(Cl)cc1] |
| 10 | 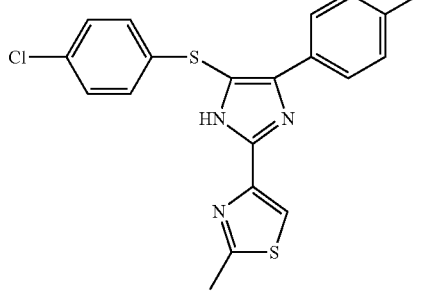 |
| 11 | 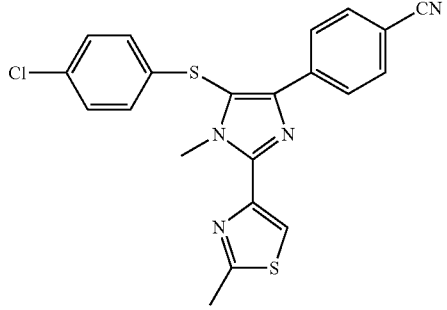 [SMILES: Cc1nc(-c2nc(-c3ccc(C#N)cc3)c(Sc3ccc(Cl)cc3)n2C)cs1] |
| 12 | 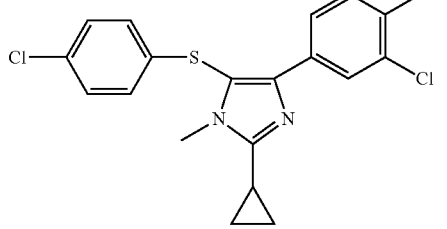 |
| 13 | 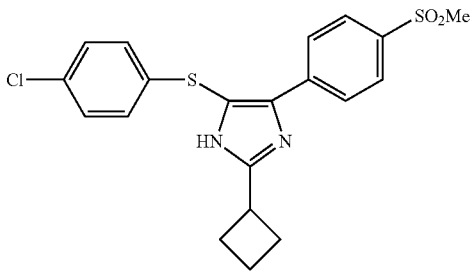 [SMILES: CS(=O)(=O)c1ccc(-c2nc(C3CCC3)[nH]c2Sc2ccc(Cl)cc2)cc1] |
-continued
| Example | Compound structure |
|---|---|
| 14 | 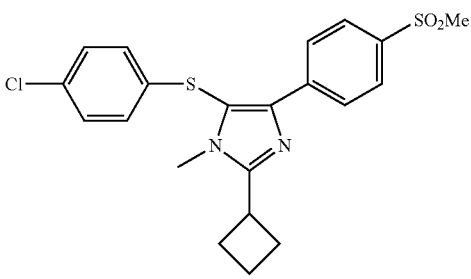 [SMILES: Cn1c(C2CCC2)nc(-c2ccc(S(C)(=O)=O)cc2)c1Sc1ccc(Cl)cc1] |
| 15 | 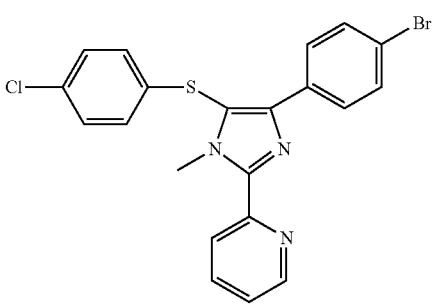 [SMILES: Cn1c(-c2ccccn2)nc(-c2ccc(Br)cc2)c1Sc1ccc(Cl)cc1] |
| 16 | 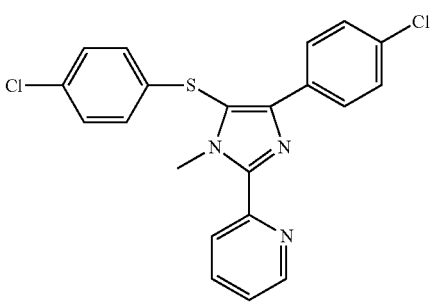 [SMILES: Cn1c(-c2ccccn2)nc(-c2ccc(Cl)cc2)c1Sc1ccc(Cl)cc1] |
| 17 | 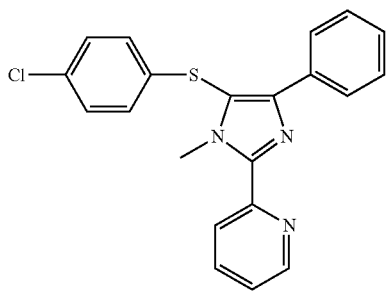 [SMILES: Cn1c(-c2ccccn2)nc(-c2ccccc2)c1Sc1ccc(Cl)cc1] |
| 18 | 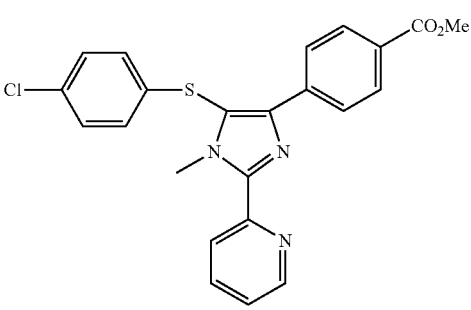 [SMILES: COC(=O)c1ccc(-c2nc(-c3ccccn3)n(C)c2Sc2ccc(Cl)cc2)cc1] |

TABLE -continued
| Example | Compound structure |
|---|---|
| 19 | 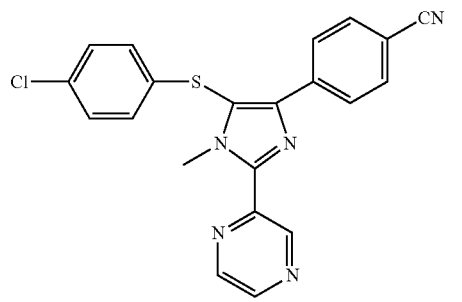 [SMILES: Cn1c(-c2cnccn2)nc(-c2ccc(C#N)cc2)c1Sc1ccc(Cl)cc1] |
| 20 | 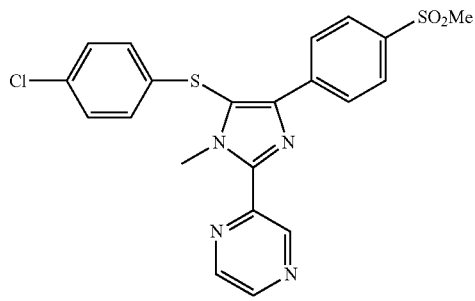 [SMILES: Cn1c(-c2cnccn2)nc(-c2ccc(S(C)(=O)=O)cc2)c1Sc1ccc(Cl)cc1] |
| 21 | 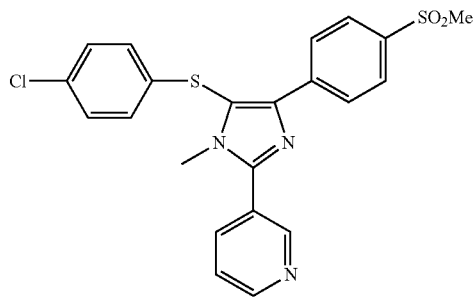 |
| 22 | 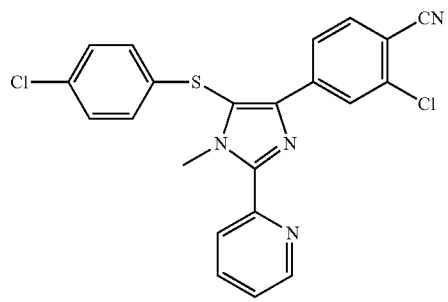 [SMILES: Cn1c(-c2ccccn2)nc(-c2ccc(C#N)c(Cl)c2)c1Sc1ccc(Cl)cc1] |
| 23 | 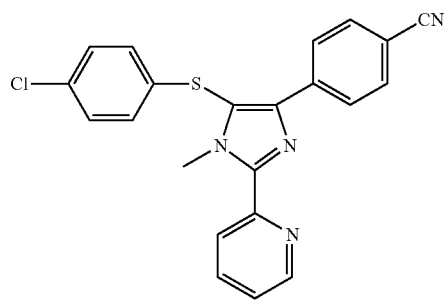 |
| 24 | 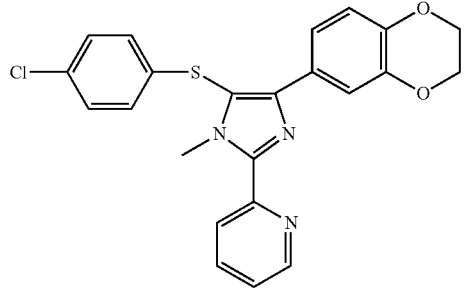 [SMILES: Cn1c(-c2ccccn2)nc(-c2ccc3c(c2)OCCO3)c1Sc1ccc(Cl)cc1] |
| 25 | 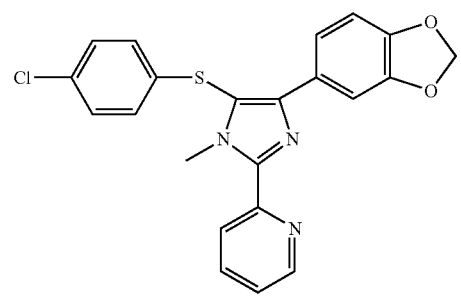 [SMILES: Cn1c(-c2ccccn2)nc(-c2ccc3c(c2)OCO3)c1Sc1ccc(Cl)cc1] |
| 26 | 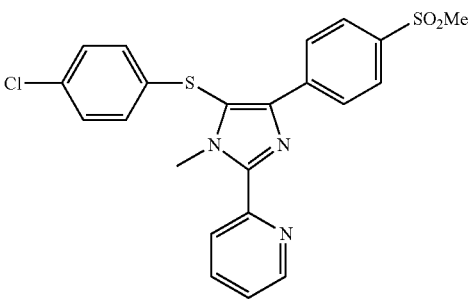 |
| 37 | 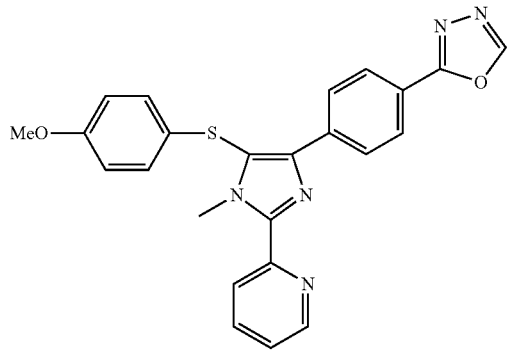 [SMILES: COc1ccc(Sc2c(-c3ccc(-c4nnco4)cc3)nc(-c3ccccn3)n2C)cc1] |

-continued

| Example | Compound structure |
|---|---|
| 38 | (structure: 5-[4-(1,3,4-oxadiazol-2-yl)phenyl]-4-{[5-(trifluoromethyl)pyridin-2-yl]thio}-1-methyl-2-(pyridin-2-yl)-1H-imidazole) |
| 39 | (structure: 5-[4-(1,3,4-oxadiazol-2-yl)phenyl]-4-{[5-(trifluoromethoxy)pyridin-2-yl]thio}-1-methyl-2-(pyridin-2-yl)-1H-imidazole) |
| 40 | (structure: 4-[(2,4-difluorophenyl)thio]-5-[4-(1,3,4-oxadiazol-2-yl)phenyl]-1-methyl-2-(pyridin-2-yl)-1H-imidazole) |
| 41 | (structure: 4-[(4-fluorophenyl)thio]-5-[4-(1,3,4-oxadiazol-2-yl)phenyl]-1-methyl-2-(pyridin-2-yl)-1H-imidazole) |

| Example | Compound structure |
|---|---|
| 42 | (structure: 4-[(3,4-difluorophenyl)thio]-5-[4-(1,3,4-oxadiazol-2-yl)phenyl]-1-methyl-2-(pyridin-2-yl)-1H-imidazole) |
| 43 | (structure: 4-[(4-chlorophenyl)thio]-5-[4-(1,3,4-oxadiazol-2-yl)phenyl]-1-methyl-2-(pyridin-2-yl)-1H-imidazole) |
| 44 | (structure: 4-{[6-(methoxy)pyridin-3-yl]thio}-5-[4-(1,3,4-oxadiazol-2-yl)phenyl]-1-methyl-2-(pyridin-2-yl)-1H-imidazole) |
| 45 | (structure: 5-[4-(1,3,4-oxadiazol-2-yl)phenyl]-4-{[5-(trifluoromethyl)pyridin-2-yl]thio}-1-methyl-2-(pyridin-2-yl)-1H-imidazole) |

| Example | Compound structure |
|---|---|
| 46 | 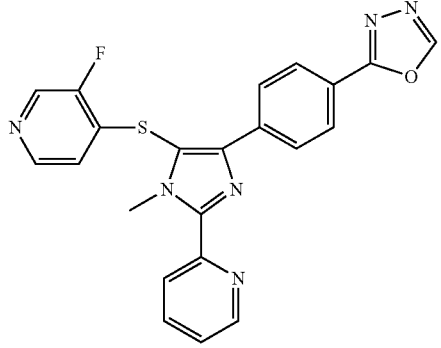 [SMILES: Cn1c(-c2ccccn2)nc(-c2ccc(-c3nnco3)cc2)c1Sc1ccncc1F] |
| 47 | 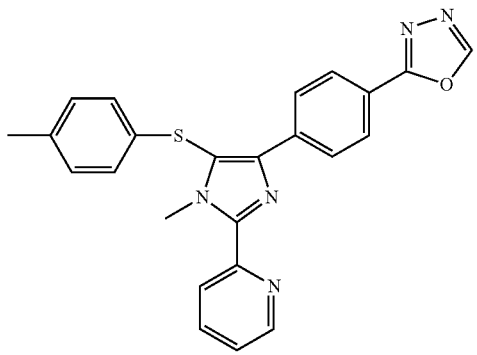 [SMILES: Cc1ccc(Sc2c(-c3ccc(-c4nnco4)cc3)nc(-c3ccccn3)n2C)cc1] |
| 64 | 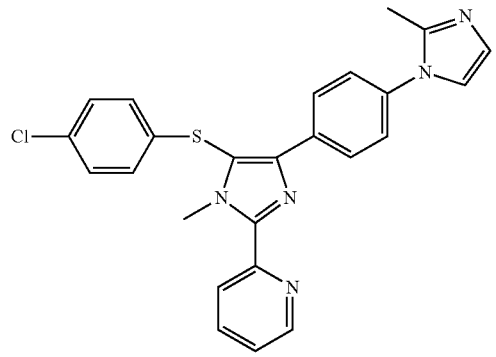 [SMILES: Cc1nccn1-c1ccc(-c2nc(-c3ccccn3)n(C)c2Sc2ccc(Cl)cc2)cc1] |
| 65 | 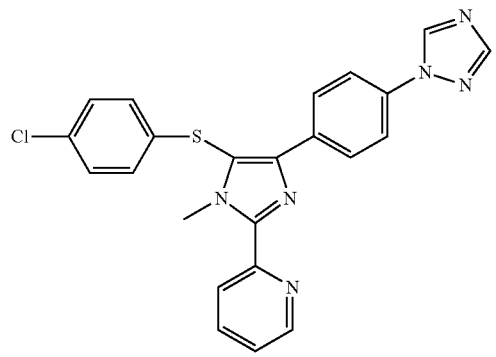 [SMILES: Cn1c(-c2ccccn2)nc(-c2ccc(-n3cncn3)cc2)c1Sc1ccc(Cl)cc1] |
| Example | Compound structure |
|---|---|
| 66 | 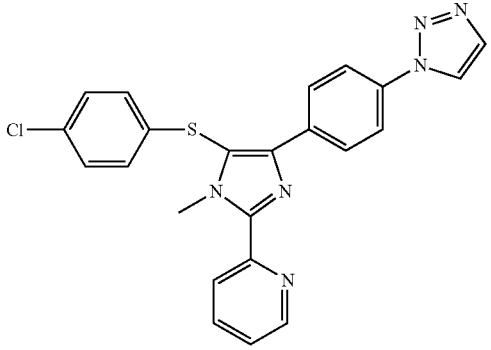 [SMILES: Cn1c(-c2ccccn2)nc(-c2ccc(-n3ccnn3)cc2)c1Sc1ccc(Cl)cc1] |
| 67 | 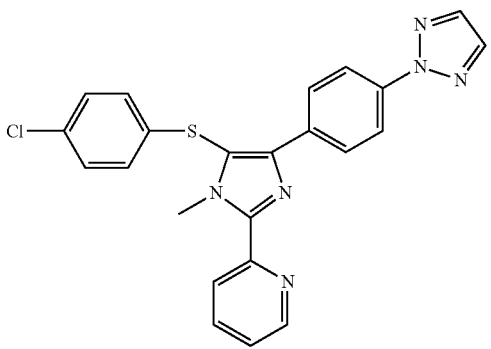 [SMILES: Cn1c(-c2ccccn2)nc(-c2ccc(-n3nccn3)cc2)c1Sc1ccc(Cl)cc1] |
| 68 | 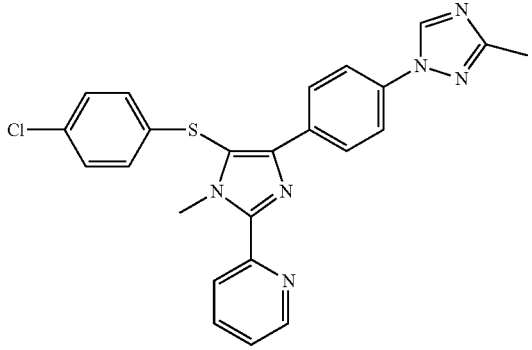 [SMILES: Cc1ncn(-c2ccc(-c3nc(-c4ccccn4)n(C)c3Sc3ccc(Cl)cc3)cc2)n1] |
| 69 | 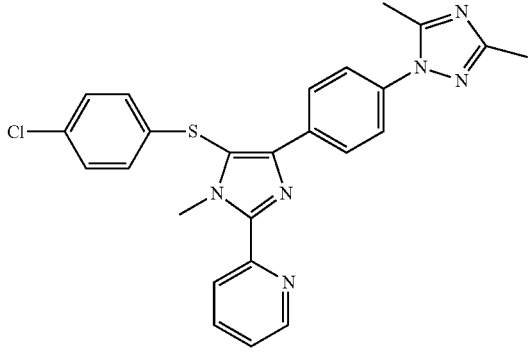 [SMILES: Cc1nc(C)n(-c2ccc(-c3nc(-c4ccccn4)n(C)c3Sc3ccc(Cl)cc3)cc2)n1] |

-continued
| Example | Compound structure |
|---|---|
| 70 | 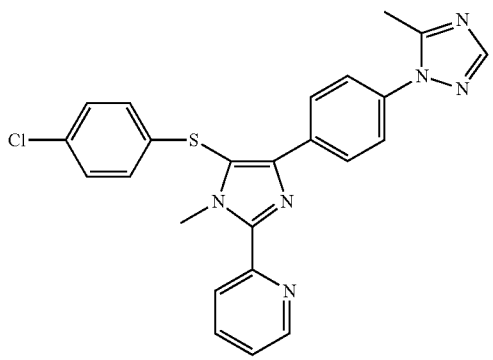 [SMILES: Cc1ncnn1-c1ccc(-c2nc(-c3ccccn3)n(C)c2Sc2ccc(Cl)cc2)cc1] |
| 80 | 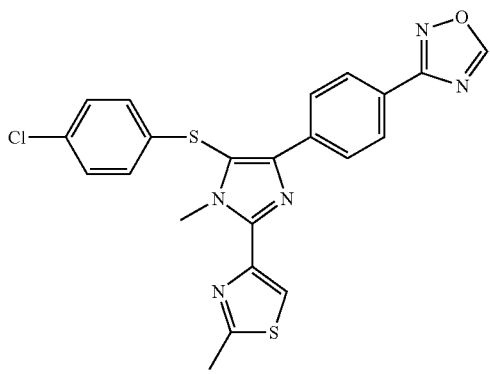 [SMILES: Cc1nc(-c2nc(-c3ccc(-c4ncon4)cc3)c(Sc3ccc(Cl)cc3)n2C)cs1] |
| 81 | 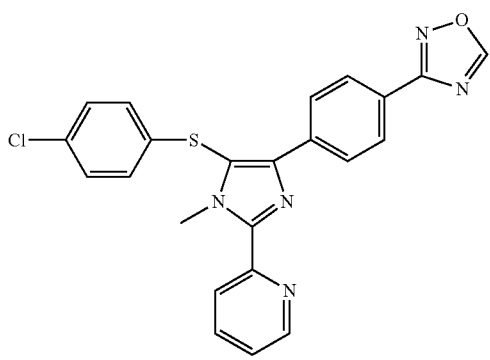 [SMILES: Cn1c(-c2ccccn2)nc(-c2ccc(-c3ncon3)cc2)c1Sc1ccc(Cl)cc1] |
| 82 | 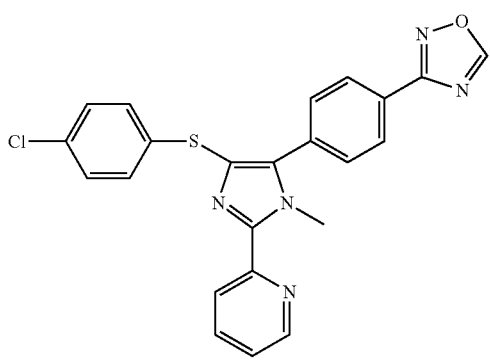 [SMILES: Cn1c(-c2ccccn2)nc(Sc2ccc(Cl)cc2)c1-c1ccc(-c2ncon2)cc1] |
-continued
| Example | Compound structure |
|---|---|
| 83 | 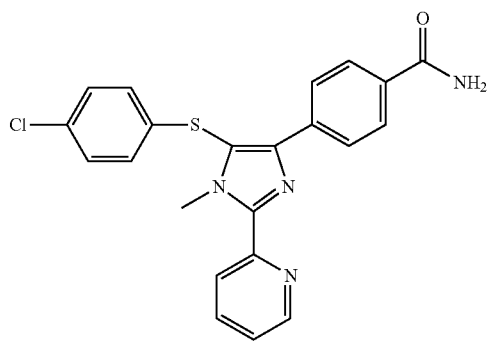 [SMILES: Cn1c(-c2ccccn2)nc(-c2ccc(C(N)=O)cc2)c1Sc1ccc(Cl)cc1] |
| 84 | 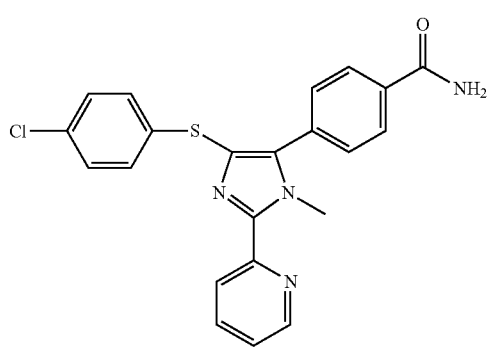 [SMILES: Cn1c(-c2ccccn2)nc(Sc2ccc(Cl)cc2)c1-c1ccc(C(N)=O)cc1] |
| 85 | 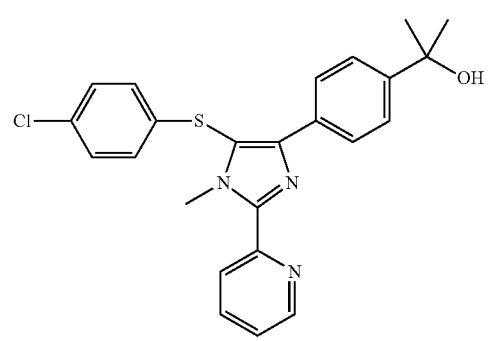 [SMILES: Cn1c(-c2ccccn2)nc(-c2ccc(C(C)(C)O)cc2)c1Sc1ccc(Cl)cc1] |
| 86 | 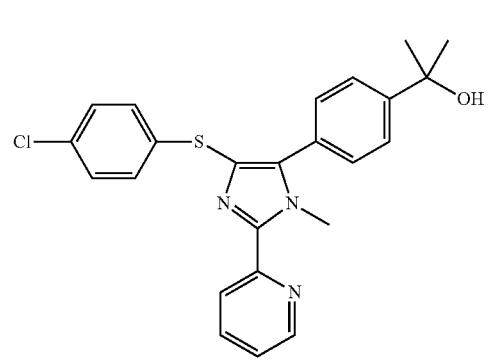 [SMILES: Cn1c(-c2ccccn2)nc(Sc2ccc(Cl)cc2)c1-c1ccc(C(C)(C)O)cc1] |

| Example | Compound structure |
|---|---|
| 87 | 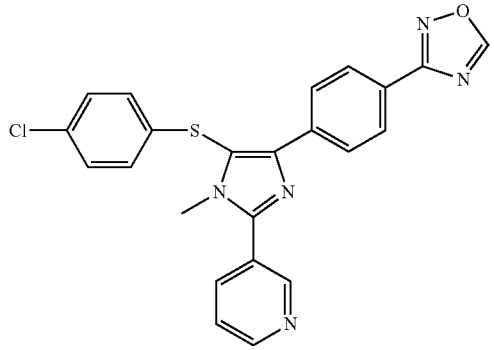 |
| 88 | 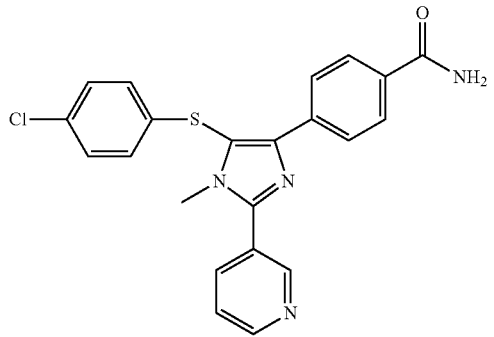 |
| 89 | 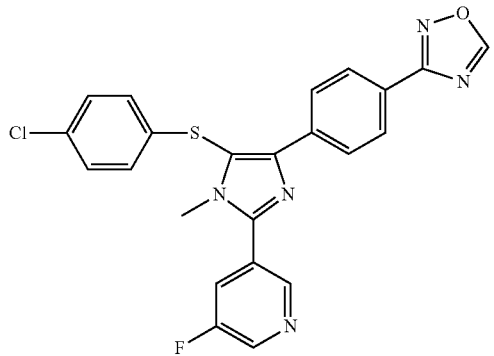 [SMILES: Cn1c(-c2cncc(F)c2)nc(-c2ccc(-c3ncon3)cc2)c1Sc1ccc(Cl)cc1] |
| 90 | 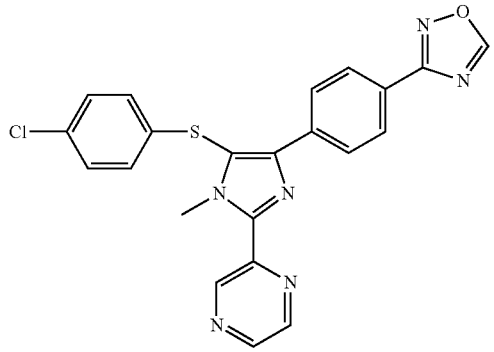 |
| 91 | 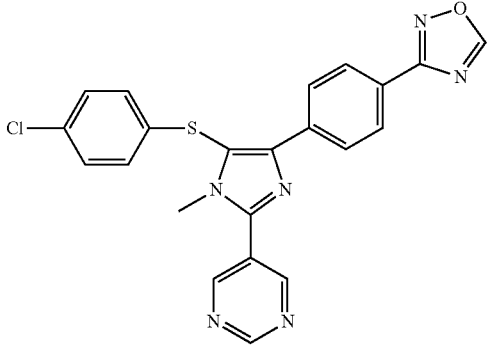 [SMILES: Cn1c(-c2cncnc2)nc(-c2ccc(-c3ncon3)cc2)c1Sc1ccc(Cl)cc1] |
| 92 | 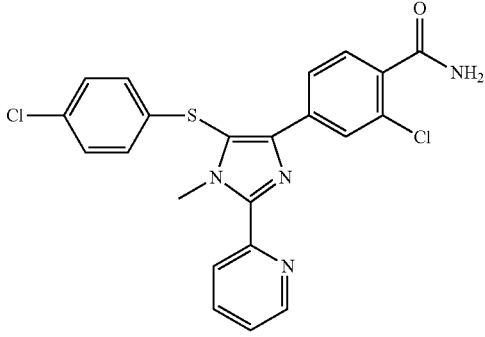 [SMILES: Cn1c(-c2ccccn2)nc(-c2ccc(C(N)=O)c(Cl)c2)c1Sc1ccc(Cl)cc1] |
| 93 | 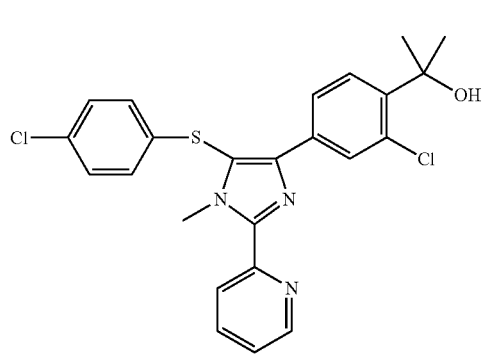 [SMILES: Cn1c(-c2ccccn2)nc(-c2ccc(C(C)(C)O)c(F)c2)c1Sc1ccc(Cl)cc1] |
| 94 | 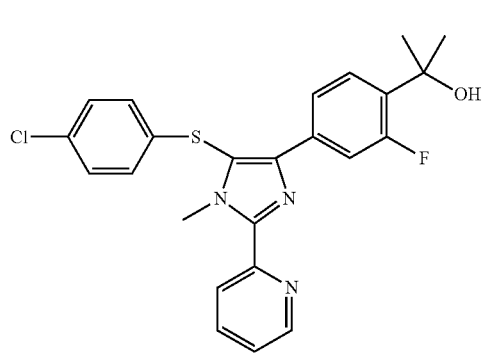 |

-continued

| Example | Compound structure |
|---|---|
| 95 | 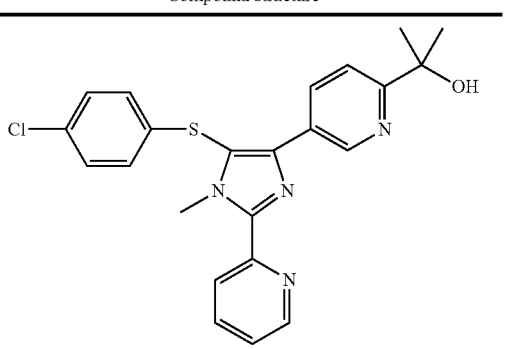 |
| 96 | 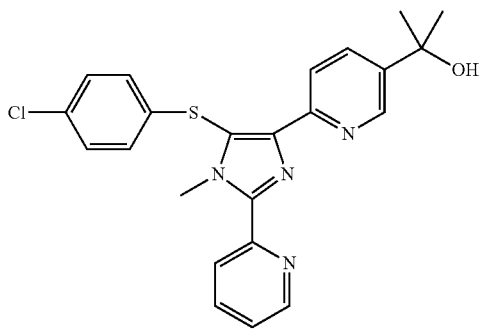 [SMILES: Cn1c(-c2ccccn2)nc(-c2ccc(C(C)(C)O)cn2)c1Sc1ccc(Cl)cc1] |
| 97 | 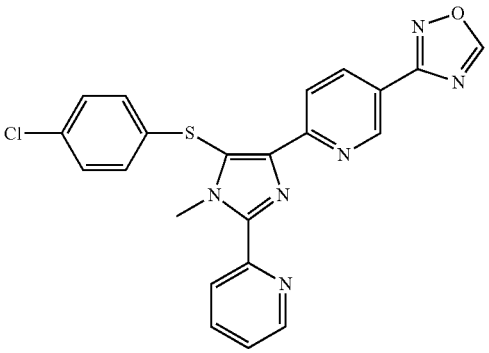 [SMILES: Cn1c(-c2ccccn2)nc(-c2ccc(-c3ncon3)cn2)c1Sc1ccc(Cl)cc1] | or a pharmaceutically acceptable salt thereof.

14. A compound according to claim 1, selected from
5-Chloro-2-({1-methyl-4-[6-(methylsulfonyl)pyridin-3-yl]-2-pyridin-2-yl-1H-imidazol-5-yl}thio)pyridine,
2-(5-{5-[(4-Chlorophenyl)thio]-1-methyl-2-pyridin-2-yl-1H-imidazol-4-yl}pyridin-2-yl)propan-2-ol,
5-[(4-chlorophenyl)thio]-4-[4-(2-furyl)phenyl]-1-methyl-2-pyridin-2-yl-1H-imidazol-3-ium trifluoroacetate,
2-{5-[(4-chlorophenyl)thio]-1-methyl-4-[4-(1,3-thiazol-2-yl)phenyl]-1H-imidazol-2-yl}pyridine,
ethyl 4-{5-[(5-chloropyridin-2-yl)thio]-1-methyl-1H-imidazol-4-yl}benzoate,
2-(4-{5-[(5-chloropyridin-2-yl)thio]-1-methyl-1H-imidazol-4-yl}phenoxy)-2-methylpropanamide,
5-[(5-chloropyridin-2-yl)thio]-4-[4-(2-hydroxy-1,1-dimethylethoxy)phenyl]-1-methyl-1H-imidazol-3-ium trifluoroacetate,
3-(4-{5-[(5-chloropyridin-2-yl)thio]-1-methyl-1H-imidazol-4-yl}phenoxy)-1,1,1-trifluoro-3-methylbutan-2-ol,
4-{5-[(4-chlorophenyl)thio]-1-methyl-2-pyridin-2-yl-1H-imidazol-4-yl}-N-(2-hydroxy-1-methylethyl)benzamide,
3-[(4-chlorophenyl)thio]-2-[4-(methylsulfonyl)phenyl]-5,6,6a,7,8,9,10,10a-octahydroimidazo[1,2-h]-1,7-naphthyridine,
2-(4-{3-[(4-chlorophenyl)sulfanyl]imidazo[1,2-h][1,7]naphthyridin-2-yl}phenyl)propan-2-ol,
6-{5-[(5-chloropyridin-2-yl)sulfanyl]-2-cyclopropyl-1-methyl-1H-imidazol-4-yl}-2-difluoromethyl)quinoline,
6-{5-[(5-chloropyridin-2-yl)thio]-2-cyclopropyl-1-methyl-1H-imidazol-4-yl}-N,N-dimethylquinoline-2-carboxamide,
5-[(4-chlorophenyl)thio]-2-iodo-1-methyl-4-[4-(methylsulfonyl)phenyl]-1H-imidazole,
4-{5-[(4-chlorophenyl)sulfanyl]-1-methyl-4-[4-(methylsulfonyl)phenyl]-1H-imidazol-2-yl}-1-methyl-1H-pyrazole,
3-4-({5-[(4-chlorophenyl)sulfanyl]-2-(1-ethyl-1H-pyrazol-3-yl)-1-methyl-1H-imidazol-4-yl}phenyl)-1,2,4-oxadiazole,
3-(4-{5-[(4-chlorophenyl)sulfanyl]-2-(1-ethyl-1H-pyrazol-5-yl)-1-methyl-1H-imidazol-4-yl}phenyl)-1,2,4-oxadiazole,
3-(4-{5-[(4-chlorophenyl)sulfanyl]-1-methyl-2-[1-(propan-2-yl)-1H-pyrazol-3-yl]-1H-imidazol-4-yl}phenyl)-1,2,4-oxadiazole,
3-(4-{5-[(4-chlorophenyl)sulfanyl]-1-methyl-2-(1-methyl-1H-pyrazol-3-yl)-1H-imidazol-4-yl}phenyl)-1,2,4-oxadiazole,
3-(4-{5-[(4-chlorophenyl)sulfanyl]-2-(1-cyclopropyl-1H-pyrazol-3-yl)-1-methyl-1H-imidazol-4-yl}phenyl)-1,2,4-oxadiazole,
4-{5-[(4-chlorophenyl)sulfanyl]-2-[1-(2-hydroxy-2-methylpropyl)-1H-pyrazol-3-yl]-1-methyl-1H-imidazol-4-yl}benzonitrile,
2-{5-[(4-chlorophenyl)sulfanyl]-1-methyl-4-[4-(1,2,4-oxadiazol-3-yl)phenyl]-1H-imidazol-2-yl}propan-2-ol,
3-(4-{5-[(4-chlorophenyl)sulfanyl]-2-(2-ethoxypropan-2-yl)-1-methyl-1H-imidazol-4-yl}phenyl)-1,2,4-oxadiazole,
2-(5-{5-[(5-chloropyridin-2-yl)sulfanyl]-2-(5-cyclopropylisoxazol-3-yl)-1-methyl-1H-imidazol-4-yl}pyridin-2-yl)propan-2-ol, or a pharmaceutically acceptable salt thereof.

15. A compound according to claim 1, selected from

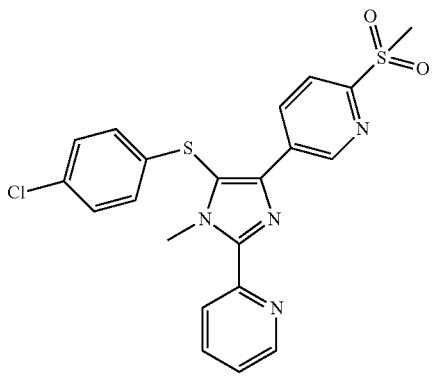

151
-continued
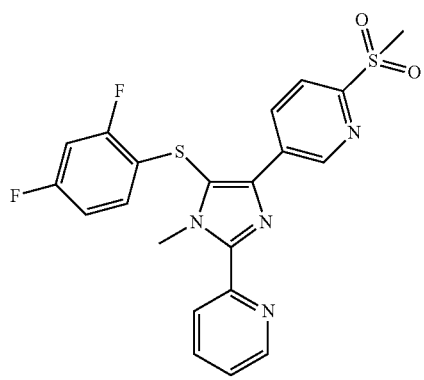
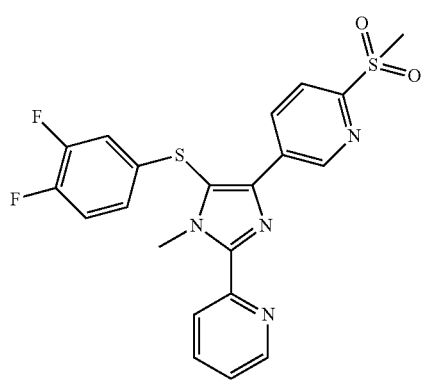
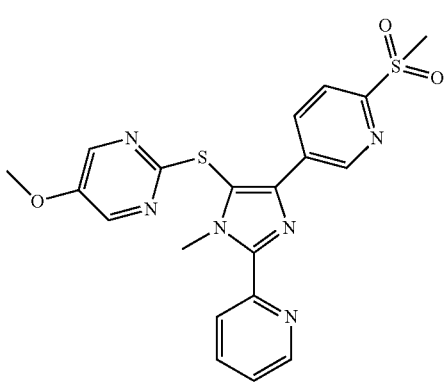
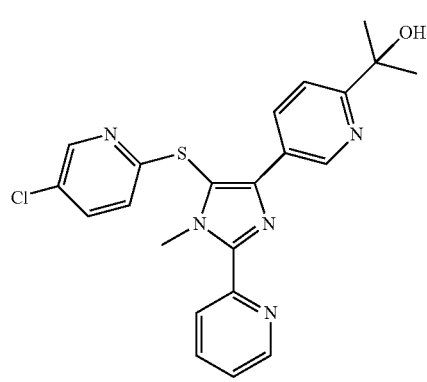
152
-continued
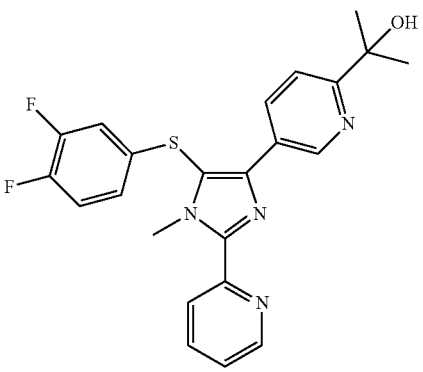
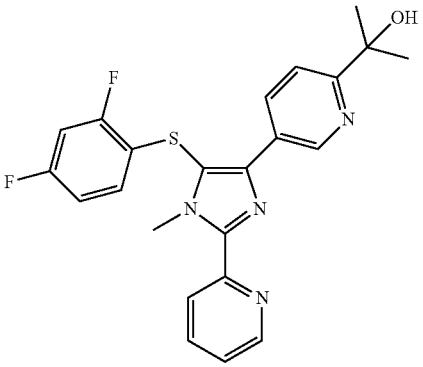
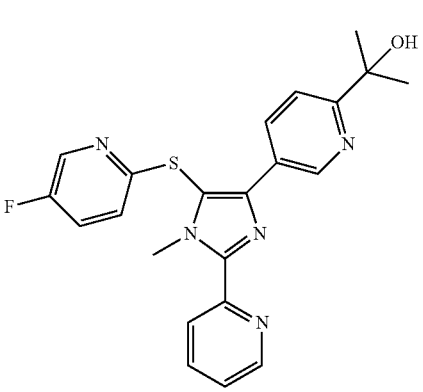
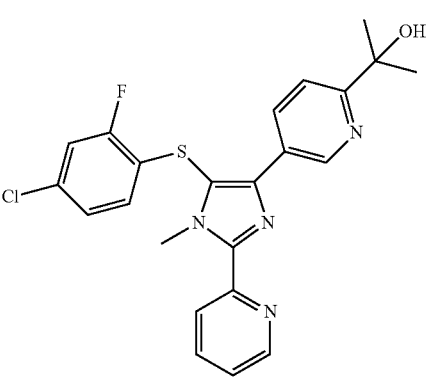

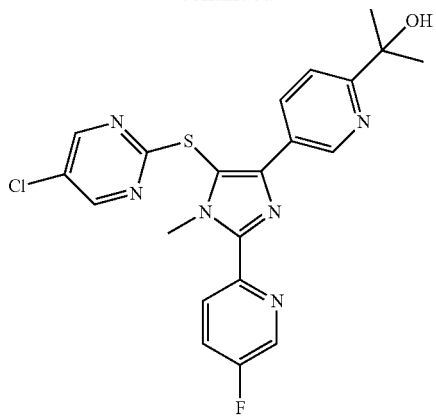
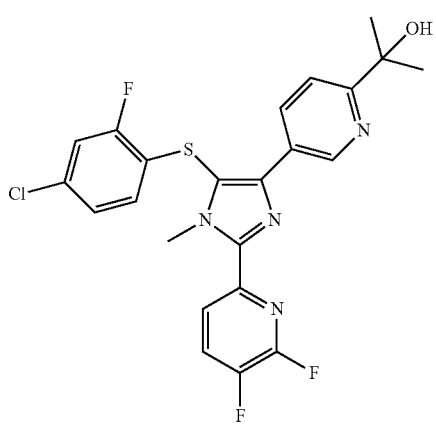
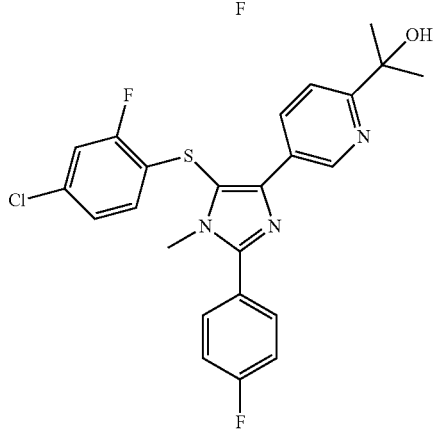
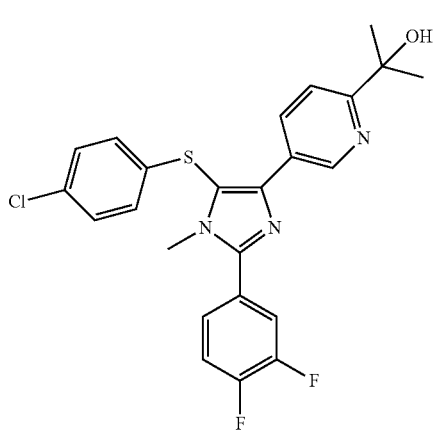
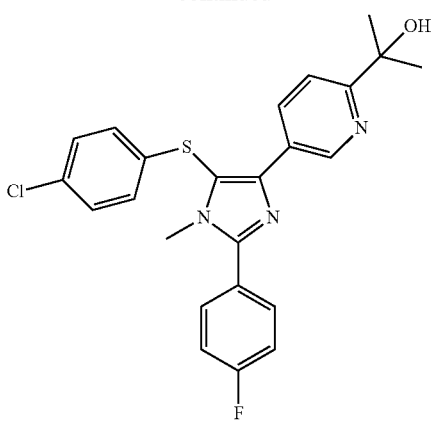
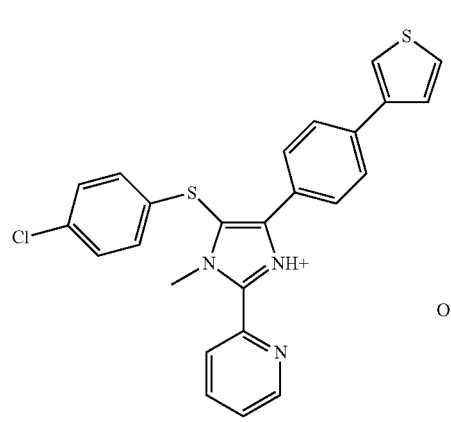
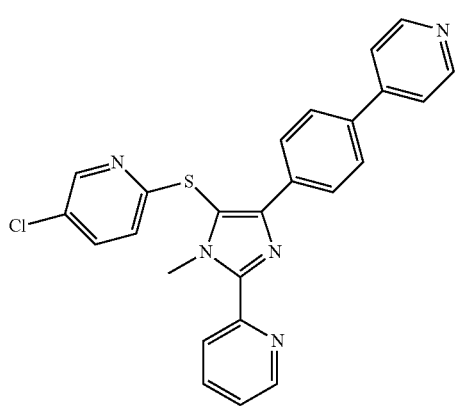
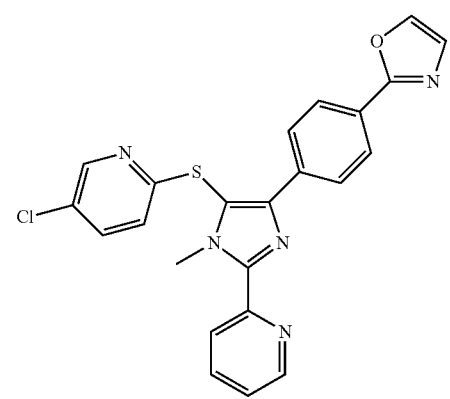

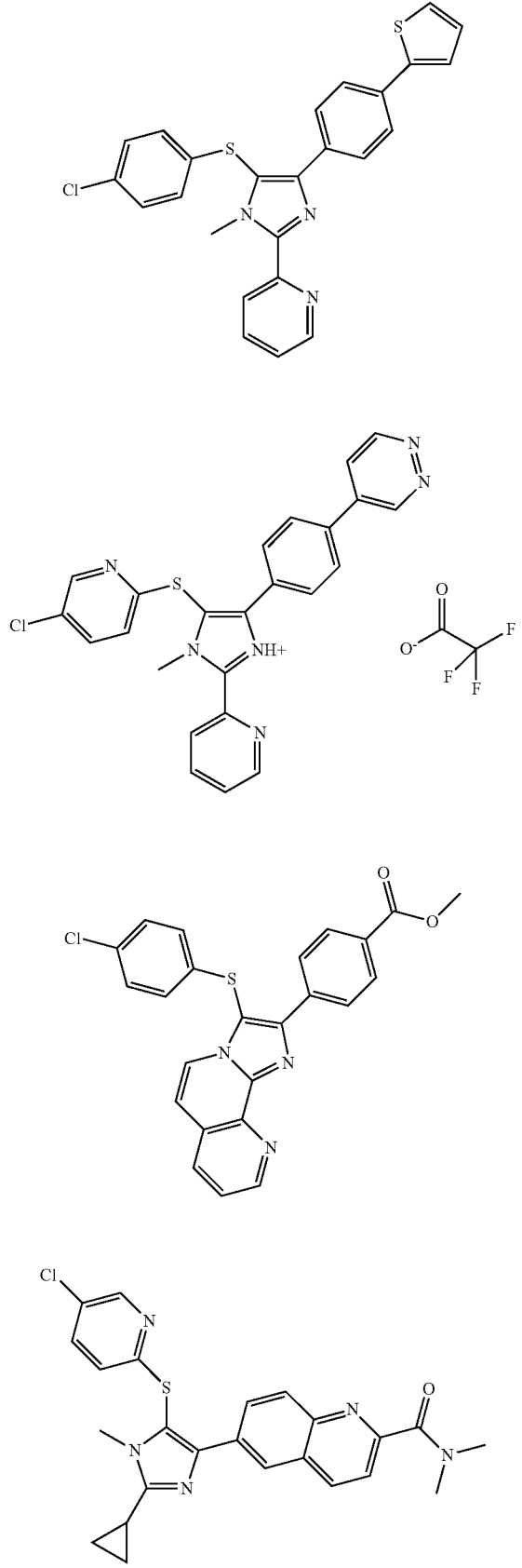
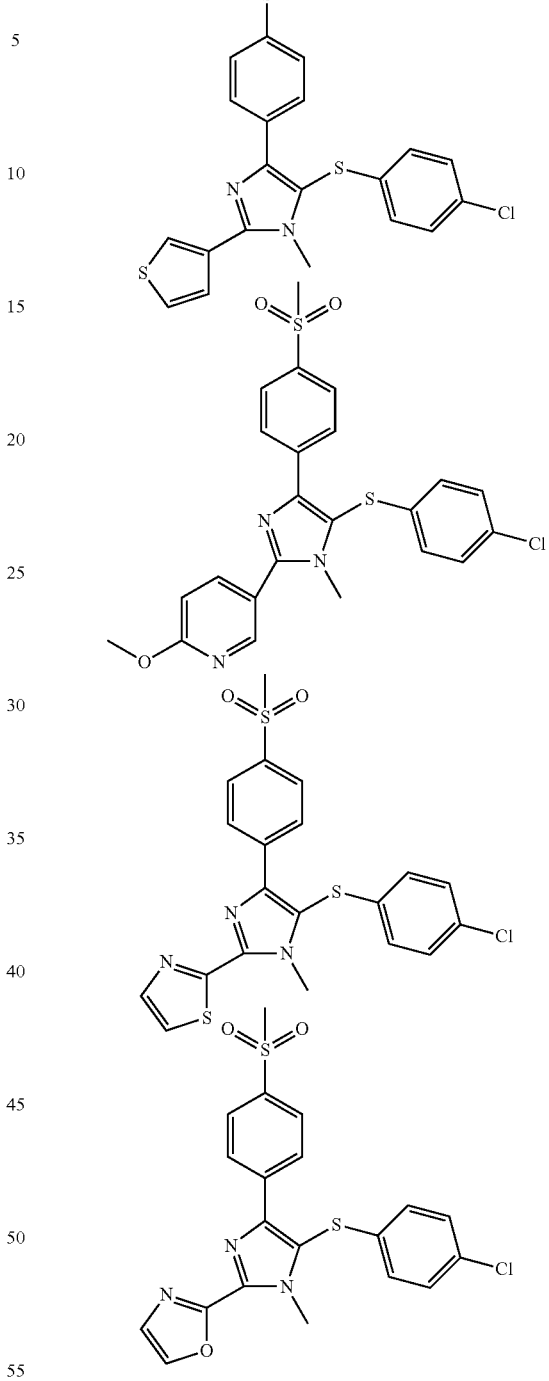

or a pharmaceutically acceptable salt thereof.

16. A pharmaceutical composition which comprises an inert carrier and a compound of claim 1 or a pharmaceutically acceptable salt thereof.

17. A method for treating a subject having a disease or disorder, wherein the disease or disorder is selected from osteoarthritis, rheumatoid arthritis, diabetic neuropathy, postherpetic neuralgia, skeletomuscular pain, and fibromyalgia, acute pain, migraine, and sleep disorder, wherein the subject is administered a compound of claim 1 in an amount effective to treat the subject, so as to thereby treat the subject.

* * * * *

```
                        SEQUENCE LISTING

<160> NUMBER OF SEQ ID NOS: 3

<210> SEQ ID NO 1
<211> LENGTH: 36
<212> TYPE: DNA
<213> ORGANISM: Unknown
<220> FEATURE:
<223> OTHER INFORMATION: Primer

<400> SEQUENCE: 1
caaggtaccg ccaccatggt gctgagcgaa gtgtgg                             36

<210> SEQ ID NO 2
<211> LENGTH: 30
<212> TYPE: DNA
<213> ORGANISM: Unknown
<220> FEATURE:
<223> OTHER INFORMATION: Primer

<400> SEQUENCE: 2
ccggaattct caagatggcc gcttttcagg                                    30

<210> SEQ ID NO 3
<211> LENGTH: 30
<212> TYPE: DNA
<213> ORGANISM: Unknown
<220> FEATURE:
<223> OTHER INFORMATION: Primer

<400> SEQUENCE: 3
ccggaattct cacgatggct gcttttgagg                                    30
```